(12) United States Patent
Manoharan et al.

(10) Patent No.: US 6,825,338 B2
(45) Date of Patent: Nov. 30, 2004

(54) LABELED OLIGONUCLEOTIDES, METHODS FOR MAKING SAME, AND COMPOUNDS USEFUL THEREFOR

(75) Inventors: Muthiah Manoharan, Carlsbad, CA (US); Andrei P. Guzaev, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/823,031

(22) Filed: Mar. 30, 2001

(65) Prior Publication Data

US 2003/0208061 A1 Nov. 6, 2003

(51) Int. Cl.[7] .................. C07H 21/00; C07H 21/02; C07H 21/04
(52) U.S. Cl. ............... 536/25.3; 536/22.1; 536/23.1; 536/25.31; 536/25.32; 536/25.33; 536/25.34
(58) Field of Search .................. 536/23.1, 22.1, 536/25.3, 25.31, 25.33, 25.34; 435/6

(56) References Cited

U.S. PATENT DOCUMENTS

| | | | |
|---|---|---|---|
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,725,677 A | 2/1988 | Köster et al. | 536/27 |
| 4,973,679 A | 11/1990 | Caruthers et al. | 536/27 |
| 5,132,418 A | 7/1992 | Caruthers et al. | 536/27 |
| RE34,069 E | 9/1992 | Koster et al. | 536/27 |
| 5,149,798 A | 9/1992 | Agrawal et al. | 536/27 |
| 5,210,264 A | 5/1993 | Yau | 558/167 |
| 5,959,090 A * | 9/1999 | Guzaev et al. | 536/23.1 |
| 6,121,437 A | 9/2000 | Guzaev et al. | 536/26.1 |
| 6,194,598 B1 | 2/2001 | Cook et al. | 558/70 |
| 6,277,982 B1 | 8/2001 | Fraser et al. | 536/25.3 |

FOREIGN PATENT DOCUMENTS

| WO | WO 96/39413 | 12/1996 |
|---|---|---|

OTHER PUBLICATIONS

Agrawal, S., "Protocols for oligonucleotides and analogs", 1993, Human Press, Totowa, NJ.

Bannwarth, W., "Synthesis of Oligodeoxynucleotides by the Phosphite–Triester Method Using Dimer Units and Different Phosphorous–Protecting Groups," Helvetica Chim. Acta, 1985, 68, 1907–1913.

Beaucage, S. L. et al., "Deoxynucleoside Phosphoramidites–A New Class of Key Intermediates for Deoxypolynucleotide Synthesis," Tetrahedron Letts., 1981, 22, 1859–1862.

Beaucage, S. L. et al., "Advances in the Synthesis of Oligonucleotides by the Phosphoramidite Approach," Tetrahedron, 1992, 48, 2223–2311.

Iyer, R. P., "Solid–Phase Stereoselective Synthesis of Oligonucleoside PhosphorothioAtes: The Nucleoside Bicyclic Oxazaphospholidines as Novel Synthons," Tetrahedron Letts., 1998, 39, 2491–2494.

Khorana, H. G. et al., "Studies on Polynucleotides: Total Synthesis of the Structural Gene for an Alanine Transfer Ribonucleic Acid from Yeast," J. Mol. Biol., 1972, 72, 209–217.

Kumar, G. et al., "Improvements in Oligodeoxyribonucleotide Synthesis: Methyl N,N–Dialkylphosphoramidite Dimer Units for Solid Support Phosphite Methodology," J. Org. Chem., 1984, 49, 4905–4912.

Miura, K. et al., "Blockwise Mechanical Synthesis of Oligonucleotides by the Phosphoramidite Method," Chem Pharm. Bull., 1987, 35, 833–836.

Reese, C. B. et al., "The Chemical Synthesis of Oligo–and Poly–Nucleotides by the Phosphotriester Approach," Tetrahedron, 1978, 34, 3143–3179.

Wilk, A. et al., "N–Trifluoroacetylamino Alcohols as Phosphodiester Protecting Groups in the Synthesis of Oligodeoxyribonucleotides," J. Org. Chem., 1997, 62, 6712–6713.

Wolter, A. et al., Polymer Support Oligonucleotide Synthesis XX: Synthesis of a Henhectacosa Deoxynucleotide by use of a Dimeric Phosphoramidite Nucleosides & Nucleotides, 1986, 5, 65–77.

Zioudrou, C. et al., "The Participation of the Amide Group in the Solvolysis of Phosphoric Acid Esters. I. Phosphotriesters in Alkaline Media," J. Amer. Chem. Soc., 1963, 82, 3258–3264.

* cited by examiner

Primary Examiner—Janet L. Epps-Ford
(74) Attorney, Agent, or Firm—ISIS Patent Department; Woodcock Washburn LLP

(57) ABSTRACT

Selectively functionalized oligonucleotides, methods for making same, and compounds useful therefor are disclosed. The oligonucleotides can be selectively functionalized with a first conjugate group at the 3'-terminial position and optionally functionalized with a second conjugate group at the 5'-terminal position and/or one or more internucleotides. Alternatively, the oligonucleotides can be selectively functionalized with a first conjugate group at the 5'-terminal position and optionally functionalized with a second conjugate group at one or more internucleotides. In yet another embodiment, the oligonucleotides can be functionalized with a first conjugate group at one or more internucleotides and with a second conjugate group at one or more different internucleotides.

25 Claims, 10 Drawing Sheets

LABELED OLIGONUCLEOTIDES, METHODS FOR MAKING SAME, AND COMPOUNDS USEFUL THEREFOR

FIELD OF THE INVENTION

The present invention is directed to labeled oligonucleotides, methods for making the same, and compounds useful therefor. More specifically, this invention relates to oligonucleotides selectively functionalized at one or more of the 3'-terminalnucleotide, 5'-terminalnucleotide, and internucleotides with conjugate groups, methods for making the same, and compounds useful therefor.

BACKGROUND OF THE INVENTION

Oligonucleotides and their analogs have been developed and used in molecular biology in a variety of procedures as probes, primers, linkers, adapters, and gene fragments. The widespread use of such oligonucleotides has increased the demand for rapid, inexpensive and efficient procedures for their modification and synthesis. Early synthetic approaches to oligonucleotide synthesis included phosphodiester and phosphotriester chemistries. Khorana et al., *J. Molec. Biol.* 72, 209, 1972; Reese, *Tetrahedron Lett.* 34, 3143–3179, 1978. These approaches eventually gave way to more efficient modern methods, such as the use of phosphoramidites and H-phosphonates. Beaucage and Caruthers, *Tetrahedron Lett.*, 22, 1859–1862, 1981; Agrawal and Zamecnik, U.S. Pat. No. 5,149,798, issued 1992.

The chemical literature discloses numerous processes for coupling nucleosides through phosphorous-containing covalent linkages to produce oligonucleotides of defined sequence. One of the most popular processes is the phosphoramidite technique (see, e.g., Advances in the Synthesis of Oligonucleotides by the Phosphoramidite Approach, Beaucage, S. L.; Iyer, R. P., *Tetrahedron*, 1992, 48, 2223–2311 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

The phosphoramidite technique, however, has significant disadvantages. For example, cyanoethyl phosphoramidite monomers are quite expensive. Although considerable quantities of monomer go unreacted in a typical phosphoramidite coupling, unreacted monomer can be recovered, if at all, only with great difficulty.

The ability of the acylaminoethyl group to serve as a protecting group for certain phosphate diesters was first observed by Ziodrou and Schmir. Zioudrou et al., *J. Amer. Chem. Soc.*, 85, 3258, 1963. A version of this method was extended to the solid phase synthesis of oligonucleotide dimers, and oligomers with oxaphospholidine nucleoside building blocks as substitutes for conventional phosphoramidites. Iyer et al., *Tetrahedron Lett.*, 39, 2491–2494, 1998; PCT International Publication WO/9639413, published Dec. 12, 1996. Similar methods using N-trifluoroacetyl-aminoalkanols as phosphate protecting groups has also been reported by Wilk et al., *J. Org. Chem.*, 62, 6712–6713, 1997. This deprotection is governed by a mechanism that involves removal of N-trifluoroacetyl group followed by cyclization of aminoalkyl phosphotriesters to azacyclanes, which is accompanied by the release of the phosphodiester group.

Solid phase techniques continue to play a large role in oligonucleotidic synthetic approaches. Typically, the 3'-most nucleoside is anchored to a solid support which is functionalized with hydroxyl or amino residues. The additional nucleosides are subsequently added in a step-wise fashion to form the desired linkages between the 3'-functional group of the incoming nucleoside, and the 5'-hydroxyl group of the support bound nucleoside. Implicit to this step-wise assembly is the judicious choice of suitable phosphorus protecting groups. Such protecting groups serve to shield phosphorus moieties of the nucleoside base portion of the growing oligomer until such time that it is cleaved from the solid support. Consequently, new protecting groups, which are versatile in oligonucleotidic synthesis, are needed.

A variety of modifications to naturally occurring oligonucleotides have been proposed. Such modifications include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents. Other mechanisms of action have also been proposed.

Transcription factors interact with double-stranded DNA during regulation of transcription. Oligonucleotides can serve as competitive inhibitors of transcription factors to modulate their action. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

For example, antisense oligonucleotides have been modified to be conjugated with lipophilic molecules. The presence of the lipophilic conjugate has been shown to improve cellular permeation of the oligonucleotide and, accordingly, improve distribution of the oligonucleotide in cells. Further, oligonucleotides conjugated with lipophilic molecules are able to enhance the free uptake of the oligonucleotides without the need for any transfection agents in cell culture studies. Conjugated oligonucleotides are also able to improve the protein binding of oligonucleotides containing phosphodiester linkages.

Recently, oligonucleotides selectively labeled with two different reporter groups have attained a widespread interest due to their unique properties. For example, if the reporter groups are paired as a donor and an acceptor of fluorescent energy, a fluorescence resonance energy transfer (FRET) between the two groups may occur. When the distance between the donor and acceptor groups is short, quenching of the fluorescence is observed. In contrast, when the donor and acceptor are sufficiently far apart, a fluorescent signal is observed. Such a phenomenon has been used to detect formation of a complex between a suitably labeled oligonucleotide and a complementary target nucleic acid. When the oligonucleotide is uncomplexed, the donor and the acceptor groups are sufficiently close so that no fluorescence is detected. However, when the oligonucleotide complexes with the nucleic acid, the donor and acceptor groups are forced to move away from each other, thereby restoring the fluorescence signal. Oligonucleotides that exhibit such a hybridization-dependent fluorescence have been termed "molecular beacons." Molecular beacons may be useful in numerous applications, such as real-time monitoring of hybridization in PCR, in molecular biosensors, on surfaces, in blood, in living cells, and in vivo. Synthesis of double labeled oligonucleotides has been performed with the aid of dye-labeled solid supports and phosphoramidites. In addition, oligonucleotides that bear an amino and an activated thiol group at opposite ends have been synthesized using modified phosphoramidites and solid supports, where chemoselective labeling is performed post-synthetically. However, the known methods for synthesizing double labeled oligonucleotides are restricted to the use of only certain dyes that are available as phosphoramidite, solid support, and chemoselective reagents.

In light of the foregoing, there is a continued need for selectively labeled oligonucleotides, methods for making the oligonucleotides, and compounds useful therefor. The labeled oligonucleotides should provide improved cellular permeation, enhanced free uptake of the oligonucleotide in cell culture studies, and improved protein binding, especially for oligonucleotides containing phosphodiester linkages. In addition, there is a need for methods for producing oligonucleotides selectively labeled at one or more of the 3'-terminal nucleotide, 5'-terminal nucleotide, and internucleotides with one or more different conjugate groups. The methods should also provide for such labeled oligonucleotides without the need for post-synthetic labeling.

SUMMARY OF THE INVENTION

The present invention allows for the selective functionalization of oligonucleotides with conjugate groups. In particular, the oligonucleotides can be selectively functionalized with a first conjugate group at the 3'-terminal nucleotide and optionally functionalized with a second conjugate group at the 5'-terminal nucleotide and/or one or more internucleotides. Alternatively, the oligonucleotides can be selectively functionalized with a first conjugate group at the 5'-terminal nucleotide and optionally functionalized with a second conjugate group at one or more internucleotides. In yet another embodiment, the oligonucleotides can be functionalized with a first conjugate group at one or more internucleotides and with a second conjugate group at one or more different internucleotides.

It is an object of the present invention to provide oligonucleotides having the formula:

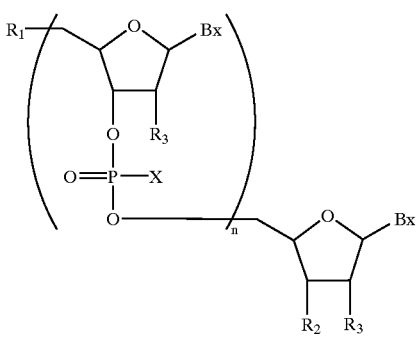

wherein:

$R_1$ is hydroxyl, a protected hydroxyl or a group having the formula:

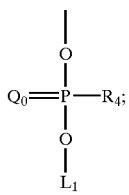

$Q_0$ is O or S;
$R_4$ O$^-$, hydroxyl or a protected hydroxyl;
$R_2$ is hydroxyl, a protected hydroxyl or a group having the formula:

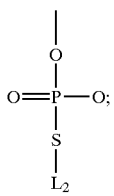

each $R_3$ is H, a 2'-substituent group or a protected 2'-substituent group;
each X is, independently, O$^-$, hydroxyl, protected hydroxyl or —S—$L_3$;
each Bx is an optionally protected heterocyclic base moiety;
n is from 3 to about 50; and
$L_1$, $L_2$ and each of said $L_3$ are, independently, a conjugate group It is a further object of the present invention to provide methods for the preparation of selectively functionalized oligonucleotides having the above formula.

It is yet a further object of the present invention to provide synthetic intermediates useful in such methods.

Other objects will be apparent to those skilled in the art.

BRIEF DESCRIPTION OF THE DRAWINGS

The advantageous features of the invention will be more fully appreciated when considered based on the following detailed description and the attached drawings, wherein.

DETAILED DESCRIPTION OF THE PREFERRED EMBODIMENTS

Figure 1:
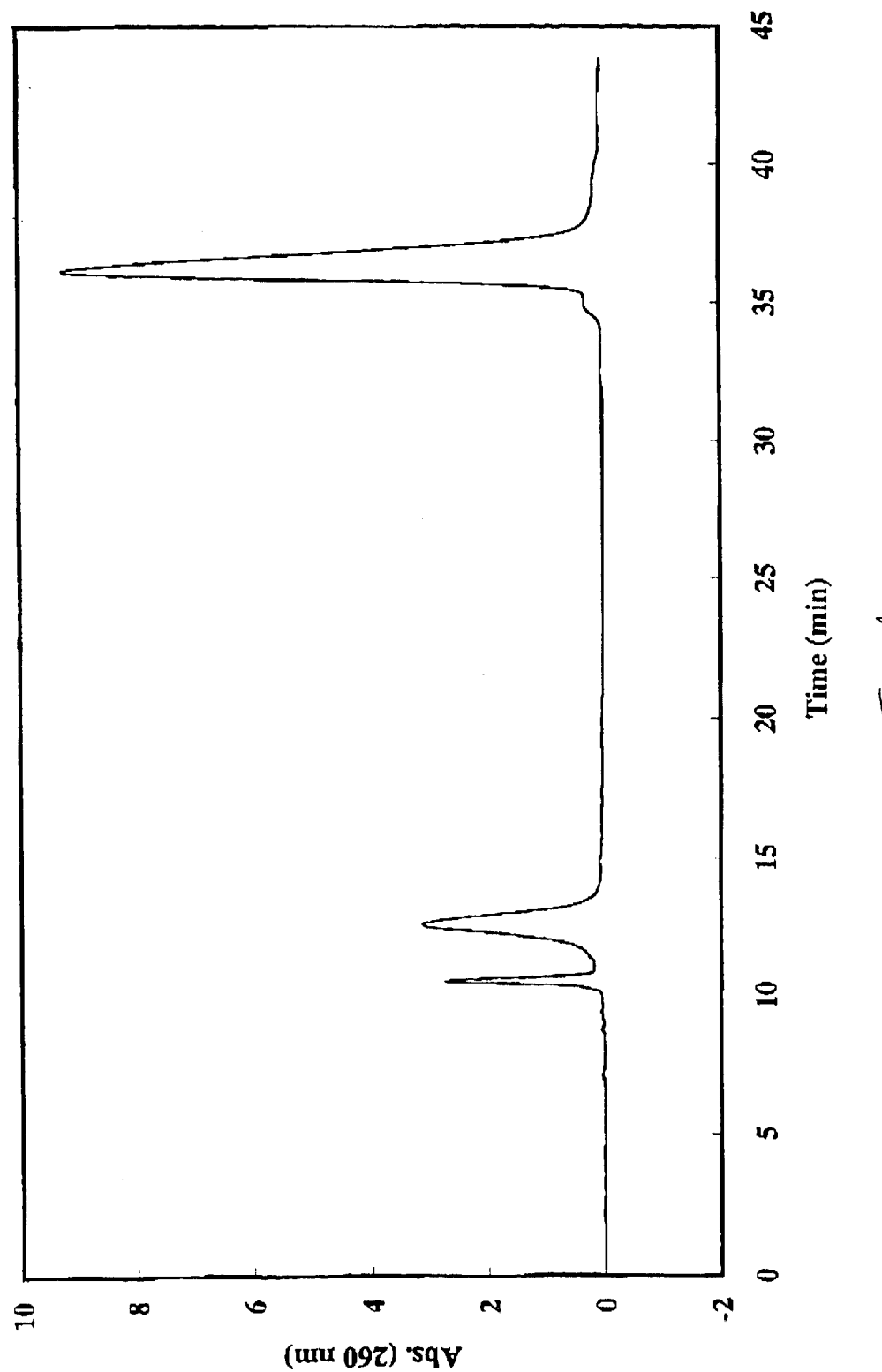
FIG. 1 is an RP HPLC profile of compound 120 in its crude form prior to removal of the DMT group.

The present invention provides methods for preparing compounds that comprise a plurality of linked nucleotides wherein the linked nucleotides are selectively functionalized or labeled with conjugate groups. The compounds can be functionalized at the 3'-terminal nucleotide, at the 5'-terminal nucleotide, at an internucleotide, at the 3'-terminal nucleotide with a first conjugate group and at the 5'-terminal nucleotide with a second conjugate group, at the 3'-terminal nucleotide with a first conjugate group and at one or more internucleotides with a second conjugate group, at the 5'-terminal nucleotide with a first conjugate group and one or more internucleotides with a second conjugate group, or at one or more internucleotides with a first conjugate group and one or more internucleotides with a second conjugate group.

As used herein, "oligomer" and "oligomeric compound" refer to compounds containing a plurality of monomeric subunits that are joined by phosphorus-containing linkages, such as phosphite, phosphodiester, phosphorothioate, and/or phosphorodithioate linkages. Oligomeric compounds therefore include oligonucleotides, their analogs, and synthetic oligonucleotides. The methods of the invention are used for the preparation of oligonucleotides and their analogs.

As used herein, the term "oligonucleotide analog" means compounds that can contain both naturally occurring (i.e. "natural") and non-naturally occurring synthetic moieties, for example, nucleosidic subunits containing modified sugar and/or nucleobase portions. Such oligonucleotide analogs are typically structurally distinguishable from, yet functionally interchangeable with, naturally occurring or synthetic wild type oligonucleotides. Thus, oligonucleotide analogs include all such structures which function effectively to mimic the structure and/or function of a desired RNA or DNA strand, for example, by hybridizing to a target. The term synthetic nucleoside, for the purpose of the present invention, refers to a modified nucleoside. Representative modifications include modification of a heterocyclic base portion of a nucleoside to give a non-naturally occurring nucleobase, a sugar portion of a nucleoside, or both simultaneously.

The present invention relates to processes for preparing an oligonucleotide having the formula:

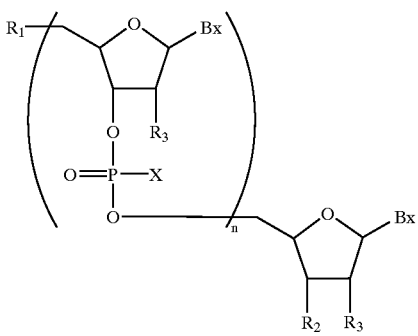

wherein:

R₁ is hydroxyl, a protected hydroxyl or a group having the formula:

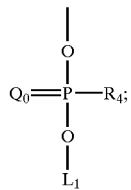

$Q_0$ is O or S;

$R_4$ is O⁻, hydroxyl or protected hydroxyl;

$R_2$ is hydroxyl, a protected hydroxyl or a group having the formula:

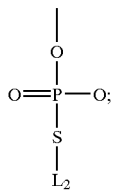

each $R_3$ is H, a 2'-substituent group or a protected 2'-substituent group;

each X is, independently, O or —S—$L_3$;

each Bx is an optionally protected heterocyclic base moiety;

n is from 3 to about 50; and $L_1$, $L_2$ and each of said $L_3$ are, independently, a conjugate group.

In one embodiment, $R_1$ comprises a first conjugate group and $R_2$ optionally comprises a second conjugate group. In another embodiment, $R_1$ comprises a first conjugate group and one or more $R_3$ optionally comprise a second conjugate group. In yet another embodiment, $R_2$ comprises a first conjugate group and one or more $R_3$ optionally comprise a second conjugate group. In still another embodiment, one or more $R_3$ comprise a first conjugate group and one or more $R_3$ optionally comprise a second conjugate group.

Oligonucleotides, or more broadly oligomeric compounds, according to the present invention preferably comprise from about 3 to about 50 nucleosides. It is more preferred that such compounds comprise from about 8 to about 30 nucleosides, with 15 to 25 nucleosides being particularly preferred. When used as "building blocks" in assembling larger oligomeric compounds (i.e., as synthons), smaller oligomeric compounds are preferred. Libraries of dimeric, trimeric, or higher order compounds can be prepared for use as synthons in the methods of the invention. The use of small sequences synthesized via solution phase chemistries in automated synthesis of larger oligonucleotides enhances the coupling efficiency and the purity of the final oligonucleotides. See for example: Miura, K., et al., *Chem. Pharm. Bull.*, 1987, 35, 833–836; Kumar, G., and Poonian, M. S., *J. Org. Chem.*, 1984, 49, 4905–4912; Bannwarth, W., *Helvetica Chimica Acta*, 1985, 68, 1907–1913; Wolter, A., et al., *nucleosides* and *nucleotides*, 1986, 5, 65–77, each of which are hereby incorporated by reference in their entirety.

The attachment of conjugate groups to oligonucleotides and analogs thereof is well documented in the prior art. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, phospholipids, biotin, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, U.S. Pat. No. 5,578,718, issued Jul. 1, 1997, and U.S. Pat. No. 5,218,105. Each of the foregoing is commonly assigned with this application. The entire disclosure of each is incorporated herein by reference.

Preferred conjugate groups amenable to the present invention include lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Lett.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium-1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Other groups for modifying antisense properties include RNA cleaving complexes, pyrenes, metal chelators, porphyrins, alkylators, hybrid intercalator/ligands and photo-crosslinking agents. RNA cleavers include o-phenanthroline/Cu complexes and Ru(bipyridine)$_3^{2+}$ complexes. The Ru(bpy)$_3^{2+}$ complexes interact with nucleic acids and cleave nucleic acids photochemically. Metal chelators are include EDTA, DTPA, and o-phenanthroline. Alkylators include compounds such as iodoacetamide. Porphyrins include porphine, its substituted forms, and metal complexes. Pyrenes include pyrene and other pyrene-based carboxylic acids that could be conjugated using the similar protocols.

Hybrid intercalator/ligands include the photonuclease/intercalator ligand 6-[[[9-[[6-(4-nitrobenzamido)hexyl]amino]acridin-4-yl]carbonyl]amino]hexanoyl-pentaflourophenyl ester. This compound has two noteworthy features: an acridine moiety that is an intercalator and a p-nitro benzamido group that is a photonuclease.

Photo-crosslinking agents include aryl azides such as, for example, N-hydroxysuccin-iimidyl-4-azidobenzoate (HSAB) and N-succinimidyl-6(-4'-azido-2'-nitrophenylamino)hexanoate (SANPAH). Aryl azides conjugated to oligonucleotides effect crosslinking with nucleic acids and proteins upon irradiation, They also crosslink with carrier proteins (such as KLH or BSA), raising antibody against the oligonucleotides.

Vitamins according to the invention generally can be classified as water soluble or lipid soluble. Water soluble vitamins include thiamine, riboflavin, nicotinic acid or niacin, the vitamin $B_6$ pyridoxal group, pantothenic acid, biotin, folic acid, the $B_{12}$ cobamide coenzymes, inositol, choline and ascorbic acid. Lipid soluble vitamins include the vitamin A family, vitamin D, the vitamin E tocopherol family and vitamin K (and phytols). The vitamin A family, including retinoic acid and retinol, are absorbed and transported to target tissues through their interaction with specific proteins such as cytosol retinol-binding protein type II (CRBP-II), retinol-binding protein (RBP), and cellular retinol-binding protein (CRBP). These proteins, which have been found in various parts of the human body, have molecular weights of approximately 15 kD. They have specific interactions with compounds of vitamin-A family, especially, retinoic acid and retinol.

The conjugate groups, $L_1$, $L_2$, and/or $L_3$, are optionally attached to the oligonucleotides of the present invention through a linking group. Suitable linking groups include, but are not limited to, dialkylglycerol linkers. Preferred dialkylglycerol linkers have the structure:

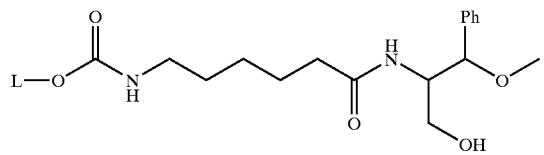

where L is $L_1$, $L_2$, or $L_3$.

As used herein, the term "2'-substituent group" refers to groups that are attached to selected sugar moieties at the 2'-position. However, substituent groups can alternatively be attached to other positions of the sugar moieties (e.g., the 3'- and/or 5'-positions), selected heterocyclic base moieties, or at both the heterocyclic base and the sugar moiety.

A representative list of substituent groups amenable to the present invention include hydrogen, hydroxyl, $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl O-alkynyl, O-alkylamino, O-alkylalkoxy, O-alkylaminoalkyl, O-alkyl imidazole, S-alkyl, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, halogen (particularly fluoro), amino, thiol, keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, aryl, heterocycle, carbocycle, intercalators, reporter groups, conjugates, polyamine, polyamide, poly-alkylene glycol, and polyethers of the formula $(O$-alkyl$)_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et. al. (*Critical Reviews in Therapeutic Drug Carrier Systems* 1992, 9, 249), each of which is herein incorporated by reference in its entirety. Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Additional substituent groups amenable to the present invention include —SR and —NR₂ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.*, 1997, 62, 3415–3420. 2'-NR₂ nucleosides are disclosed by Goettingen, M., *J. Org. Chem.*, 1996, 61, 6273–6281; and Polushin et al., *Tetrahedron Lett.*, 1996, 37, 3227–3230.

Further representative substituent groups can include groups having the structure of one of formula I or II:

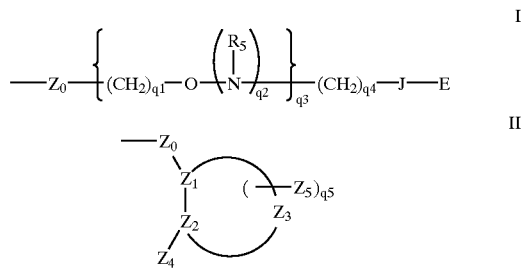

wherein:

$Z_0$ is O, S or NH;

J is a single bond, O or C(=O);

E is $C_1$–$C_{10}$ alkyl, $N(R_5)(R_6)$, $N(R_5)(R_7)$, $N=C(R_5)(R_6)$, $N=C(R_5)(R_7)$ or has one formula III or IV;

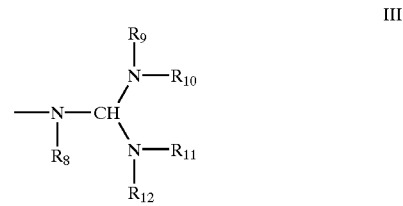

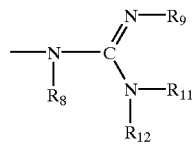

each $R_8$, $R_9$, $R_{10}$, $R_{11}$ and $R_{12}$ is, independently, hydrogen, $C(O)R_{13}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_9$ and $R_{10}$, together form a phthalimido moiety with the nitrogen atom to which they are attached;

or optionally, $R_{11}$ and $R_{12}$, together form a phthalimido moiety with the nitrogen atom to which they are attached;

each $R_{13}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_5$ is T—L,

T is a bond or a linking moiety;

L is a chemical functional group, a conjugate group or a solid support material;

each $R_5$ and $R_6$ is, independently, H, a nitrogen protecting group, substituted or unsubstituted $C_1$–$C_{10}$ alkyl, substituted or unsubstituted $C_2$–$C_{10}$ lo alkenyl, substituted or unsubstituted $C_2$–$C_{10}$ alkynyl, wherein said substitution is $OR_3$, $SR_3$, $NH_3^+$, $N(R_{14})(R_{15})$, guanidino or acyl where said acyl is an acid amide or an ester;

or $R_5$ and $R_6$, together, are a nitrogen protecting group or are joined in a ring structure that optionally includes an additional heteroatom selected from N and O;

or $R_5$, T and L, together, are a chemical functional group;

each $R_{14}$ and $R_{15}$ is, independently, H, $C_1$–$C_{10}$ alkyl, a nitrogen protecting group, or $R_{14}$ and $R_{15}$, together, are a nitrogen protecting group;

or $R_{14}$ and $R_{15}$ are joined in a ring structure that optionally includes an additional heteroatom selected from N and O;

$Z_4$ is OX, SX, or $N(X)_2$;

each X is, independently, H, $C_1$–$C_8$ alkyl, $C_1$–$C_8$ haloalkyl, $C(=NH)N(H)R_{16}$, $C(=O)N(H)R_{16}$ or $OC(=O)N(H)R_{16}$;

$R_{16}$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_5)(R_6)$ $OR_5$, halo, $SR_5$ or CN;

each $q_1$ is, independently, an integer from 1 to 10;

each $q_2$ is, independently, 0 or 1;

q3 is 0 or an integer from 1 to 10;

$q_4$ is an integer from 1 to 10;

q5 is from 0, 1 or 2; and provided that when $q_3$ is 0, $q_4$ is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10.

Some preferred oligomeric compounds of the invention contain, at least one nucleoside having one of the following substituent groups: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O-$CH_2CH_2OCH_3$, also known as 2'-O-(2-methoxyethyl) or 2'-MOE] (Martin et al., *Helv. Chim. Acta*, 1995, 78, 486), i.e., an alkoxyalkoxy group. A further preferred modification is 2'-dimethylaminooxyethoxy, i.e., a $O(CH_2)_2ON(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula III and IV are disclosed in co-owned U.S.

patent application Ser. No. 09/349,040, entitled "Functionalized Oligomers", filed Jul. 7, 1999, hereby incorporated by reference in its entirety.

Representative acetamido substituent groups are disclosed in U.S. patent application Ser. No. 09/378,568, entitled "2'-O-Acetamido Modified Monomers and Oligomers", filed Aug. 19, 1999, hereby incorporated by reference in its entirety.

Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety.

"B" and "Bx," as used herein, is intended to indicate a heterocyclic base moiety. A heterocyclic base moiety (often referred to in the art simply as a "base" or a "nucleobase") amenable to the present invention includes both naturally and non-naturally occurring nucleobases. The heterocyclic base moiety further may be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993.

Certain heterocyclic base moieties are particularly useful for increasing the binding affinity of the oligomeric compounds of the invention to complementary targets. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with selected 2'-sugar modifications such as 2'-methoxyethyl groups.

Representative United States patents that teach the preparation of heterocyclic base moieties (modified nucleobases) include, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned, and each of which is herein incorporated by reference, and commonly owned U.S. patent application Ser. No. 08/762,587, filed on Dec. 10, 1996, also herein incorporated by reference.

The present invention provides oligomeric compounds comprising a plurality of linked nucleosides wherein the preferred internucleoside linkage is a 3',5'-linkage. Alternatively, however, 2',5'-linkages can be used (as described in U.S. application Ser. No. 09/115,043, filed Jul. 14, 1998). A 2',5'-linkage is one that covalently connects the 2'-position of the sugar portion of one nucleotide subunit with the 5'-position of the sugar portion of an adjacent nucleotide subunit.

The compounds described herein may have asymmetric centers. Unless otherwise indicated, all chiral, diastereomeric, and racemic forms are included in the present invention. Geometric isomers may also be present in the compounds described herein, and all such stable isomers are contemplated by the present invention. It will be appreciated that compounds in accordance with the present invention that contain asymmetrically substituted carbon atoms may be isolated in optically active or racemic forms or by synthesis.

The present invention includes all isotopes of atoms occurring in the intermediates or final compounds. Isotopes include those atoms having the same atomic number but different mass numbers. By way of example, and without limitation, isotopes of hydrogen include tritium and deuterium.

In one embodiment, the present invention provides a process for preparing an oligonucleotide having the formula:

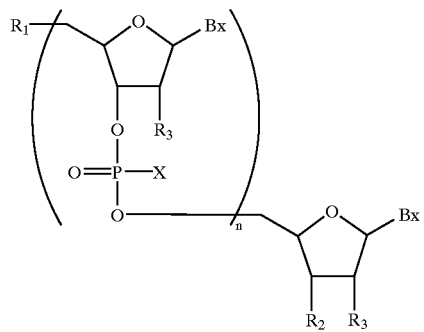

wherein:

$R_1$ is hydroxyl, a protected hydroxyl or a group having the formula:

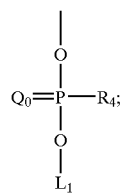

$Q_0$ is O or S;

$R_4$ is O$^-$, hydroxyl, or a protected hydroxyl;

$R_2$ is hydroxyl, a protected hydroxyl or a group having the formula:

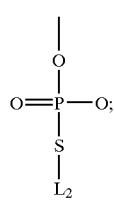

each $R_3$ is H, a 2'-substituent group or a protected 2'-substituent group;

each X is, independently, $O^-$, hydroxyl, protected hydroxyl, or $-S-L_3$;

each Bx is an optionally protected heterocyclic base moiety;

n is from 3 to about 50; and $L_1$, $L_2$ and each of said $L_3$ are, independently, a ligand.

In preferred embodiments, the oligonucleotides have at least two different ligands attached covalently thereto. Further, it is particularly preferred that $L_1$ is different than $L_2$, $L_2$ is different than each of $L_1$ and $L_3$, and each $L_3$ attached at a particular position is different from a second $L_3$ attached at a different position. In addition, said two different ligands covalently attached thereto are preferably positioned to said oligonucleotide at $L_1$ and $L_2$, $L_1$ and $L_3$, $L_2$ and $L_3$, or two of said $L_3$ groups.

The process comprises the steps of:

a) providing a derivatized solid support for oligonucleotide synthesis, said derivatized solid support being derivatized with a group having one of the structures:

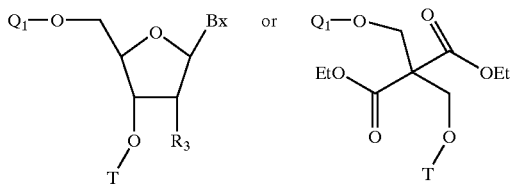

wherein

T is a bifunctional linking moiety linked to the solid support; and $Q_1$ is an acid labile hydroxyl protecting group;

b) treating said solid support with an acidic reagent to deblock said acid labile hydroxyl protecting group to give a free hydroxyl group;

c) reacting said free hydroxyl group with a phosphoramidite composition to form an extended compound, said phosphoramidite composition having the formula:

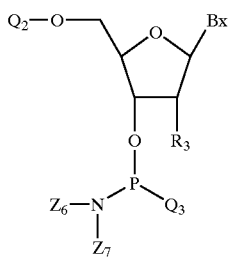

wherein $Q_2$ is a 5'-terminal acid labile hydroxyl protecting group;

$Q_3$ is a phosphorus protecting group; and $Z_6$ and $Z_7$ are, independently, $C_{1-6}$ alkyl;

or $Z_6$ and $Z_7$ are joined together to form a 4- to 7-membered heterocyclic ring system including the nitrogen atom to which $Z_6$ and $Z_7$ are attached, wherein said ring system optionally includes at least one additional heteroatom selected from O, N and S;

d) optionally treating said extended compound with a capping agent to form a capped compound;

e) optionally oxidizing said capped compound to form an oxidized compound;

f) repeating steps b) through e) at least three times to form a further extended compound;

g) optionally treating said further extended compound with an acidic reagent effective to deblock said acid labile hydroxyl protecting group to give a free hydroxyl group and reacting said free hydroxyl group of said further extended compound with a compound of the formula:

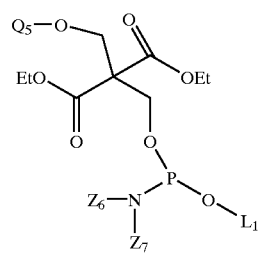

thereby forming a 5'-functionalized further extended compound, wherein $Q_5$ is an acid labile hydroxyl protecting group;

h) treating said further extended compound or said 5'-functionalized further extended compound for a time and under conditions effective to remove at least one phosphorus protecting group giving at least one deblocked phosphorothioate linkage;

i) reacting said deblocked phosphorothioate linkage with a ligand that is reactive with and forms a covalent bond with said deblocked phosphorothioate linkage; and j) optionally repeating steps h) and i) to give said oligonucleotide.

The methods of the present invention are useful for the preparation of all compounds containing phosphorus functionalities. As used herein, functionality includes, but is not limited to phosphite, phosphodiester. phosphorothioate, and/or phosphorodithioate residues, and oligomeric compounds containing monomeric subunits that are joined by a variety of functionality linkages. including phosphite, phosphodiester, phosphorothioate, and/or phosphorodithioate linkages.

The oligomeric compounds in accordance with the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

The reactions of the synthetic methods claimed herein are carried out in suitable solvents which may be readily understood by those skilled in the art of organic synthesis, the suitable solvents generally being an solvent which is substantially nonreactive with the starting materials (reactants), the intermediates. or products at the temperatures at which the reactions are carried out, i.e., temperatures may range from the solvent's freezing temperature to the solvent's boiling temperature. A given reaction may be carried out in one solvent or a mixture of more than one solvent. Depending on the particular reaction step, suitable solvents for a particular reaction step may be selected.

Methods for assembling oligomers in accordance with the present invention include both solution phase and solid phase chemistries. Representative solution phase techniques are described in U.S. Pat. No. 5,210,264, which is assigned to the assignee of the present invention. In preferred embodiments, the methods of the present invention are employed for use in iterative solid phase oligonucleotide synthetic regimes. Representative solid phase techniques are those typically employed for DNA and RNA synthesis utilizing standard phosphoramidite chemistry, (see, e.g., Protocols For Oligonucleotides And Analogs, Agrawal, S., ed., Humana Press, Totowa, N.J., 1993, hereby incorporated by reference in its entirety).

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, hereby incorporated by reference in its entirety), TentaGel Support—an aminopolyethyleneglycol derivatized support (see, e.g., Wright, et al., *Tetrahedron Letters* 1993, 34, 3373, hereby incorporated by reference in its entirety) and Poros—a copolymer of polystyrene/divinylbenzene. 15 In a preferred embodiment, the solid support is derivatized to provide an acid labile trialkoxytrityl group, such as a trimethoxytrityl group (TMT). Without being bound by theory, it is expected that the presence of the trialkoxytrityl protecting group will permit initial detritylation under conditions commonly used on DNA synthesizers. For a faster release of oligonucleotide material in solution with aqueous ammonia, a diglycoate linker is optionally introduced onto the support.

A preferred synthetic solid phase synthesis utilizes phosphoramidites as activated phosphate compounds. In this technique, a phosphoramidite monomer is reacted with a free hydroxyl on the growing oligomer chain to produce an intermediate phosphite compound, which is subsequently oxidized to the $P^V$ state using standard methods. This technique is commonly used for the synthesis of several types of linkages including phosphodiester, phosphorothioate, and phosphorodithioate linkages.

Typically, the first step in such a process is attachment of a first monomer or higher order subunit to a solid support using standard methods and procedures known in the art. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679: and 5,132,418; and Koster U.S. Pat. Nos. 4,725,677 and Re. 34,069. A linker is optionally positioned between the terminal nucleotide and the solid support. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein. F. Ed., IRL Press, N.Y, 1991, Chapter 1, pages 1–23, hereby incorporated by reference in its entirety.

The support-bound monomer or higher order synthon is then treated to remove the protecting group from the free terminal end. Typically, this is accomplished by treatment with acid. The solid support bound monomer, or higher order oligomer, is then reacted with individual monomeric or higher order building blocks (i.e., synthons) to form a compound which has a phosphite or thiophosphite linkage. In preferred embodiments, the synthons reacted under anhydrous conditions in the presence of an activating agent such as, for example, 1H-tetrazole, 5-(4-nitrophenyl)-1H-tetrazole or diisopropylamino tetrazolide.

In one preferred embodiment, the oligonucleotides are assembled according to the method described in U.S. Pat. No. 6,121,437, which is hereby incorporated by reference in its entirety. Accordingly, the phosphite groups of internucleosidic nucleotides that are to be functionalized are protected with derivatives of 2-benzamidoethyl groups. In particular, the oligonucleotides are formed by reacting a compound of Formula V:

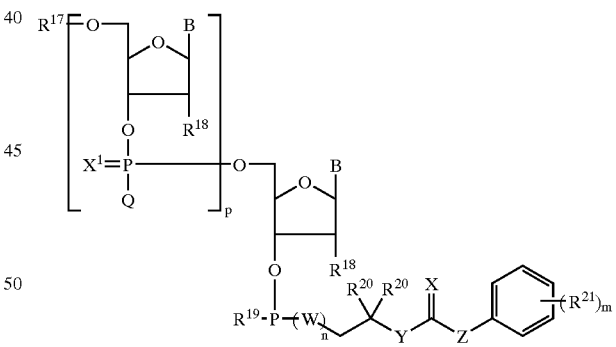

V wherein:
W is selected independently from O and S;
X is selected independently from O and S;
Y is selected independently from O and $NR^{22}$;
Z is selected independently from a single bond, O, and $NR^{22}$;
$R^{21}$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^{23}$, $NR^{24}R^{25}$, and phenyl;
alternatively, two $R^{21}$ groups, when on adjacent carbons of the phenyl ring, join to form a napthyl ring that includes said phenyl ring;

$R^{22}$, at each occurrence, is selected independently from H, $C_{1-6}$ alkyl, $C_{2-6}$ alkenyl, $C_{2-6}$ alkynyl, $C_{3-6}$ cycloalkyl, and phenyl;

$R^{20}$, at each occurrence, is selected independently from hydrogen, $C_{1-6}$ alkyl, $C_{2-6}$ alkenyl, $C_{2-6}$ alkynyl, $C_{3-6}$ cycloalkyl, and phenyl;

$R^{23}$ is selected independently from $C_{1-6}$ alkyl, $C_{3-6}$ cycloalkyl, and phenyl;

$R^{24}$ and $R^{25}$, at each occurrence, are selected independently from $C_{1-6}$ alkyl, $C_{3-6}$ cycloalkyl, and phenyl;

n is selected independently from 0, 1, 2, and 3; and m is selected independently from 0, 1, 2, and 3;

$R^{17}$, at each occurrence, is selected independently from H, a hydroxyl protecting group, and a linker connected to a solid support;

$R^{18}$, at each occurrence, is independently H, hydroxyl, $C_{1-20}$ alkyl, $C_{3-20}$ alkenyl, $C_{2-20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, or one of formula VI or VII:

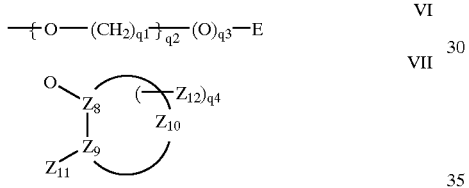

wherein

E is selected from $C_{1-10}$ alkyl, $N(R^{26})(R^{27})$ and $N=C(R^{26})(R^{27})$;

$R^{26}$ and $R^{27}$ are independently selected from H, $C_{1-10}$ alkyl, dialkylaminoalkyl, a nitrogen protecting group, a tethered or untethered conjugate group, a linker to a solid support, or alternatively $R^{26}$ and $R^{27}$, together, are joined in a nitrogen protecting group or a ring structure that can include at least one additional heteroatom selected from N and O;

$q^1$ is from 1 to 10;

$q^2$ is from 1 to 10;

$q^3$ is 0 or 1;

$Z_{11}$ is $OR^{28}$, $SR^{28}$, or $N(R^{28})_2$;

$R^{28}$ is selected independently from H, $C_1$–$C_8$ alkyl, $C_1$–$C_8$ haloalkyl, $C(=NH)N(H)R^{29}$, $C(=O)N(H)R^{29}$ and $OC(=O)N(H)R^{29}$;

$R^{29}$ is H or $C_1$–$C_8$ alkyl;

$Z_8$, $Z_9$ and $Z_{10}$ comprise a ring system having from about 4 to about 7 carbon atoms or having from about 3 to about 6 carbon atoms and 1 or 2 heteroatonms wherein said heteroatoms are selected from oxygen, nitrogen and sulfur and wherein said ring system is aliphatic, unsaturated aliphatic, aromatic, or saturated or unsaturated heterocyclic;

$Z_{11}$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R^{26})(R^{27})OR^{26}$, halo, $SR^{26}$ or CN; and $q^4$ is, 0, 1 or 2;

$R^{19}$ is selected independently from $NR^{30}R^{31}$, and a 5–6 membered heterocyclic system containing 1–4 heteroatoms selected independently from N, O, and S;

$R^{30}$ and $R^{31}$, at each occurrence, are selected independently from $C_{1-10}$ alkyl, $C_{3-7}$ cycloalkyl, and isopropyl;

$X^1$ is selected independently from O and S;

B, at each occurrence, is independently selected from a protected or unprotected naturally occurring nucleobase, and a protected or unprotected non-naturally occurring nucleobase;

q is selected independently from 1, 2, 3, 4, 5, 6, 7, 8, 9, and 10;

p is an integer selected independently from 0 to about 50;

Q, at each occurrence, is selected independently from OH, SH, and

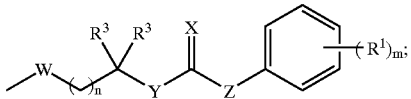

with a compound of the following formula:

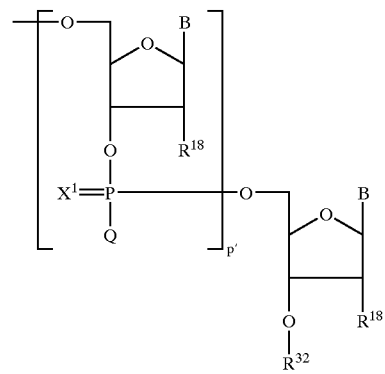

wherein:

$R^{32}$ is selected independently from a hydroxyl protecting group, and a linker connected to a solid support; and p' is an integer selected independently from 0 to about 50.

In another embodiment, the oligonucleotides are assembled from building blocks having the formula VIII:

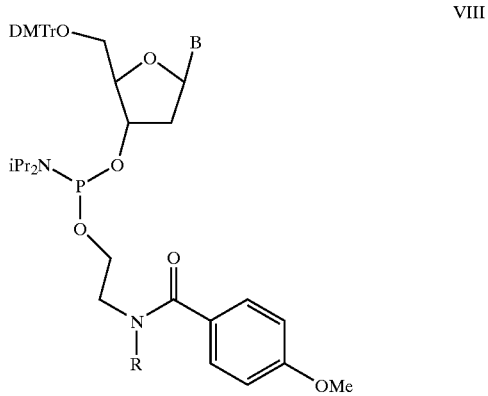

wherein:

DMTr is a 4,4'-dimethoxytrityl group;

iPr is an isopropyl group;

R is hydrogen or an isopropyl group; and

B is a heterocyclic base.

Treatment with an acid replaces the hydroxyl protecting group at the unbound terminus of the oligonucleotide, and thus enables the solid support bound oligomer to participate in the next synthetic iteration. This process is repeated until an oligomer of desired length is produced.

As will be appreciated, one or more of the 2'-, 3'-, and/or 5'-positions of the oligonucleotide comprises a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, *Protective Groups in Organic Synthesis*, Chapter 2, 2d ed, John Wiley & Sons, New York, 1991, each of which are hereby incorporated by reference in their entirety. Preferred protecting groups include trimethoxytrityl, dimethoxytrityl (DMT), monomethoxytrityl, 9-phenylxanthen-9-yl (Pixyl) and 9-(p-methoxyphenyl)xanthen-9-yl (Mox).

The protecting group can be removed from oligomeric compounds of the invention by techniques well known in the art to form the free hydroxyl. A wide variety of bases can be used to initiate the removal of protecting groups. These bases include aqueous ammonium hydroxide, aqueous methylamine, DBU (1,8-diazabicyclo[5.4.0]undec-7-ene) and carbonates containing counterions such as lithium, potassium, sodium, and cesium. Most preferred is potassium carbonate and ammonia. Removal of the protecting groups may be performed in a variety of suitable solvents. These solvents include those known to be suitable for protecting group removal in oligonucleotide synthesis. In the case of ammonia, water is the preferred solvent, whereas when using carbonates, alcohols are preferred. Methanol is most preferred. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra. In addition, treatment of the oligonucleotide with ammonium hydroxide at room temperature for about 48 hours can be used to remove isopropyl substituted benzamidoethyl and cyanoethoxy protecting groups. The NH analogs of benzamidoethyl protecting groups, however, can be removed by treating the oligonucleotide with ammonium hydroxide at about 55° C. for about 48 hours. Further, allyl protecting groups require the use of paladium zero and silyl protecting groups can be removed by fluoro. In certain preferred embodiments, conditions for removal of the oxygen or sulfur protecting group also effect cleavage of the oligomeric compound from the solid support. The deprotected terminal nucleotide and/or internucleosidic nucleotides can then be functionalized.

In some embodiments, phosphite or thiophosphite compounds are oxidized or sulfurized. The choice of oxidizing or sulfurizing agent will determine whether the linkage will be oxidized or sulfurized to a phosphotriester, thiophosphotriester, or a dithiophosphotriester linkage. Sulfurizing agents used during oxidation to form phosphorothioate and phosphorodithioate linkages include Beaucage reagent (see e.g. Iyer, R. P., et. al., *J. Chem. Soc.*, 1990, 112, 1253–1254, and Iyer, R. P., et. al., *J. Org. Chem.*, 1990, 55, 4693–4699); tetraethylthiuram disulfide (see e.g., Vu, H., Hirschbein, B. L., *Tetrahedron Lett.*, 1991, 32, 3005–3008); dibenzoyl tetrasulfide (see e.g., Rao, M. V., et. al., *Tetrahedron Lett.*, 1992, 33, 4839–4842); di(phenylacetyl)disulfide (see e.g., Kamer, P. C. J., *Tetrahedron Lett.*, 1989, 30, 6757–6760); Bis(O,O-diisopropoxy phosphinothioyl) disulfids (see Stec et al., *Tetrahedron Lett.*, 1993, 34, 5317–5320); 3-ethoxy-1,2,4-dithiazoline-5-one (see *Nucleic Acids Research*, 1996 24, 1602–1607, and *Nucleic Acids Research*, 1996 24, 3643–3644); Bis(p-chlorobenzenesulfonyl)disulfide (see *Nucleic Acids Research*, 1995 23, 4029–4033); sulfur, sulfur in combination with ligands like triaryl, trialkyl, triaralkyl, or trialkaryl phosphines. The foregoing references are hereby incorporated by reference in their entirety.

Suitable oxidizing agents for forming the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

As used herein, the terms "phosphorus protecting group" and "phosphorus blocking group" refers to a group that is initially bound to the phosphorus atom of a phosphoramidite. The phosphorus blocking group functions to protect the phosphorus containing internucleotide linkage or linkages during, for example, solid phase oligonucleotide synthetic regimes. Treatment of the internucleotide linkage or linkages that have a phosphorus blocking group thereon with a deblocking agent, such as aqueous ammonium hydroxide, will result in the removal of the phosphorus blocking group and leave a hydroxyl or thiol group in its place.

There are many phosphorus blocking groups known in the art which are useful in the present invention including, but not limited, to, cyanoethyl, diphenylsilylethyl, cyanobutenyl, cyano p-xylyl (CPX), methyl-N-trifluoroacetyl ethyl (META) and acetoxy phenoxy ethyl (APOE) groups. Phosphorus protecting groups are further described in Beaucage, S. L. and Iyer, R. P., *Tetrahedron*, 1993, 49, 1925–1963; Beaucage, S. L. and Iyer, R. P., *Tetrahedron*, 1993, 49, 10441–10488; and Beaucage, S. L. and Iyer, R. P., *Tetrahedron*, 1992, 48, 2223–2311. Representative United States patents that teach the preparation of phosphorus protecting groups and their incorporation into phosphoramidite compounds include, but are not limited to, U.S. Pat. Nos. 5,783,690; 5,760,209; 5,705,621; 5,614,621; 5,453,496; 5,153,319; 5,132,418; 4,973,679; 4,725,677; 4,668,777; 4,500,707; 4,458,066; 4,415,732; and Re. 34,069, the entire contents of each of which are herein incorporated by reference.

As will be recognized, the steps of certain processes of the present invention need not be performed any particular number of times or in any particular sequence. Additional objects, advantages, and novel features of this invention will become apparent to those skilled in the art upon examination of the following synthetic teachings and working examples which are intended to be illustrative of the present invention, and not limiting thereof.

EXAMPLES

As described in detail below, for the introduction of a labeled 5'-terminal phosphate or thiophosphate, phosphoramidites, 2 and 3 bearing pyrene or fluorescein reporter groups, respectively, were synthesized (Scheme 1, below). Similarly, phosphoramidite 4 (reference sample) and phosphoramidites 5–7 for 5'-terminal phosphorylation were obtained. The phosphoramidites 2–6 were incorporated in a standard manner at the last step of oligonucleotide synthesis (Scheme 3). The solid support bound oligonucleotides were deprotected with concentrated ammonium hydroxide to give crude 8–15. On isolation, these were detritylated with diluted AcOH to give 16–23. Brief treatment with a base removed the 5'-terminal 3-hydroxy-2,2-bis(ethoxycarbonyl) prppyl-1 phosphate protecting group to afford 24–31. The final products, 5'-phosphorylated 24 and 25 and 5'-labeled 26–31 were desalted by HPLC. All intermediates and final products were characterized by ESMS and HPLC (Tables 1 and 2, below).

For the introduction of 3'-terminal phosphate or thiophosphate, solid support 32 was synthesized (Scheme 2, below). The utility of 32 was verified in preparation of oligonucleotides 33–38 (Scheme 4 and Table 3, below). Oligonucleotide 32 demonstrated favorable properties in two respects. First, the TMT protecting group in 32 was removed with 3% $Cl_2HCCO_2H$ in $CH_2Cl_2$, i.e. under milder conditions than the previously used for the removal of DMT group (3% $F_2CCO_2H$ in $CH_2Cl_2$). Second, the diglycolyl linker in 32 was cleaved with aqueous bases faster than previously reported for the malonyl linker.

The reactivity of the 3'-terminal phosphorothioate group was verified by labeling 37 with N-(1-pyrenylmethyl) iodoacetamide and 5-iodoacetamidofluorescein to afford 39 and 40 (Scheme 5 and Table 3, below).

The preparation of oligonucleotides labeled with two different fluorescent reporter groups at the 5'- and 3'-termini was accomplished according to Schemes 6 and 7. First, protected oligonucleotides 41a and 41b were assembled on solid support 32. For the last coupling, 5'-O-(4,4'-dimethoxytrityl)-3'-O-(N,N-diisopropylamino) [2-(4-methoxybenzamido)ethoxy]phosphinyl-2'-deoxythymidine was used. For the first and the last coupling cycles, sulfurization with 3H-1,2-benzodithiol-3-one 1,1-dioxide was carried out while all other cycles employed oxidation with t-BuOOH in MeCN. Thus, the oligonucleotides synthesized contained the 3'-terminal phosphorothioate and a 2-(4-methoxybenzamido)ethyl protected P=S linkage preceding the 5'-teminal nucleoside residue. After deprotection with ammonium hydroxide (2 days/RT), 42 was obtained and isolated by HPLC (Table 4). On detritylation, 42 gave 43, which was reacted with 44 to give 45. Deprotection of 45 with concentrated ammonium hydroxide for 48 h at 55° C. removed 2-(4-methoxybenzamido)ethyl protection to give 46 which contained the second phosphorothioate group for the conjugation. Compound 46 was next labeled with 44 and 47–49 to give a bis-pyrenyl labeled 50 and unsymmetrically labeled 51–53 (Scheme 7 and Table 4). The methodology described above allows one to place the second reporter group in any internucleosidic position of the oligonucleotide.

The methodology described above was also used to label 5'- and 3'-terminal phosphorothioate residues with two different reporter groups. First, solid support-bound oligonucleotides 54a and b bearing the selectively protected 5'-terminal phosphorothioate group were synthesized on solid support 32 as depicted in Scheme 8. These were treated with ammonium hydroxide for 2 days at RT to give 55 where only the 3'-teminal phosphorothioate group was deprotected. Compound 55 was next labeled with 49. The product was isolated by HPLC, and 2-(4-methoxybenzamido)ethyl protection was removed with concentrated ammonium hydroxide for 48 h at 55° C. Without isolation, the product was detritylated and briefly treated with a base, which removed diethyl 3-hydroxy-bis-(ethoxycarbonyl)propyl protection from the 5'-terminal phosphorothioate group to give 56. This was treated with labeling reagents 44, 48, and 49, and the unsymmetrically bis-labeled oligonucleotides 57–59 were isolated by HPLC and characterized (Scheme 9 and Table 5, below).

Example 1

Diethyl 2-[(4,4',4"-trimethoxytrityl)oxymethyl]-2-hydroxymethylmalonate (1)

Referring to scheme 1, diethyl bis-(hydroxymethyl) malonate (11.5 g, 55 mmol) was treated overnight with 4,4',4"-trimethoxytrityl chloride (19.2 g, 52 mmol) in pyridine (16 mL) and dioxane (100 mL), and the solvent was evaporated. The residue was dissolved in $CH_2Cl_2$ (500 mL), washed with 5% aqueous $NaHCO_3$ (3×100 mL), washed with brine (2×100 mL), dried over $Na_2SO_4$ and evaporated. The residue was purified on a silica gel column using a step gradient of ethyl acetate (0 to 15%) in toluene to give 1 (8.2 g, 67.5%) as an oil. HR MALDI MS: calculated for $C_{31}H_{36}O_9$ (M+H$^+$) 553.2442, found 553.2438. $^1$H NMR (CDCl$_3$) δ 7.29 (6H, d, J=8.8 Hz), 6.83 (6H, d, J=8.8 Hz), 4.26–4.11 (6H, m), 3.80 (9H, s), 3.62 (2H, s), 2.11 (1H, t, J=5.8 Hz), 1.24 (6H, t, J=7.0 Hz). $^{13}$C NMR (CDCl$_3$) δ 169.3 (C), 158.5 (C), 136.1 (C), 129.8 (CH), 113.2 (CH), 86.0 (C), 63.7 (CH$_2$), 61.9 (CH$_2$), 61.6 (CH$_2$), 60.6 (C), 55.2 (CH$_3$), 14.1 (CH$_3$).

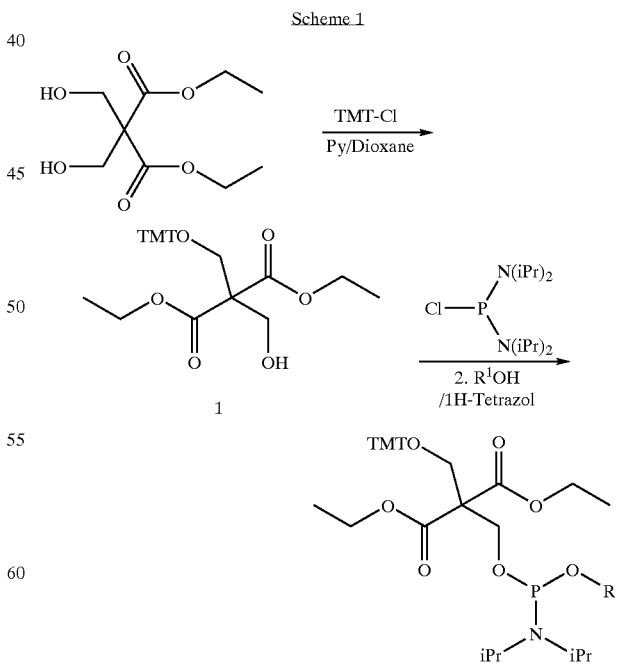

Scheme 1

2-7

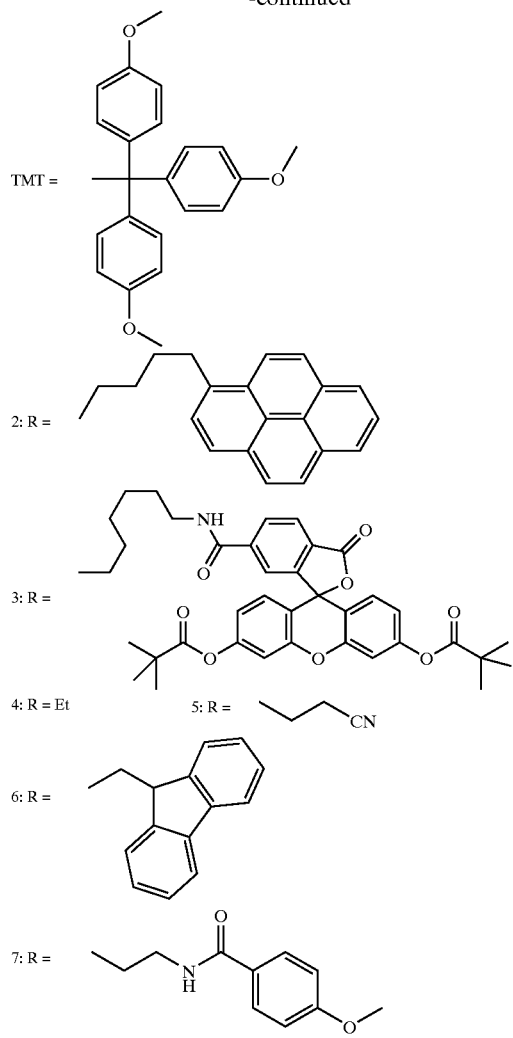

Example 2
Diethyl[[[tris(4-methoxyphenyl)methyl]oxy]methyl][[[[bis(1-methylethyl)amino][6-[[3',6'-bis(2,2-dimethylpropionyloxy)-3-oxospiro[isobenzofuran-1(3H),9'-[9H]xanthen]-5-yl]carboxamido]hexloxy]phosphino]oxy]mrthyl]propanedioate (3).

A solution of chloro bis[(N,N,-diisopropyl)amino]phosphite (768 mg, 2.88 mmol) in dry CH$_2$Cl$_2$ (10 mL) was added dropwise to a mixture of 1 (1381 mg, 2.5 mmol) and N-ethyl-N,N-diisopropylamine (485 mg, 3.75 mmol) in dry CH$_2$Cl$_2$ (10 mL) under magnetic stirring at −30° C. The reaction mixture was allowed to warm up to room temperature, and the stirring was continued for 1 h. 6-[[3',6'-bi(2,2-dimethylpropionyloxy)-3-oxospiro[isobenzofuran-1(3H),9'-[9H]xanthen]-5-yl]carboxamido]hexanol (1030 mg, 1.6 mmol) was added followed by 1H-tetrazole (0.45 M in MeCN; 2.8 mL, 1.25 mmol). The resulting mixture was kept at room temperature for 2 h. Aqueous NaHCO$_3$ (5%; 5 mL) was added, the emulsion was diluted with brine (25 mL), and the product was extracted with ethyl acetate (3×50 mL). Extracts were washed with brine (3×25 mL), dried over Na$_2$SO$_4$, and evaporated. The residue was dissolved in toluene (50 mL), applied on a silica gel column, and separated eluting with a gradient from 5:91:4 to 40:56:4 ethyl acetate/hexane/triethylamine. Collected fractions were evaporated, co-evaporated with dry MeCN (3×50 mL), dry toluene (3×50 mL), and dried on an oil pump to give 3 (1400 mg, 66.0%) as a yellow foam. HR FAB MS: found m/z 1324.5850; C$_{74}$H$_{89}$N$_2$O$_{18}$P requires 1324.5848. $^1$H NMR (CDCl$_3$) δ 8.06 (1H, dd, J=1.3, 7.9 Hz), 8.04 (1H, dd, J=1.3, 7.9 Hz), 7.57 (1H, dd, J=1.3 and 1.4 Hz), 7.25–7.19 (6H, m), 7.11 (1H, d, J=1.4 Hz), 7.10 (1H, d, J=1.4 Hz), 7.02 (1H, t, J=5.8 Hz), 6.93–6.89 (2H, m), 6.84 (1H, dd, J=0.9 and 2.3 Hz), 6.82–6.78 (7H, m), 4.22 (1H, dd, J=5.7 and 9.7 Hz), 4.16–3.97 (7H, m), 3.71 (9H, s), 3.54 (1H, d, J=8.5 Hz), 3.51 (1H, d, J=8.5 Hz), 3.52–3.41 (2H, m), 3.23–3.16 (2H, m), 1.50–1.36 (4H, m), 1.32 (18H, s), 1.32–1.20 (4H, m), 1.12 (3H, t, J=7.1 Hz), 1.11 (3H, t, J=7.0 Hz), 1.08 (6H, d, J=6.8 Hz), 1.03 (6H, d, J=6.6 Hz). $^{13}$C NMR (CDCl$_3$) δ 177.5 (C), 169.2 (C), 169.12 (C), 169.09 (C), 166.1 (C), 159.5 (C), 154.0 (C), 152.4 (C), 143.0 (C), 137.2 (C), 130.7 (CH), 130.4 (CH), 130.3 (CH), 128.8 (C), 126.2 (CH), 123.4 (CH), 119.2 (CH), 118.3 (CH), 117.0 (C), 113.9 (CH), 111.4 (CH), 86.5 (C), 82.5 (C), 64.0 (CH$_2$), 62.6 (CH$_2$), 62.3 (CH$_2$), 62.2 (CH$_2$), 61.7 (CH$_2$), 60.7 (C), 55.8 (CH$_3$), 43.7 (CH), 43.6 (CH), 40.7 (CH$_2$), 39.8 (C), 31.8 (CH$_2$), 29.9 (CH$_2$), 27.3 (CH$_2$), 27.2 (CH$_3$), 26.4 (CH$_2$), 25.0 (CH$_3$), 24.9 (CH$_3$), 24.8 (CH$_3$), 14.3 (CH$_3$). $^{31}$P NMR (CDCl$_3$) δ 147.4.

Example 3
Diethyl[[[bis(4-methoxyphenyl)phenylmethyl]oxy]methyl][[[[bis(1-methylethyl)amino][6-[[3',6'-bis(2,2-dimethylpropionyloxy)-3-oxospiro[isobenzofuran-1(3H),9'-[9H]xanthen]-5-yl]carboxamido]hexyloxy]phosphino]oxy]methyl]propanedioate (3a)

Compound 3a was prepared analogously from diethyl 2-[[[bis(4-methoxyphenyl)phenylmethyl]oxy]methyl]-2-hydroxymethylpropanedioate 1a (829 mg, 1.5 mmol), chloro bis[(N,N,-diisopropyl)amino]phosphite (440 mg, 1.65 mmol), and 6-[[3',6'-bi(2,2-dimethylpropionyloxy)-3-oxospiro[isobenzofuran-1(3H),9'-[9H]xanthen]-5-yl]carboxamido]hexanol (483 mg, 0.5 mmol). Isolation on a silica gel column using gradient from 5:93:2 to 40:58:2 ethyl acetate/hexane/triethylamine gave 3a (798 mg, 82.1%) as a yellow foam. HR FAB MS: found m/z 1294.5742; C$_{73}$H$_{87}$N$_2$O$_{17}$P requires 1294.5742. $^1$H NMR (CDCl$_3$) δ 8.10 (1H, dd, J=1.3 and 7.9 Hz), 8.02 (1H, dd, J=1.3 and 7.9 Hz), 7.54 (1H, dd, J=1.3 and 1.4 Hz), 7.45–7.15 (9H, m), 7.11 (1H, d, J=1.4 Hz), 7.08 (1H, d, J=1.4 Hz), 7.02 (1H, t, J=5.8 Hz), 6.92–6.87 (2H, m), 6.82–6.78 (6H, m), 4.20 (1H, dd, J=5.7 and 9.7 Hz), 4.16–3.95 (7H, m), 3.78 (6H, s), 3.58 (1H, d, J=8.5 Hz), 3.50 (1H, d, J=8.5 Hz), 3.51–3.41 (2H, m), 3.24–3.16 (2H, m), 1.52–1.36 (4H, m), 1.34 (18H, s), 1.32–1.20 (4H, m), 1.12 (3H, t, J=7.0 Hz), 1.11 (3H, t, J=6.9 Hz), 1.07 (6H, d, J=6.7 Hz), 1.00 (6H, d, J=6.7 Hz). $^{13}$C NMR (CDCl$_3$) δ 176.6 (C), 168.5 (C), 168.4 (C), 165.5 (C), 158.4 (C), 153.4 (C), 152.8 (C), 151.5 (C), 144.8 (C), 141.6 (C), 135.9 (C), 130.2 (CH), 129.3 (CH), 129.0 (CH), 128.3 (CH), 127.7 (CH), 126.7 (CH), 125.5 (CH), 122.4 (CH), 117.9 (CH), 115.6 (C), 113.0 (CH), 110.5 (CH), 85.8 (C), 81.9 (C), 63.3, 63.0 (CH$_2$), 62.0, 61.7 (CH$_2$), 61.2 (CH$_2$), 60.9 (CH$_2$), 60.0, 59.9 (C), 55.2 (CH$_3$), 43.0, 42.8 (CH), 40.4 (CH$_2$), 39.2 (CH$_2$), 31.1, 31.0 (CH$_2$), 29.3 (CH$_2$), 27.1 (CH$_3$), 26.6 (CH$_2$), 25.6 (CH$_2$), 24.6, 24.5 (CH$_3$), 14.1 (CH$_3$). $^{31}$P NMR (CDCl$_3$) δ 146.9.

Example 4
Diethyl[[[tris(4-methoxyphenyl)methyl]oxy]methyl][[[[bis(1-methylethyl)amino][4-(1-pyrenebutyl)oxy]phosphino]oxy]methyl]propanedioate (2).

Compound 2 was prepared from 1 (1630 mg, 2.95 mmol), chloro bis[(N,N,-diisopropyl)amino]phosphite (944 mg, 3.54 mmol), and 4-(1-pyrene)butanol (1015 mg, 3.7 mmol) as described for 3. Isolation on a silica gel column using gradient from 5:91:4 to 40:56:4 ethyl acetate/hexane/triethylamine gave 2 (2185 mg, 77.5%) as a white foam. HR FAB MS: found m/z 955.4421; C$_{57}$H$_{67}$NO$_{10}$P requires 955.4424. $^1$H NMR (CDCl$_3$) δ 8.24 (1H, d, J=9.2 Hz), 8.12 (2H, d, J=7.5 Hz), 8.07–7.93 (5H, m), 7.80 (1H, d, J=7.9 Hz), 7.31–7.25 (6H, m), 6.78–6.72 (6H, m), 4.37 (1H, dd, J=5.8 and 9.8 Hz), 4.26 (1H, dd, J=3.8 and 9.8 Hz), 4.21–4.01 (4H, m), 3.71 (2H, s), 3.74–3.43 (4H, m), 3.66 (9H, s), 3.30 (2H, t, J=7.7 Hz), 2.0–1.86 (2H, m), 1.75–1.68 (2H, m), 1.14 (3H, t, J=7.2 Hz), 1.13 (3H, t, J=7.0 Hz), 1.11 (6H, d, J=6.4 Hz), 1.07 (6H, d, J=6.6 Hz). $^{13}$C NMR (CDCl$_3$) δ 168.4 (C), 168.3 (C), 158.2 (C), 137.0 (C), 136.4 (C), 131.4 (C), 130.9 (C), 129.9 (CH), 128.6 (C), 127.5 (CH), 127.2 (CH), 127.1 (CH), 126.4 (CH), 125.7 (CH), 125.1 (C), 125.0 (CH), 124.8 (CH), 124.7 (CH), 124.6 (CH), 123.5 (CH), 112.9 (CH), 85.5 (C), 63.2 (CH$_2$), 61.8 (CH$_2$), 61.1 (CH$_2$), 60.9 (CH$_2$), 60.0 (CH$_2$), 59.9 (C), 55.0 (CH$_3$), 43.0 (CH), 42.8 (CH), 33.1 (CH$_2$), 31.3 (CH$_2$), 28.2 (CH$_2$), 24.5 (CH$_3$), 24.4 (CH$_3$), 13.9 (CH$_3$). $^{31}$P NMR (CDCl$_3$) δ 150.0.

Example 5

Diethyl[[[tris(4-methoxyphenyl)methyl]oxy]methyl][[[bis(1-methylethyl)amino](ethoxy)phosphino]oxy]methyl]propanedioate (4).

Compound 4 was prepared from 1 (553 mg, 1.0 mmol), chloro bis[(N,N,-diisopropyl)amino]phosphite (307 mg, 1.15 mmol), and ethanol (69 mg, 1.5 mmol) as described for 3. Isolation on a silica gel column using gradient from 5:93:2 to 40:58:2 ethyl acetate/hexane/triethylamine gave 4 (662 mg, 91%) as a colorless oil. HR FAB MS: found m/z 727.3486; C$_{39}$H$_{54}$NO$_{10}$P requires 727.3485. $^1$H NMR (CDCl$_3$) δ 7.40–7.27 (6H, m), 6.92–6.67 (6H, m), 4.37 (1H, dd, J=5.8 and 7.5 Hz), 4.26–4.02 (5H, m), 3.77 (9H, s), 3.68 (2H, s), 3.75–3.39 (2H, m), 3.20 (2H, m), 1.40–1.00 (21H, m). $^{13}$C NMR (CDCl$_3$) δ 168.6 (C), 168.4 (C), 158.3 (C), 136.5 (C), 130.0 (CH), 113.0 (CH), 85.6 (C), 63.7 (CH$_2$), 61.6 (CH$_2$), 61.3 (CH$_2$), 60.9 (CH$_2$), 60.0 (CH$_2$), 58.9 (C), 55.2 (CH$_3$), 43.0 (CH), 42.8 (CH), 24.6 (CH$_3$), 24.4 (CH$_3$), 19.1 (CH$_3$), 14.0 (CH$_3$). $^{31}$P NMR (CDCl$_3$) δ 145.6.

Example

Diethyl[[[tris(4-methoxyphenyl)methyl]oxy]methyl][[[bis(1-methylethyl)amino][2-(4-methoxybenzamido)ethoxyl]phosphino]methyl]propanedioate (5).

Compound 5 was prepared from 1 (553 mg, 1.0 mmol), chloro bis[(N,N,-diisopropyl)amino]phosphite (307 mg, 1.15 mmol), and 2-(4-methoxybenzamido)ethanol (254 mg, 1.3 mmol) as described for 3. Isolation on a silica gel column using gradient from 0:95:5 to 40:55:5 ethyl acetate/hexane/triethylamine gave 5 (652 mg, 74.4%) as a colorless oil. HR FAB MS: found m/z 876.3963; C$_{47}$H$_{61}$N$_2$O$_{12}$P requires 876.3962. $^1$H NMR (CDCl$_3$) δ 7.8–7.65 (2H, m); 7.40–7.27 (7H, m), 6.92–6.67 (8H, m), 4.3–4.0 (6H, m), 3.81 (3H, s); 3.77 (9H, s), 3.7–3.3 (8H, m), 1.40–1.00 (18H, m). $^{13}$C NMR (CDCl$_3$) δ 168.6 (C), 168.4 (C), 168.1 (C), 162.1 (C), 158.0 (C), 136.3 (C), 130.2 (CH), 128.8 (CH), 126.4 (C), 117.5 (C), 113.7 (CH), 113.1 (CH), 85.6 (C), 63.7, 63.4 (CH$_2$), 62.6, 62.2 (CH$_2$), 62.1, 61.9 (CH$_2$), 61.4 (CH$_2$), 61.3 (C), 55.3 (CH$_3$), 55.1 (CH$_3$), 43.1 (CH), 42.9 (CH), 40.9 (CH$_2$), 24.6 (CH$_3$), 24.4 (CH$_3$), 14.2 (CH$_3$). $^{31}$P NMR (CDCl$_3$) δ 147.9.

Example 6

Diethyl[[[tris(4-methoxyphenyl)methyl]oxy]methyl][[[bis(1-methylethyl)amino](2-cyanoethoxy)phosphino]oxy]methyl]propanedioate (6).

1H-Tetrazole (0.5 mmol, 1.1 mL of 0.45 M solution in MeCN) was added to 1 (553 mg, 1.0 mmol) and 2-cyanoethyl N,N,N',N'-tetraisopropyl phosphorodiamidite (332 mg, 1.1 mmol) in CH$_2$Cl$_2$ (5 mL). The solution was stirred for 2 h, and 5% aqueous NaHCO$_3$ (5 mL) was added. The mixture was diluted with brine (15 mL) and the product was extracted with CH$_2$Cl$_2$ (3×40 mL). The extracts were dried over Na$_2$SO$_4$ and evaporated. The residue was purified on a silica gel column eluting with a gradient from 0:95:5 to 30:65:5 ethyl acetate/hexane/triethylamine to give 6 (650 mg, 86.3%) as a colorless oil. HR FAB MS: found m/z 752.8309; C$_{40}$H$_{53}$N$_2$O$_{10}$P requires 752.8301. $^1$H NMR (CDCl$_3$) δ 7.40–7.25 (6H, m), 6.9–6.65 (6H, m), 4.3–4.0 (6H, m), 3.77 (9H, s), 3.65 (2H, s), 3.8–3.4 (4H, m), 2.55 (2H, m), 1.40–1.00 (18H, m). $^{13}$C NMR (CDCl$_3$) δ 168.6 (C), 168.4 (C), 158.3 (C), 136.5 (C), 130.0 (CH), 117.3 (C), 113.0 (CH), 85.6 (C), 63.9, 63.6 (CH$_2$), 62.1, 61.9 (CH$_2$), 61.4 (CH$_2$), 61.3 (C), 61.1, 60.9 (CH$_2$), 55.1 (CH$_3$), 43.1 (CH), 42.9 (CH), 24.6 (CH$_3$), 24.4 (CH$_3$), 20.5 (CH$_2$), 14.2 (CH$_3$). $^{31}$P NMR (CDCl$_3$) δ 147.4.

Example 7

Diethyl[[[tris(4-methoxyphenyl)methyl]oxy]methyl][[[bis(1-methylethyl)amino][(9H-fluorene-9-yl)methoxyl]phosphibno]oxy]methyl]propanedioate (7).

Compound 7 was prepared from 1 (1430 mg, 2.6 mmol), chloro bis[(N,N,-diisopropyl)amino]phosphite (827 mg, 3.1 mmol), and (9H-fluorene-9-yl)methanol (712 mg, 3.6 mmol) as described for 3. Isolation on a silica gel column using gradient from 0:99:1 to 25:74:1 ethyl acetate/hexane/triethylamine gave 7 (1548 mg, 68.1%) as a white solid foam. HR FAB MS: found m/z 727.3486; C$_{39}$H$_{54}$NO$_{10}$P requires 727.3485. $^1$H NMR (CDCl$_3$) δ 7.8–7.5 (4H, m); 7.5–7.15 (10H, m); 6.9–6.7 (6H, m); 4.50–4.22 (2H, m); 4.20–4.05 (4H, m); 4.05–3.85 (2H, m); 3.72 (9H, s); 3.80–3.40 (5H, m); 1.30–1.00 (18H, m). $^{31}$P NMR (CDCl$_3$) δ 147.4.

Example 8

Preparation of the Solid Support 32

Referring to scheme 2, a mixture of 1 (1.11 g, 2.0 mmol), 1,4-dioxane-2,6-dione (0.70 g, 6.0 mmol), Py (5 mL), and dioxane (5 mL) was kept overnight at room temperature. The solvent was evaporated and the residue was dissolved in ethyl acetate (50 mL). The solution was washed with 2 M aqueous triethylammonium acetate (5×10 mL) and water (5×10 mL), dried over Na$_2$SO$_4$. The extract was evaporated to give crude monoester of 2 with diglycolic acid (1.54 g; triethylammonium salt) as a solid foam in a quantitative yield.

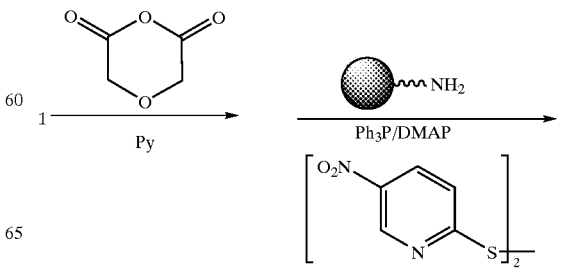

Scheme 2

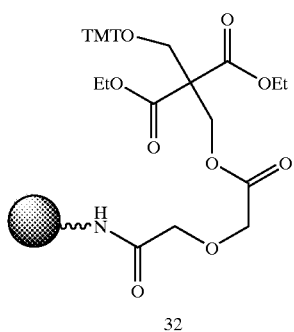

32

Crude product from the previous step (0.99 g, 1.28 mmol) and triphenylphosphine (0.40 g, 1.5 mmol) were dissolved in 1,2-dichloroethane (5 mL). To this was added a solution of 3,3'-dinitrodipyridyldisulfide (0.47 g, 1.5 mmol) and DMAP (0.18 g, 1.5 mmol) in 1,2-dichloroethane (5 mL). The mixture was shaken for 15 min and filtered. The precipitate was washed on filter with 1,2-dichloroethane (5 mL), and the combined filtrates were added to aminoalkyl CPG (5.98 g; 119 μmol g$^{-1}$, 0.71 mmol). The suspension was shaken for 1 h and filtered. The solid support was washed with 1,2-dichloroethane (3×10 mL), treated with Ac$_2$O/N-methylimidazole/THF (10:10:80) for 30 min, washed with 1,2-dichloroethane (5×10 mL) and MeCN (5×10 mL), and dried to give 32. An aliquot of 32 was treated with TFA (2% in CH$_2$Cl$_2$), and the concentration of the released trimethoxytrityl cation was determined colorimetrically at 486 nm to give the loading of 80.5 μmol g$^{-1}$.

Example 9

Oligonucleotide Synthesis

Referring to scheme 3, oligonucleotide synthesis was carried out on an ABI 380B DNA Synthesizer on 1 to 20 μmol scale using phosphoramidite chemistry. For the coupling step, 0.1 M solutions of phosphoramidite building blocks in MeCN (for 2, 0.1 M solution in CH$_2$Cl$_2$:MeCN 50:50, v/v or in CH$_2$Cl$_2$) were used; 0.45 M 1H-tetrazole was used as an activator. The coupling time for phosphoramidites 2, 3, and 5 was 600 s.

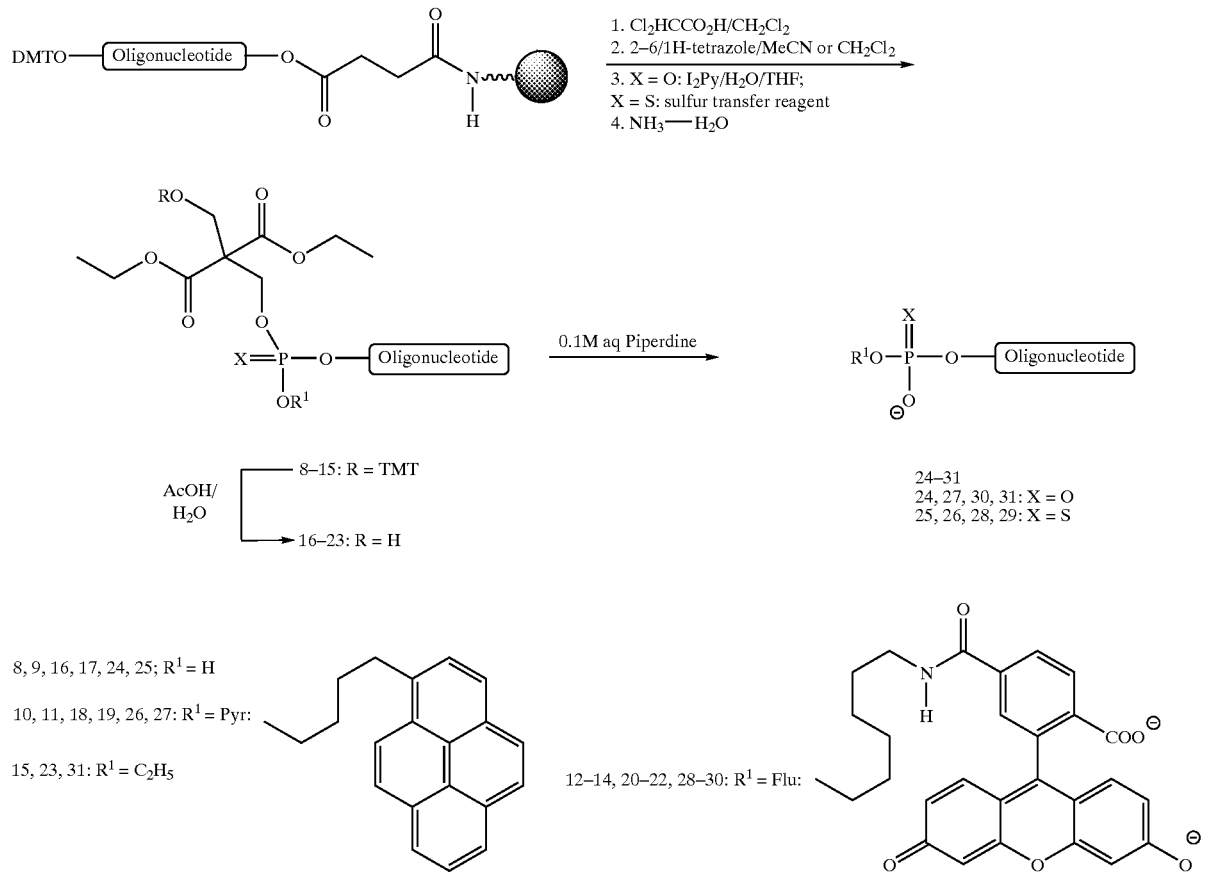

All oligonucleotides were assembled using the standard base protection strategy: N-benzoyl protected dA, dC, 2'-O-(2-methoxyethyl)-A, and 2'-O-methoxyethyl)-5-methyl-C phosphoramidites and N-isobutyryl protected dG and 2'-O-(2-methoxyethyl)-G phosphoramidites. Additionally, 9–12 were assembled using N-phenoxyacetyl dA, dC, and dG phosphoramidites. For the preparation of oligonucleotides 8–13, 33–35, 41b, and 54b, phosphoramidites protected with 2-cyanoethyl group at the P(III) were used.[5] For the synthesis of oligonucleotides 41a and 54a phosphoramidites protected with N-isopropyl-(4-methoxybenzamido)ethyl group were used.[1] The 5'-terminal phosphorylation in preparation of 8 and 9 was performed using phosphoramidites 6 and 7 to demonstrate a very similar performance of both reagents. For preparation of 41a and 41b, the last coupling was carried out using 5'-O-(4,4'-dimethoxytrityl)-3'-O-(N, N-diisopropylamino) [2-(4-methoxybenzamido)ethoxy] phosphinyl-2'-deoxythymidine as a building block.[1]

For the oxidation step, a commercial iodine oxidizer or t-BuOOH (10% in MeCN) were used. For sulfurization, 3H-1,2-benzodithiol-3-one 1,1-dioxide[4] (0.05 M in MeCN) was used as the sulfur-transfer reagent. Thus, oligonucleotides 8, 11, 14, 15, 33 were assembled using the iodine oxidizer. Oligonucleotides 9, 10, 12, 13, 35 were assembled using 3H-1,2-benzodithiol-3-one 1,1-dioxide. Oligonucleotides 34, 41a, 41b, 54a, and 54b that contained both P=S and P=O linkages were assembled using 3H-1,2-benzodithiol-3-one 1,1-dioxide for sulfuration and t-BuOOH for oxidation.

Example 10
Releasing Oligonucleotides from Solid Support and Deprotection

Referring to scheme 4, for all oligonucleotides, concentrated ammonium hydroxide was used as a deprotecting agent. On completing the chain assembly, the oligonucleotides 8, 14, and 15 were treated for 2 h at room temperature. The oligonucleotides 9, 33–35, and 41 were deprotected for 6 h at 55° C.

Scheme 4

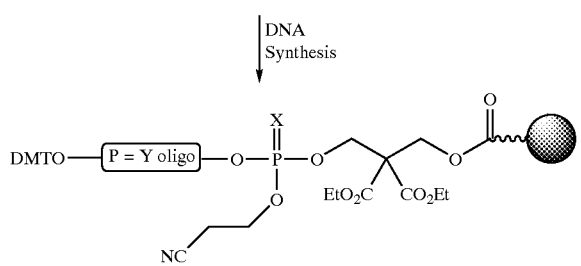

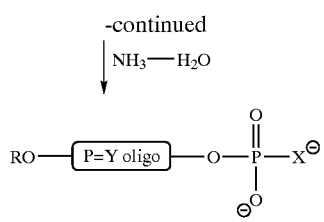

33–35: R = DMT
36–38: R = H

AcOH/H$_2$O 33, 36: X, Y = O;
34, 37: X = S; Y = O;
35, 38: X, Y = S

Under optimized conditions, the oligonucleotides 10–13 and 54 that possessed 5'-terminal phosphotriester moiety and phenoxyacetyl as the base protecting groups were treated at room temperature for 2 h. Alternatively, when nucleic bases were protected with the standard protecting groups, 10–13 and 54 were deprotected for 2 days at room temperature. On evaporation, the deprotected oligonucleotides were isolated by reversed phase HPLC and characterized by ESMS as described below.

Example 11

Detritylation Procedure

Oligonucleotides 8, 9, 33–35, and 42 were deprotected with 10% aqueous AcOH (3 mL and 100 mL for 1 and 20 μmol scale, correspondingly) for 30 min.

Oligonucleotides 10–15, 25 were dissolved in 10% aqueous AcOH (3 mL and 100 mL for 1 and 20 μmol scale, correspondingly). When the desalted material was subjected to the removal of TMT protecting group, the deprotection was complete in 90 min. When the samples of oligonucleotides contained the HPLC buffer, NH$_4$OAc, the reaction mixture was kept for 4 to 5 h at room temperature.

When the detritylation was complete, the reaction mixtures were evaporated. The oligonucleotides 36–38 and 43 were desalted and characterized (Tables 3 and 4, respectively). The oligonucleotides 16–22 (Tables 1 and 2) were coevaporated with water and the 5'-terminal 3-hydroxy-2,2-bis(ethoxycarbonyl)propyl-1 group was removed as described below.

TABLE 1

HPLC Retention Times for Oligonucleotides 8–31.

| | | | | Retention time, min[b] | |
|---|---|---|---|---|---|
| Compound | R | R$^1$ | Sequence, 5' to 3' | X$^a$ | Gradient 1 | Gradient 2 |
| 8 | TMT | H | T$_{12}$ <SEQ. ID. NO. 1> | O | 32.8 | — |
| 9 | TMT | H | ATGCAT$_2$CTGC$_5$A$_2$G$_2$A <SEQ. ID. NO. 2> | S | 27.7 | 23.8 |
| 10 | TMT | Pyr | ATGCAT$_2$CTGC$_5$A$_2$G$_2$A <SEQ. ID. NO. 2> | S | — | 30.2, 30.7 |
| 11 | TMT | Pyr | ATGCAT$_2$CTGC$_5$A$_2$G$_2$A <SEQ. ID. NO. 2> | O | — | 29.1 |

TABLE 1-continued

HPLC Retention Times for Oligonucleotides 8–31.

| Compound | R | $R^1$ | Sequence, 5' to 3' | $X^a$ | Retention time, min[b] Gradient 1 | Gradient 2 |
|---|---|---|---|---|---|---|
| 12 | TMT | Flu | ATGCAT$_2$CTGC$_5$A$_2$G$_2$A <SEQ. ID. NO. 2> | S | 33.4, 34.2 | — |
| 13 | TMT | Flu | AGCT$_2$C T$_3$GCACA TGTA$_3$[c] <SEQ. ID. NO. 3> | S | 35.9, 36.3 | — |
| 14 | TMT | Flu | T$_{12}$ <SEQ. ID. NO. 1> | O | 32.9 | — |
| 15 | TMT | C$_2$H$_5$ | T$_{12}$ <SEQ. ID. NO. 1> | O | 33.0 | — |
| 16 | H | H | T$_{12}$ <SEQ. ID. NO. 1> | O | 18.0 | — |
| 17 | H | H | ATGCAT$_2$CTGC$_5$A$_2$G$_2$A <SEQ. ID. NO. 2> | S | 19.6 | 16.4 |
| 18 | H | Pyr | ATGCAT$_2$CTGC$_5$A$_2$G$_2$A <SEQ. ID. NO. 2> | S | — | 25.0 |
| 19 | H | Pyr | ATGCAT$_2$CTGC$_5$A$_2$G$_2$A <SEQ. ID. NO. 2> | O | — | 24.5 |
| 20 | H | Flu | ATGCAT$_2$CTGC$_5$A$_2$G$_2$A <SEQ. ID. NO. 2> | S | 23.4 | — |
| 21 | H | Flu | AGCT$_2$C T$_3$GCACA TGTA$_3$[c] <SEQ. ID. NO. 3> | S | 28.5 | — |
| 22 | H | Flu | T$_{12}$ <SEQ. ID. NO. 1> | O | 22.7 | — |
| 23 | H | C$_2$H$_5$ | T$_{12}$ <SEQ. ID. NO. 1> | O | 21.5 | — |
| 24 | — | H | T$_{12}$ <SEQ. ID. NO. 1> | O | 16.2 | — |
| 25 | — | H | ATGCAT$_2$CTGC$_5$A$_2$G$_2$A <SEQ. ID. NO. 2> | S | 18.0 | 15.2 |
| 26 | — | Pyr | ATGCAT$_2$CTGC$_5$A$_2$G$_2$A <SEQ. ID. NO. 2> | S | 22.6 | 17.1 |
| 27 | — | Pyr | ATGCAT$_2$CTGC$_5$A$_2$G$_2$A <SEQ. ID. NO. 2> | O | 22.0 | 16.7 |
| 28 | — | Flu | ATGCAT$_2$CTGC$_5$A$_2$G$_2$A <SEQ. ID. NO. 2> | S | 19.1 | 14.5 |
| 29 | — | Flu | AGCT$_2$C T$_3$GCACA TGTA$_3$[c] <SEQ. ID. NO. 3> | S | 21.7 | — |
| 30 | — | Flu | T$_{12}$ <SEQ. ID. NO. 1> | O | 18.1 | — |
| 31 | — | C$_2$H$_5$ | T$_{12}$ <SEQ. ID. NO. 1> | O | 17.9 | — |

[a] All oligonucleotides contained uniform, either phosphate (X = O) or phosphorothioate (X = S) backbone;
[b] For HPLC conditions, consult Experimental Procedures;
[c] 2'-O-(2-methoxyethyl) ribonucleotide residues are italicized;
C stands for 5-methyl-2'-O-(2-methoxyethyl)cytidine residue.

TABLE 2

UV and ESMS data for Oligonucleotides 8–31.

| Compound | Reporter group, $\lambda_{max}$, nm | ES MS found, amu | Molecular Formula | calc., amu |
|---|---|---|---|---|
| 8 | — | 4202.8 | C$_{151}$H$_{192}$N$_{24}$O$_{93}$P$_{12}$ | 4202.9 |
| 9 | — | 6998.0 | C$_{224}$H$_{280}$N$_{74}$O$_{108}$P$_{20}$S$_{20}$ | 6997.8 |
| 10 | 313, 327, 343 | 7252.8 | C$_{244}$H$_{296}$N$_{74}$O$_{108}$P$_{20}$S$_{20}$ | 7254.2 |
| 11 | 314, 326, 343 | 6932.8 | C$_{244}$H$_{296}$N$_{74}$O$_{128}$P$_{20}$ | 6932.9 |
| 12 | 463, 496 | 7455.5 | C$_{251}$H$_{303}$N$_{75}$O$_{114}$P$_{20}$S$_{20}$ | 7455.3 |
| 13 | 463, 496 | 8402.4 | C$_{292}$H$_{382}$N$_{72}$O$_{140}$P$_{20}$S$_{20}$ | 8401.4 |
| 14 | 463, 496 | 4660.7 | C$_{178}$H$_{215}$N$_{25}$O$_{99}$P$_{12}$ | 4660.4 |
| 15 | — | 4229.2 | C$_{153}$H$_{196}$N$_{24}$O$_{93}$P$_{12}$ | 4231.0 |
| 16 | — | 3870.5 | C$_{129}$H$_{172}$N$_{24}$O$_{90}$P$_{12}$ | 3870.5 |
| 17 | — | 6665.5 | C$_{203}$H$_{260}$N$_{74}$O$_{105}$P$_{20}$S$_{20}$ | 6665.4 |
| 18 | 322, 336, 352 | 6920.6 | C$_{222}$H$_{276}$N$_{74}$O$_{105}$P$_{20}$S$_{20}$ | 6921.8 |
| 19 | 322, 335, 353 | 6599.1 | C$_{222}$H$_{276}$N$_{74}$O$_{125}$P$_{20}$ | 6600.5 |
| 20 | 456, 472 | 7122.1 | C$_{229}$H$_{283}$N$_{75}$O$_{111}$P$_{20}$S$_{20}$ | 7122.9 |
| 21 | 458, 482 | 8067.2 | C$_{270}$H$_{362}$N$_{72}$O$_{137}$P$_{20}$S$_{20}$ | 8069.0 |
| 22 | 456, 472 | 4327.0 | C$_{156}$H$_{195}$N$_{25}$O$_{96}$P$_{12}$ | 4328.0 |
| 23 | — | 3897.7 | C$_{131}$H$_{176}$N$_{24}$O$_{90}$P$_{12}$ | 3898.6 |
| 24 | — | 3668.1 | C$_{120}$H$_{158}$N$_{24}$O$_{85}$P$_{12}$ | 3668.3 |
| 25 | — | 6463.4 | C$_{193}$H$_{246}$N$_{74}$O$_{100}$P$_{20}$S$_{20}$ | 6463.2 |
| 26 | 322, 336, 352 | 6720.1 | C$_{213}$H$_{262}$N$_{74}$O$_{100}$P$_{20}$S$_{20}$ | 6719.6 |
| 27 | 322, 336, 352 | 6400.3 | C$_{213}$H$_{262}$N$_{74}$O$_{120}$P$_{20}$ | 6398.3 |
| 28 | 458, 472 | 6919.6 | C$_{220}$H$_{269}$N$_{75}$O$_{106}$P$_{20}$S$_{20}$ | 6920.7 |
| 29 | 456, 482 | 7869.0 | C$_{261}$H$_{348}$N$_{72}$O$_{132}$P$_{20}$S$_{20}$ | 7866.8 |
| 30 | 456, 472 | 4125.4 | C$_{147}$H$_{181}$N$_{25}$O$_{91}$P$_{12}$ | 4125.8 |
| 31 | — | 3695.8 | C$_{122}$H$_{164}$N$_{24}$O$_{85}$P$_{12}$ | 3696.4 |

TABLE 3

ESMS data oligonucleotides 33–40.[a]

| | Sequence, 5' to 3' | Backbone | ESMS, found | Molecular Formula | ESMS, calculated |
|---|---|---|---|---|---|
| 33 | DMTr-TGCATC$_5$AG$_2$C$_2$AC$_2$ATpO <SEQ. ID. NO. 4> | P=O | 6365.2 | C$_{211}$H$_{263}$N$_{71}$O$_{122}$P$_{20}$ | 6365.2 |
| 34 | DMTr-TGCATC$_5$AG$_2$C$_2$AC$_2$ATpS <SEQ. ID. NO. 5> | P=O | 6381.7 | C$_{211}$H$_{263}$N$_{71}$O$_{121}$P$_{20}$S | 6381.3 |
| 35 | DMTr-TGCATC$_5$AG$_2$C$_2$AC$_2$ATpS <SEQ. ID. NO. 5> | P=S | 6686.9 | C$_{211}$H$_{263}$N$_{71}$O$_{102}$P$_{20}$S$_{20}$ | 6686.5 |

TABLE 3-continued

ESMS data oligonucleotides 33–40.[a]

| Sequence, 5' to 3' | Backbone | ESMS, found | Molecular Formula | ESMS, calculated |
|---|---|---|---|---|
| 36 TGCATC$_5$AG$_2$C$_2$AC$_2$ATpO <SEQ. ID. NO. 6> | P=O | 6062.2 | C$_{190}$H$_{245}$N$_{71}$O$_{120}$P$_{20}$ | 6062.8 |
| 37 TGCATC$_5$AG$_2$C$_2$AC$_2$ATpS <SEQ. ID. NO. 7> | P=O | 6079.4 | C$_{190}$H$_{245}$N$_{71}$O$_{119}$P$_{20}$S | 6078.9 |
| 38 TGCATC$_5$AG$_2$C$_2$AC$_2$ATpS <SEQ. ID. NO. 7> | P=S | 6384.7 | C$_{190}$H$_{245}$N$_{71}$O$_{100}$P$_{20}$S$_{20}$ | 6384.2 |
| 39 TGCATC$_5$AG$_2$C$_2$AC$_2$ATpS-Pyr <SEQ. ID. NO. 8> | P=O | 6350.9 | C$_{209}$H$_{258}$N$_{72}$O$_{120}$P$_{20}$S | 6350.2 |
| 49 TGCATC$_5$AG$_2$C$_2$AC$_2$ATpS-Flu <SEQ. ID. NO. 9> | P=O | 6467.0 | C$_{212}$H$_{258}$N$_{72}$O$_{125}$P$_{20}$S | 6466.2 |

TABLE 4

ESMS Data for Oligonucleotides 42–53.[a]

| Oligonucleotide | Calculated | Formula | Found |
|---|---|---|---|
| 42 | 6575.5 | C$_{221}$H$_{274}$N$_{72}$O$_{122}$P$_{20}$S$_2$ | 6576.5 |
| 43 | 6272.2 | C$_{200}$H$_{256}$N$_{72}$O$_{120}$P$_{20}$S$_2$ | 6272.3 |
| 45 | 6543.5 | C$_{219}$H$_{269}$N$_{73}$O$_{121}$P$_{20}$S$_2$ | 6542.4 |
| 46 | 6366.3 | C$_{209}$H$_{258}$N$_{72}$O$_{119}$P$_{20}$S$_2$ | 6366.7 |
| 50 | 6637.6 | C$_{228}$H$_{271}$N$_{73}$O$_{120}$P$_{20}$S$_2$ | 6638.0 |
| 51 | 6529.4 | C$_{215}$H$_{259}$N$_{75}$O$_{122}$P$_{20}$S$_2$ | 6529.5 |
| 52 | 6556.5 | C$_{219}$H$_{268}$N$_{74}$O$_{121}$P$_{20}$S$_2$ | 6555.9 |
| 53 | 6753.7 | C$_{231}$H$_{271}$N$_{73}$O$_{125}$P$_{20}$S$_2$ | 6753.1 |

[a]Oligonucleotide sequence: Tp*GCATC$_5$AG$_2$C$_2$AC$_2$ATp** <SEQ. ID. NO. 10> where p* and p** are modified phosphorothioate groups (See Schemes 6 and 7).

Example 12
Removal of 5'-terminal 3-hydroxy-2,2-bis(ethoxycarbonyl) propyl-1 Protecting Group Oligonucleotides 16–22 were dissolved in 0.1 M aqueous piperidine (3 mL and 100 mL for 1 and 20 μmol scale, respectively). The reaction mixture was left for 30 min at room temperature. The solvent was evaporated, and the residue was re-dissolved in water (1 to 5 mL). The target oligonucleotides. 24–31 (Tables 1 and 2) were desalted by reversed phase HPLC.

Example 13
Oligonucleotide Purification by HPLC

The oligonucleotides were analyzed, and, for syntheses on 1 to 2 μmol scale, isolated by reverse phase chromatography on a Waters DeltaPak C18 column (15 μm; 300 Å; 3.9×300 mm). As buffers A and B, 0.1 M NH$_4$OAc and 80% aqueous MeCN were respectively used at a flow rate 1.5 mL min$^{-1}$. Linear gradients from 0 to 60% B in 40 min (Gradient 1) and 0 to 100% in 40 min (Gradient 2) were employed. Retention times for oligonucleotides 8–31 are presented in Table 1. For desalting, the same C18 column was eluted stepwise with 0.1 M NH$_4$OAc (10 min), then water (10 min), and, finally, 50% aqueous MeCN (20 min) to give an oligonucleotide as an ammonium salt. For isolation of oligonucleotides synthesized on 20 μmol scale, Waters DeltaPak C18 column (15 μm; 300 Å; 25×100 mm) was used with buffer systems as described above at the flow rate 15 mL min$^{-1}$.

Example 14
Oligonucleotides 39 and 40

Referring to scheme 5, oligonucleotide 37 and N-(1-pyrenylmethyl)iodoacetamide, 44, were added to DMSO. The reaction was kept for 4 h at 37° C. and diluted with water. The product was isolated and desalted by reverse phase HPLC to give 39 as a triethylammonium salt (Table 1).

Oligonucleotide 37 and 5-iodoacetamidofluorescin, 49, were reacted and the product was isolated and desalted by reverse phase HPLC to give 40 as a triethylammonium salt (Table 1).

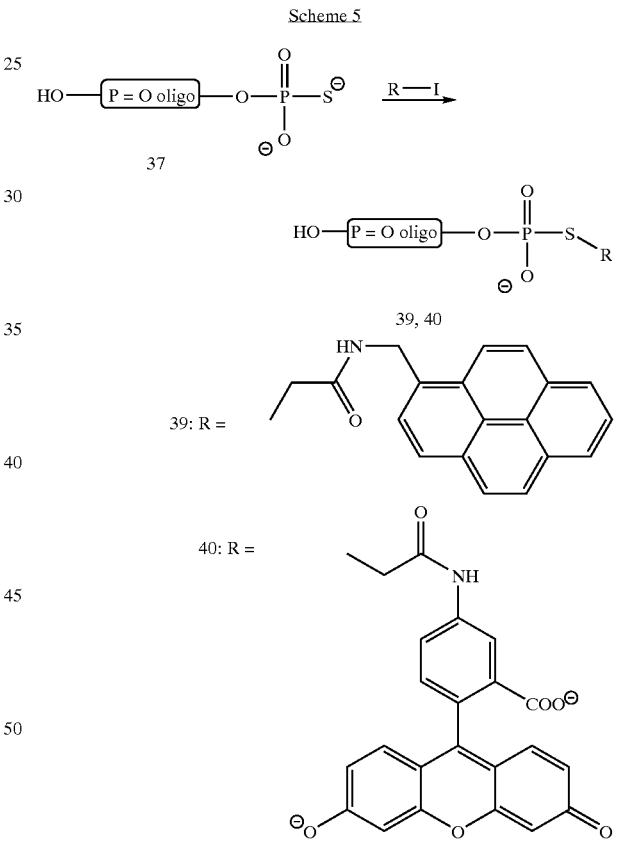

Scheme 5

Example 15
Oligonucleotide 45

Referring to scheme 6, oligonucleotide 43 (36 OD, 1.0 mM solution in 200 mM ethyldiisopropylammonium acetate, pH 7.0, 200 μL) and N-(1-pyrenylmethyl) iodoacetamide, 44, (2.0 mg, 25 mM solution in DMSO, 200 μL) were added to DMSO (400 μL). The reaction was kept for 4 h at 37° C. and diluted to 10 mL with water. The product was isolated and desalted by reverse phase HPLC to give 45 (25 OD, 70%) as a triethylammonium salt (Table 1).

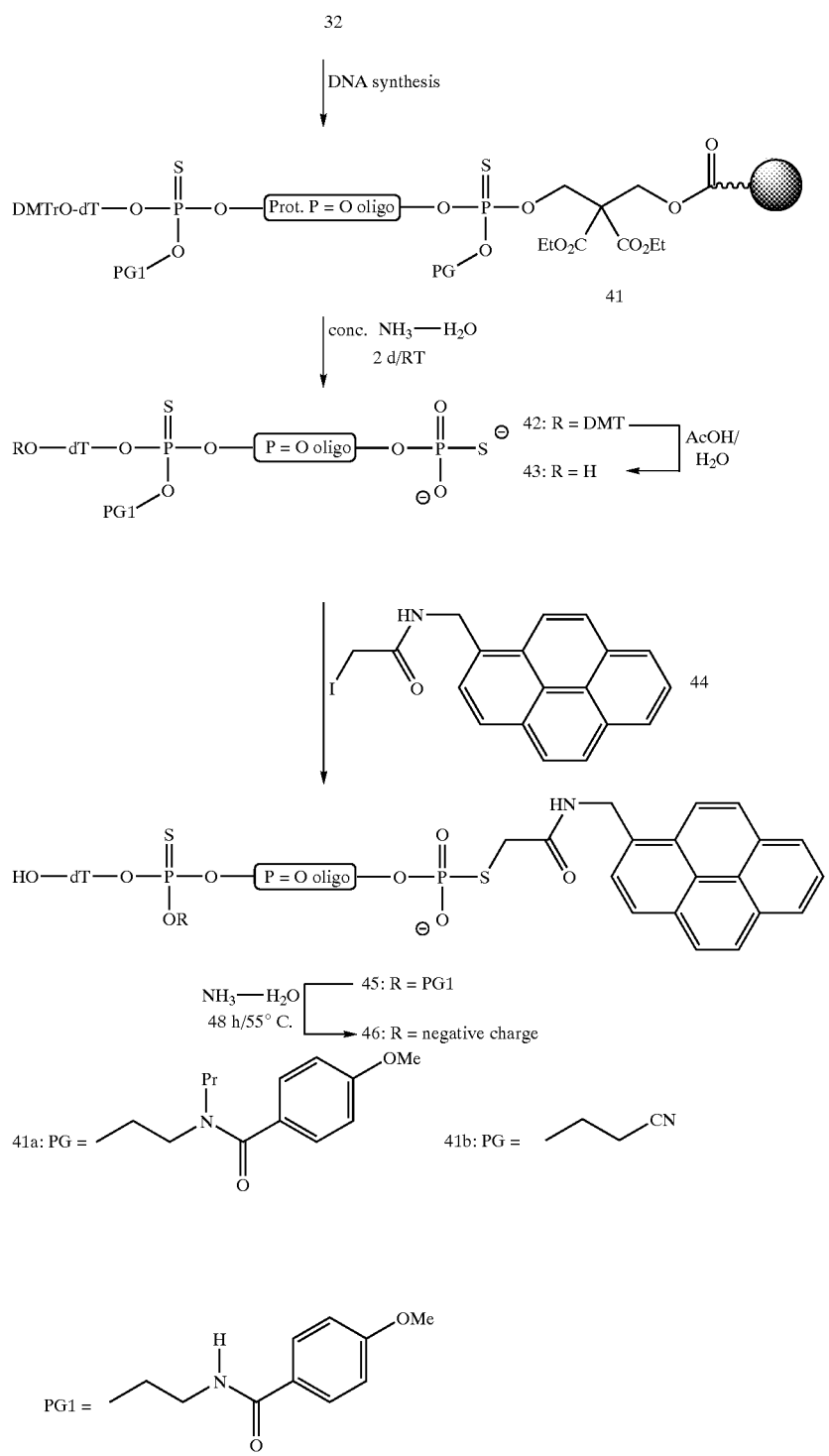

Example 16

Oligonucleotide 46

Compound 45 (24 OD) was deprotected with conc. aqueous ammonia (3 mL) for 48 h at 55° C., and the solution was evaporated. The residue was dissolved in 20% aq DMSO, and the product was isolated and desalted by reverse phase HPLC to give 46 (21.5 OD, 90%) as a triethylammonium salt (Table 4).

Example 17

Oligonucleotide 50

Referring to scheme 7, oligonucleotide 46 (5 OD) and compound 44 (0.5 mg) were reacted in 50 mM ethyldiisopropylammonium acetate buffer (75% aqueous DMSO; pH 7.0; 200 μL) for 8 h at 37° C. as described for 45. The solution was diluted to 10 mL with water. The product was isolated and desalted by reverse phase HPLC to give 50 (3.5 OD, 70%) as a triethylammonium salt (Table 4).

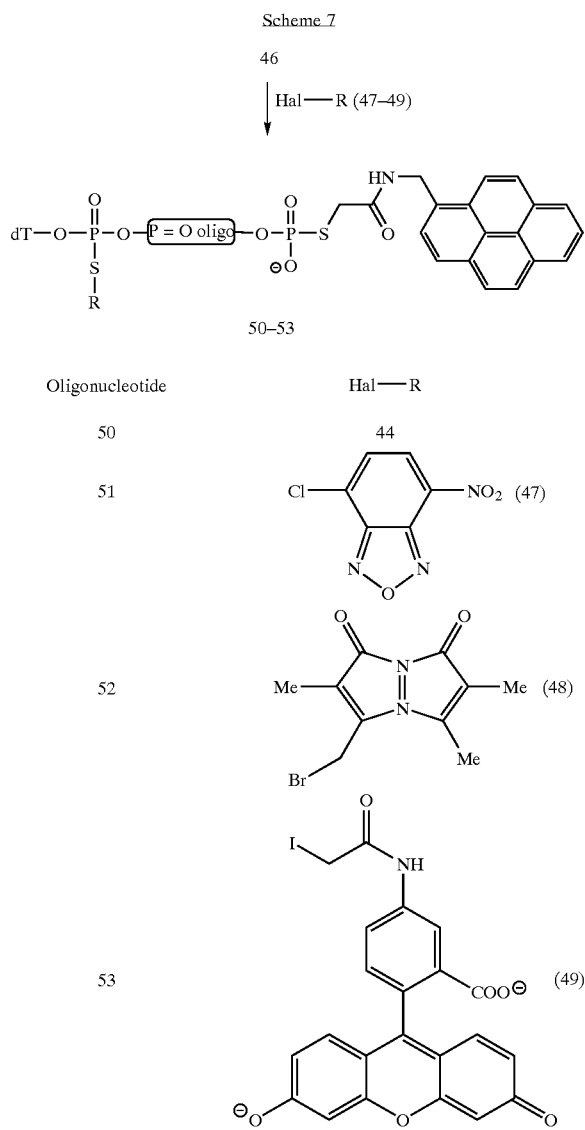

Example 18

Oligonucleotide 51

Oligonucleotide 46 (5 OD) and 4-chloro-7-nitrobenzofurazan, 47, (0.2 mg) were reacted in 0.1 M ethyldiisopropylammonium acetate buffer (60% aq MeCN; pH 7.0; 400 µL) for 6 h at 37° C. and diluted to 4 mL with water. The product was isolated and desalted by reverse phase HPLC to give 51 (4 OD, 80%) as a triethylammonium salt (Table 4).

Example 19

Oligonucleotide 52

Oligonucleotide 46 (5 OD) and monobromobimane, 48, (0.27 mg) were reacted in 0.1 M ethyldiisopropylammonium acetate buffer (60% aq MeCN; pH 7.0; 400 µL) for 2 h at 37° C. and diluted to 4 mL with water. The product was isolated and desalted by reverse phase HPLC to give 52 (4.5 OD, 90%) as a triethylammonium salt (Table 4).

Example 20

Oligonucleotide 53

Oligonucleotide 46 (25 OD) and 5-iodoacetamidofluorescein, 49, (0.52 mg) were reacted in 0.1 M ethyldiisopropylammonium acetate buffer (60% aq MeCN; pH 7.0; 400 µL) for 10 h at 37° C. and diluted to 4 mL with water. The product was isolated and desalted by reverse phase HPLC to give 53 (19 OD, 75%) as a triethylammonium salt (Table 4).

Example 21

Oligonucleotide 56

Referring to scheme 8, oligonucleotide 55 (125 OD) and 5-iodoacetamidofluorescein, 49, (1.5 mg) were reacted in 0.1 M ethyldiisopropylammonium acetate buffer (60% aq MeCN; pH 7.0; 400 µL) for 10 h at 37° C. and diluted to 4 mL with water. The product was isolated by reverse phase HPLC, evaporated, and dissolved in concentrated ammonium hydroxide (5 mL). The solution was heated for 48 h at 55° C. and evaporated. The residue was treated with 5% aqueous AcOH (3 mL) for 15 min, evaporated, and treated with 0.1 M aqueous piperidine (3 mL). The product was isolated and desalted by reverse phase HPLC to give 56 (75 OD, 60%) as a triethylammonium salt (Table 5).

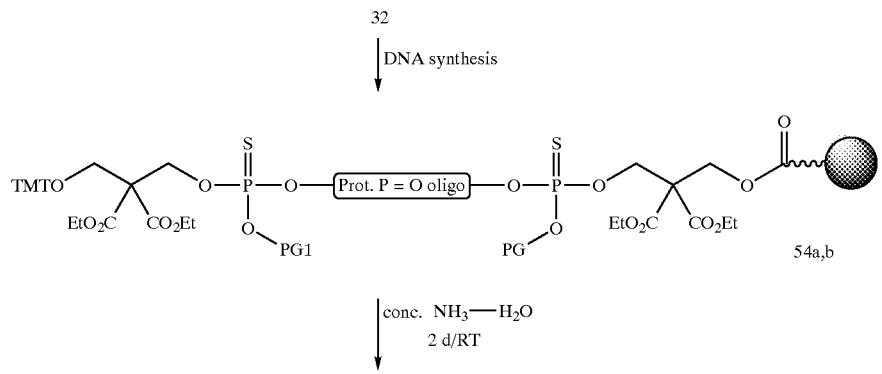

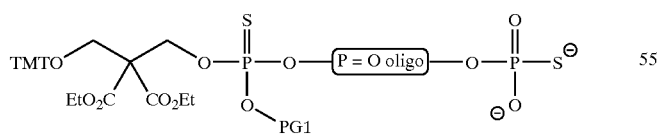

55

↓ 1. 49;
2. $NH_3$—$H_2O$;
3. $AcOH/H_2O$;
4. Piperidine/$H_2O$

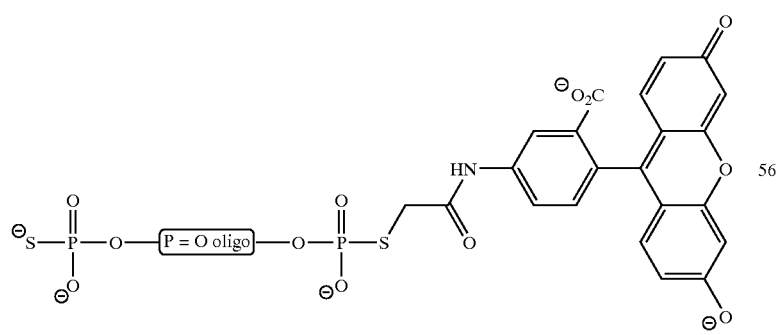

56

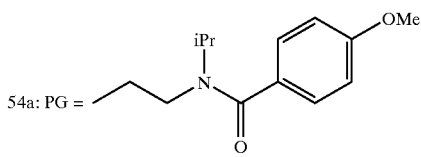

54a: PG =

54b: PG =

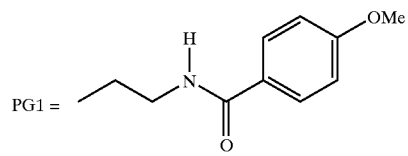

PG1 =

TABLE 5

Characterization of oligonucleotides 55–59.[a]

| | ESMS, calculated | Molecular Formula | ESMS, found |
|---|---|---|---|
| 55 | 6886.8 | $C_{231}H_{291}N_{72}O_{131}P_{21}S_2$ | 6885.9 |
| 56 | 6562.2 | $C_{912}H_{259}N_{72}O_{127}P_{21}S_2$ | 6562.9 |
| 57 | 6833.6 | $C_{231}H_{272}N_{73}O_{128}P_{21}S_2$ | 6834.6 |
| 58 | 6752.4 | $C_{222}H_{269}N_{74}O_{129}P_{21}S_2$ | 6753.1 |
| 59 | 6949.6 | $C_{234}H_{272}N_{73}O_{133}P_{21}S_2$ | 6950.8 |

[a]Oligonucleotide sequence: p*TGCATC$_5$AG$_2$C$_2$AC$_2$ATp** <SEQ. ID. NO. 11> where p* and p** are modified phosphorothioate groups (See Schemes 8 and 9).

Example 22

Oligonucleotide 57

Referring to scheme 9, oligonucleotide 56 (7 OD) and compound 44 (0.7 mg) were reacted in 50 mM ethyldiisopropylammonium acetate buffer (75% aqueous DMSO; pH 7.0; 250 μL) for 8 h at 37° C. as described for 45. The solution was diluted to 10 mL with water. The product was isolated and desalted by reverse phase HPLC to give 57 (5.2 OD, 75%) as a triethylammonium salt (Table 5).

Scheme 9

56

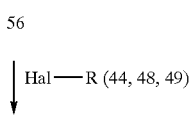

Hal—R (44, 48, 49)

↓

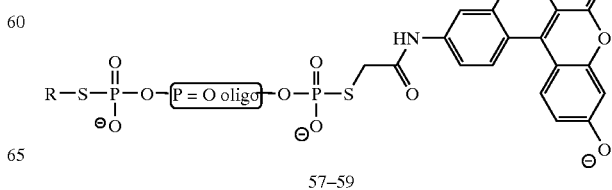

57–59

| Oligonucleotide | Hal—R |
|---|---|
| 57 | 44 |
| 58 | 48 |
| 59 | 49 |

Example 23

Oligonucleotide 58

Oligonucleotide 56 (10 OD) and monobromobimane, 48, (0.53 mg) were reacted in 0.1 M ethyldiisopropylammonium acetate buffer (60% aq MeCN; pH 7.0; 400 µL) for 2 h at 37° C. and diluted to 4 mL with water. The product was isolated and desalted by reverse phase HPLC to give 58 (8 OD, 80%) as a triethylammonium salt (Table 5).

Example 24

Oligonucleotide 59

Oligonucleotide 56 (15 OD) and 5-iodoacetamidofluorescein, 49, (0.5 mg) were reacted in 0.1 M ethyldiisopropylammonium acetate buffer (60% aq MeCN; pH 7.0; 400 µL) for 10 h at 37° C. and diluted to 4 mL with water. The product was isolated and desalted by reverse phase HPLC to give 59 (10.5 OD, 70%) as a triethylammonium salt (Table 5).

Example 25

Synthesis of Dialkylglycerol Linker 1,2-Di-O-hexadecyl-rac-glycerol succinimidyl carbamate (102) Referring to Scheme 10, 1,2-Di-O-hexadecyl-rac-glycerol (10.00 g, 18.5 mmol) was dissolved in anhydrous $CH_2Cl_2$ (150 ml). To the solution were added disuccinimidyl carbonate 7.11 g, 27.7 mmol), $Et_3N$ (10.0 ml), and MeCN (50 ml). The reaction mixture was stirred at room temperature under Ar for 6.5 h and then evaporated to dryness. The residue was dissolved in CH2Cl2 (300 ml). It was washed with saturated $NaHCO_3$ aqueous solution (3×100 ml) and with saturated NaCl aqueous solution (3×100 ml). The organic layer was dried over $Na_2SO_4$, filtered and evaporated to dryness. Compound 102 (12.60 g) was obtained as colorless powder after drying in high vacuum, which was directly used for the next step without further purification.

(1S,2S)-(+)-2-(Fmoc-ε-aminocaproylamido)-1-phenyl-1,3-propanediol (104) To the solution of Fmoc-ε-aminocaproyl succinimidyl carbamate (103, 97% of purity, 27.8 g, 60 mmol) in $CH_2Cl_2$ (300 ml) was added anhydrous pyridine followed by (1S,2S)-(+)-2-amino-1-phenyl-1,3-propanediol (10.08, 60 mmol). The reaction mixture was stirred at room temperature under Ar for 7 h. Meanwhile, white solid was produced. This insoluble material was filtered out. The filtrate was evaporated to give oil, which was dried in high vacuum overnight furnishing a yellowish powder 104 (31.0 g). For analysis 2.5 g of the crude product was dissolved in CH2Cl2/MeOH (9:1) and applied to FC (silica gel, column 3×15 cm). The column was washed with CH2Cl2, 100 ml; CH2Cl2/Me2CO 9:1, 500 ml. And the compound 104 was eluted with CH2/MeOH 9:1, 200 ml.

(1S,2S)-(+)-2-{ε-[(1,2-di-O-hexadecyl-rac-glyceroxy) carbonyl]-aminocaproyl}-amido-1-phenyl-1,3-propanediol (105) The compound 104 (9.04 g, 18 mmol) was dissolved in DMF (108 ml). To this solution piperidine (27 ml) was added. The reaction mixture was stirred at room temperature for 1 h. and then evaporated to dryness. The residue was dissolved in pyridine (36 ml). To this solution was added a solution of 1,2-Di-O-hexadecyl-rac-glycerol succinimidyl carbamate (102, 12.92 g, 18 mmol) in $CH_2Cl_2$ (135 ml). The mixture was stirred at room temperature for 5.5 h. and evaporated to dryness. The residue was dried overnight in high vacuum furnishing a yellowish solid. The solid was dissolved in $CH_2Cl_2$ (1000 ml). It was washed with saturated NaCl aqueous solution (3×300 ml). The organic layer was dried over $Na_2SO_4$, filtered and evaporated to give oil. The residue was applied to FC (silica gel, column 12×20 cm), $CH_2Cl_2$/MeOH (9:1), 2000 ml; yielding compound 105 (7.10 g, 47%) as colorless powder.

Compound 105 (6.98 g, 8.2 mmol) was co-evaporated with anhydrous pyridine three times and then dissolved in pyridine (40 ml). To this solution DMTCl (3.34 g, 9.8 mmol) was added under stirring at room temperature in three portions over 7 h. The reaction mixture was stirred at room temperature for another 15 h. The exceed DMTCl was decomposed by adding MeOH (20 ml). The solution was poured into saturated $NaHCO_3$ aqueous solution (400 ml), shaken and separated. The aqueous layer was extracted with $CH_2Cl_2$ (3×120 ml). The combined organic layer was washed with saturated NaCl aqueous solution (3×200 ml) and then dried over $Na_2SO_4$. The solid was filtered out. The filtrate was evaporated to dryness giving a gel, which was applied, to FC (silica gel, column 12×20 cm). The column was eluted with $CH_2Cl_2$/MeOH (95:5 containing drops of EtN) furnishing compound 106 (6.89 g, 73%) as colorless foam.

(1S,2S)-(+)-2-{ε-[(1,2-di-O-hexadecyl-rac-glyceroxy) carbonyl]-aminocaproyl}-amido-3-[(4,4'-dimethoxytrityl) oxy-1-phenylpropanol 1-O-(2cyanoethyl diisopropylphosphoramidite) (107) To the solution of the compound 106 (3.44 g, 3 mmol) in anhydrous $CH_2Cl_2$ (25 ml) were added $(iPr)_2Net$ (1.05 ml, 6 mmol) and 2-cyanoethyl-N,N'-diisopropylaminochlorophosphine (0.87 ml, 3.9 mmol) under Ar. The reaction mixture was stirred at room temperature for 1 h. It was then poured into 5% $NaHCO_3$ aqueous solution, shaken and separated. The aqueous layer was extracted with $CH_2Cl_2$ (3×60 ml). The combined organic layer was washed with 5% $NaHCO_3$ aqueous solution (100 ml) and saturated NaCl aqueous solution (2×120 ml), dried over $Na_2SO_4$. The solid was filtered out. The filtrate was evaporated to dryness giving a gel that was further dried in high vacuum furnishing a yellow foam (4.77 g). It was applied to FC (silica gel, column 5×15 cm): $CH_2Cl_2/Me_2CO$ (9:1), 2000 ml, yielding 107 (1.0 g) as colorless foam. Also, the starting material 106 (1.0 g) was recovered.

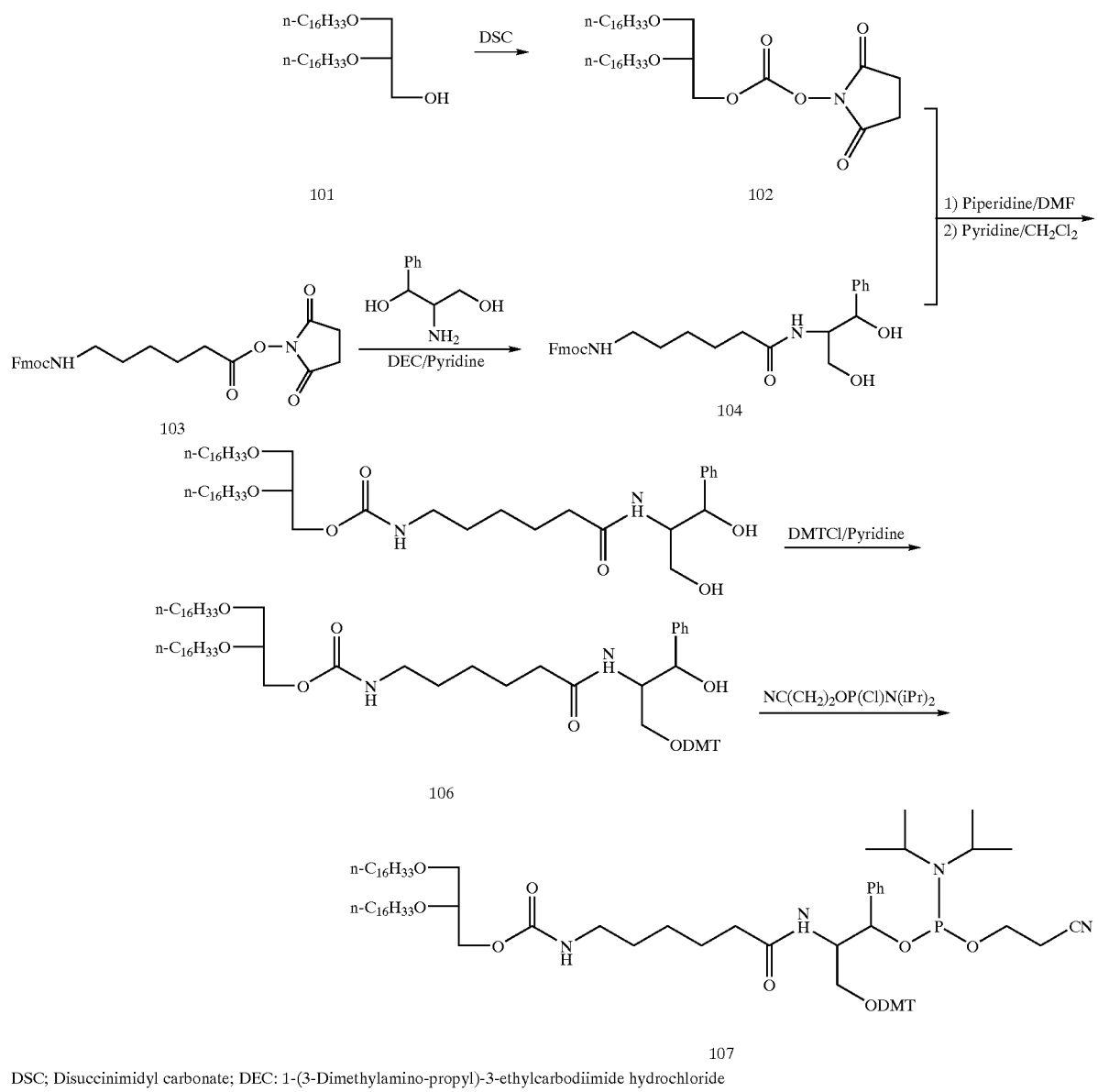

Scheme 10

DSC; Disuccinimidyl carbonate; DEC: 1-(3-Dimethylamino-propyl)-3-ethylcarbodiimide hydrochloride

Example 26

Synthesis of Cholesterol Linker

ε-N-Cholesteryloxycarbonylaminocaproic acid (109) Referring to Scheme 11, the ε-aminocaproic acid (3.93 g, 30 mmol) was suspended in pyridine (60 ml). The flask was flushed with nitrogen and to the mixture was added N,O-bis(trimethylsilyl)acetamide (10 ml, 70 mmol) under stirring. The reaction mixture was stirred at room temperature for 35 min. and then cooled in ice bath. Cholesteryl chloroformate (13.5 g, 30 mmol) was added into the reaction mixture in two portions over 2 h. The reaction was continued by stirring at room temperature for another 4 h. 2% HCl aqueous solution (150 ml) was added under cooling with ice bath. The mixture was stirred for 5 min. and then poured into a separating funnel. The product was extracted with CH2Cl2 (3×150 ml). The combined organic layer was washed with 2% HCl aqueous solution (2×120 ml) and with saturated NaCl aqueous solution (2×120 ml), dried over $Na_2SO_4$, filtered, and evaporated to dryness giving a yellow foam (109, 14.44 g).

(1S,2S)-(+)-2-[ε-(N-Cholesteryloxycarbonylamino) caproylamino]-1-phenyl-1,3-propanediol (110) To the solution of compound 109 (crude, 14.44 g) in pyridine (50 ml) 2-(Diethylamino)ethyl chloride hydrochloride (DEC, 6.03 g, 31.5 mmol) was added under nitrogen at room temperature The mixture was stirred at room temperature under nitrogen for 0.5 h. (1S,2S)-(+)-2-Amino-1-phenyl-1,3-propanediol (5.01 g, 30.0 mmol) was then added followed by another portion of pyridine (10 ml). The reaction mixture was stirred at room temperature for 19 h. It was evaporated to dryness. The residue was dissolved in $CH_2Cl_2$ (2550 ml), washed with saturated NaHCO₃ aqueous solution (2×120 ml) followed by saturated NaCl aqueous solution (2×150 ml). The combined aqueous layer was re-extracted with CH₂Cl₂ (3×200 ml). The combined organic layer was dried over Na₂SO₄, filtered, and evaporated to give a yellow foam 110 (16.93 g, 81%). For analysis, the crude product (5.67 g) was purified further by FC (silica gel, column 3×12 cm): CH₂Cl₂, 400 ml; CH₂Cl₂/MeOH (95:5), 250 ml; CH₂Cl₂/MeOH (9.1), 400 ml furnishing slight yellow powder 110 (4.89 g).

(1S,2S)-(+)-[(4,4'-Dimethoxytrityl)oxy]-2-[ε-(N-cholesteryloxycarbonylamino)-caproylamino]-1-phenylpropanol (111) The compound 110 (crude, 12.44 g) was co-evaporated with pyridine (anhydrous, 3×20 ml) and dissolved in anhydrous pyridine (50 ml). To the solution DMTCl (5.62 g, 16.6 mmol) was added in three portions over 7 h. The reaction mixture was stirred at room temperature for additional 14 h. The excess DMTCl was then decomposed by adding MeOH (12 ml) and stirring for 10 min. The resulting solution was poured into 5% NaHCO₃ aqueous solution (150 ml). The mixture was extracted with CH₂Cl₂ (4×150 ml). The organic layer was washed by saturated NaCl aqueous solution (200 ml), dried over Na₂SO₄, filtered and evaporated to dryness. The residue was applied to FC (silica gel, column 5×8 cm): CH₂Cl₂/Me₂CO (95:5) 750 ml, CH₂Cl₂Me₂CO (9:1) 750 ml, yielding 111 (11.35 g) as yellowish foam.

(1S,2S)-(+)-3-[(4,4'-Dimethoxytrityl)oxy]-2-[ε-(N-cholesteryloxycarbonylamino)-caproylamino]-1-phenylpropanol 1-O-(2cyanoethyl diisopropylphosphoramidite) (112) To the solution of the compound 111 (9.95 g, 10 mmol) in CH2Cl2 (75 ml) were added (iPr)₂NEt (3.50 ml, 20 mmol) and 2-cyanoethyl-N,N'-diisopropylaminochlorophosphine (2.90 ml, 13 mmol) under Ar. The reaction mixture was stirred at room temperature for 1 h and was then diluted by adding CH₂Cl₂ (100 ml). The solution was poured into 5% NaHCO₃ aqueous solution (200 ml), shaken and separated. The aqueous layer was extracted with CH₂Cl₂ (150 ml). The combined organic layer was washed with 5% NaHCO₃ aqueous solution (2×100 ml) and saturated NaCl aqueous solution (3×100 ml), dried over Na₂SO₄. The solid was filtered out. The filtrate was evaporated to dryness. The residue was applied to FC (silica gel, column 5×15 cm):

CH₂Cl₂/Me₂CO (95:5), 1000 ml, yielding 112 (6.88 g, 58%) as colorless foam.

Scheme 11

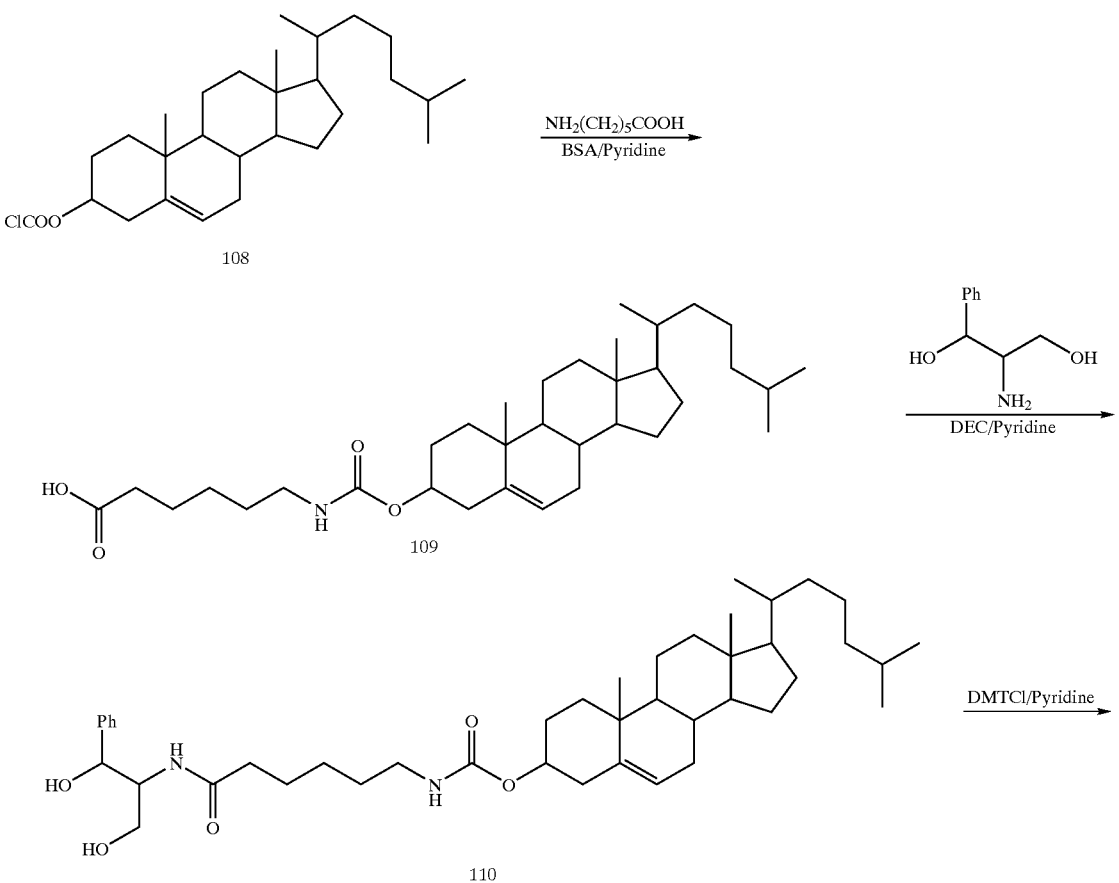

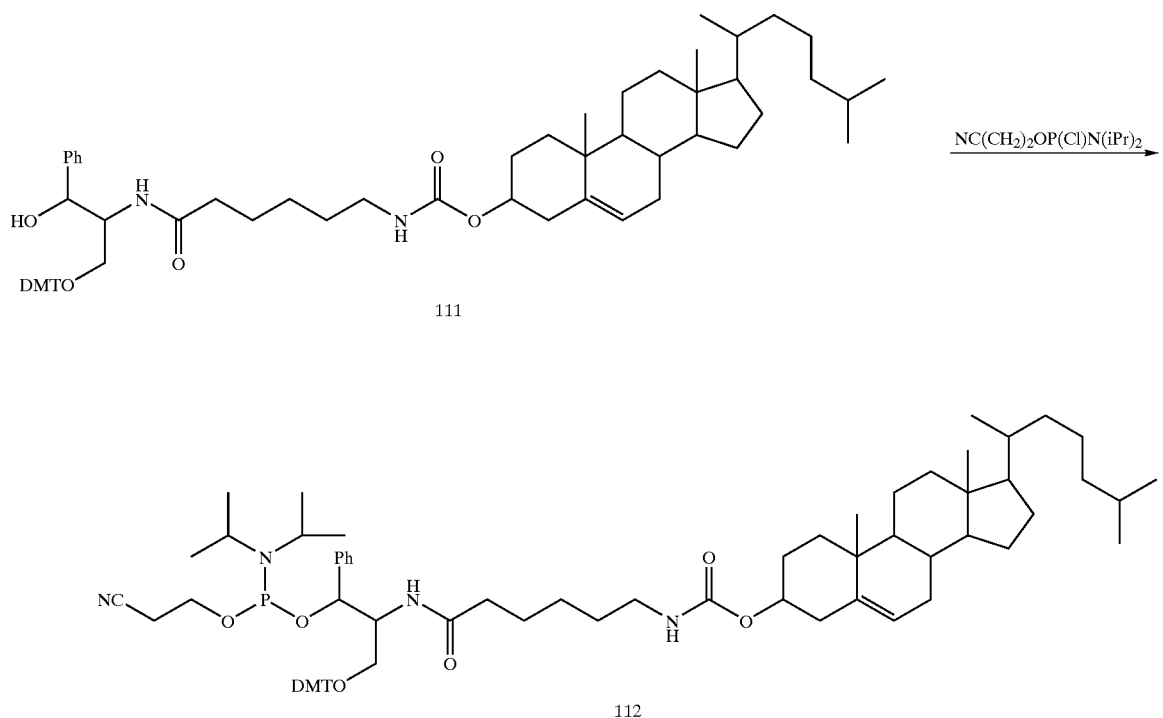

BSA Bis(trimethylsilyl)acetamide, DEC 1-(3-Dimethylamino-propyl)-3-ethylcarbodiimide hydrochloride

Example 27

Synthesis of Solid Support with Immobilized Cholesterol (1S,2S)-(+)-3-[(4,4'-Dimethoxytrityl)oxy]-2-[ε-(N-cholesteryloxycarbonylamino)-caproylamino]-1-phenylpropanyl succinate (113) Referring to Scheme 12, to the solution of the compound 111 (3.98 g, 4 mmol) were added DMAP (0.38 g, 3.2 mmol), succinic anhydride (0.6 g, 6 mmol), and Et$_3$N (0.54 ml, 4 mmol). The reaction mixture was stirred at room temperature for 3.5 h. The solution was diluted by CH$_2$Cl$_2$ (150 ml). It was then washed with 10% citric acid aqueous solution (2×150 ml) and saturated NaCl aqueous solution (2×150 ml), dried (Na$_2$SO$_4$), evaporated to dryness giving a yellow foam (4.33 g).

Polymer Support (114)

(i) CPG Support: To the mixture of the compound 113 (0.5 g, 0.45 mmol), DMAP (0.58 g, 4.5 mmol), and MeCN (2.5 ml) was added the solution of DTNP (0.14 g, 0.45 mmol) in MeCN (1.8 ml) and 1,2-dichloroethane (0.7 ml). After the mixture was stirred at room temperature under nitrogen for 10 min. the solution of TPP (0.12 g, 0.45 mmol) in MeCN (1.2 ml) was added. The stirring was continued for another 10 min. To the mixture resin LCA-CPG (initial loading of NH2: 118.9 μmol/g, 1.90 g, 0.225 mmol) was added. The mixture was shaken at room temperature for 5 h. and then filtered. The solid residue (resin) was washed alternatively with CH$_3$CN (3×10 ml), CH$_2$Cl$_2$ (3×10 ml), and Et$_2$O (3×10 ml). After drying the resin was capped with Cap A for 30 min followed by washing with CH$_2$Cl$_2$ (2×10 ml). It was subsequently capped with Cap B for 30 min. After washing with CH$_2$Cl$_2$ (2×10 ml) and Et$_2$O (2×10 ml), the resin was dried in high vacuum at room temperature overnight yielding polymer support. Loading of the cholesterol (35.2 μmol/g) was observed by determination of released DMT absorption at 498 nm.

(ii) Prime Support: The compound 113 (1.28 g, 1.17 mmol) and HATU (0.45 g, 1.17 mmol) were dissolved in anhydrous DMF (18 ml). To the solution (iPr)$_2$Net (0.53 ml, 3.13 mmol) was added. The mixture was shaken for 5 min and the resin (4g, Primer Support 30, HL, Aminoderivatised Version, Pharmacia Biotech, original loading 146 μmol/g) was added. The reaction mixture was shaken at room temperature for 40 h. It was filtered and the residue was washed with DMF (4×20 ml) followed by CH$_2$Cl$_2$ (3×20 ml), dried in high vacuum for 2.5 h. The unreacted amino function was capped with Cap A for 30 min. The resin was washed with CH$_2$Cl$_2$ (3×20 ml). It was then capped with Cap B for 30 min. followed by washing with CH$_2$Cl$_2$ (3×20 ml). The residue was dried in high vacuum at room temperature for 24 h. yielding the polymer support (4.44 g, loading of cholesterol 51.4 μmol/g).

Scheme 12

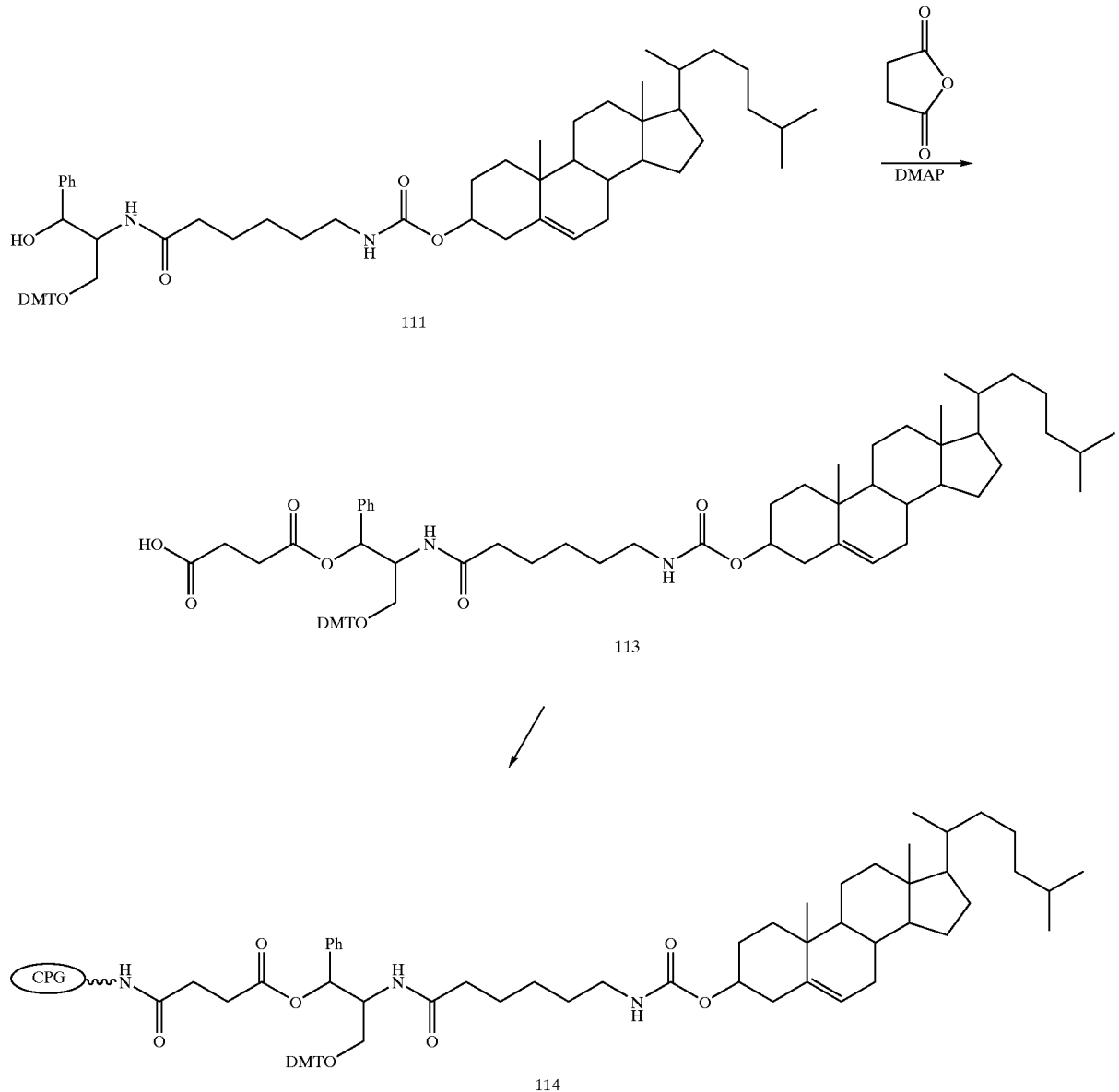

Example 28
Phosphoramidite Derived from Dihexadecylglycerol Containing Non-nucleosidic Linker Referring to Scheme 13, compound 115 (6.98 g, 8.2 mmol) was co-evaporated with anhydrous pyridine three times and then dissolved in pyridine (40 ml). To this solution DMTCl (3.34 g, 9.8 mmol) was added under stirring at room temperature in three portions over 7 h. The reaction mixture was stirred at room temperature for another 15 h. The excess DMTCI was decomposed by adding MeOH (20 ml). The solution was poured into a saturated $NaHCO_3$ aqueous solution (400 ml), shaken and separated. The aqueous layer was extracted with $CH_2Cl_2$ (3×120 ml). The combined organic layer was washed with a saturated NaCl aqueous solution (3×200 ml) and then dried over $Na_2SO_4$. The solid was filtered out. The filtrate was evaporated to dryness giving a gel, which was applied, to a silica gel, column 12×20 cm. The column was eluted with $CH_2Cl_2$/MeOH (95:5 containing drops of $Et_3N$) furnishing compound 116 (6.89 g, 73%) as colorless foam.

Compound (117) To the solution of the compound 116 (3.44 g, 3 mmol) in anhydrous $CH_2Cl_2$ (25 ml) were added $(iPr)_2$Net (1.05 ml, 6 mmol) and 2-cyanoethyl-N,N'-diisopropylaminochlorophosphine (0.87 ml, 3.9 mmol) under Ar. The reaction mixture was stirred at room temperature for 1 h. It was then poured into 5% $NaHCO_3$ aqueous solution, shaken and separated. The aqueous layer was extracted with $CH_2Cl_2$ (3×60 ml). The combined organic layer was washed with 5% $NaHCO_3$ aqueous solution (100 ml) and saturated NaCl aqueous solution (2×120 ml), dried over $Na_2SO_4$. The solid was filtered out. The filtrate was evaporated to dryness giving a gel that was further dried in high vacuum furnishing a yellow foam (4.77 g). It was applied to FC (silica gel, column 5×15 cm): $CH_2Cl_2/Me_2CO$ (9:1), 2000 ml, yielding 117 (1.0 g) as colorless foam. Also, the starting material 116 (1.0 g) was recovered.

Scheme 13

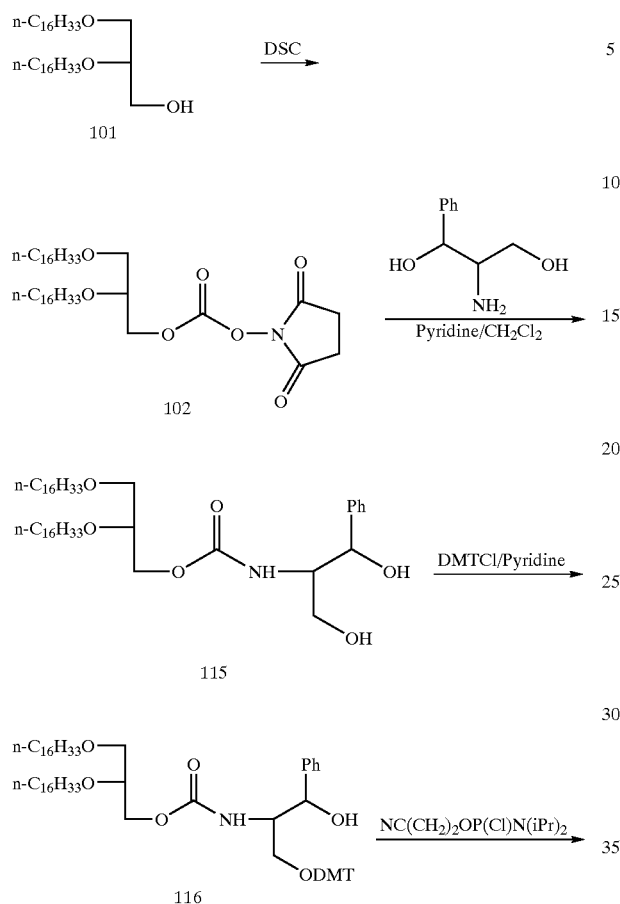

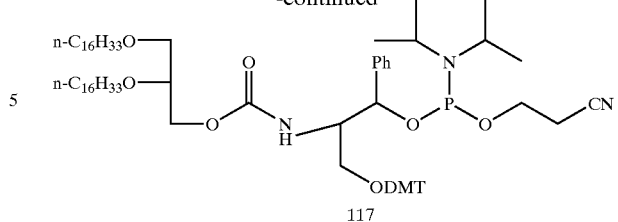

DSC: Disuccinimidyl carbonate

Example 29

Figure 2:
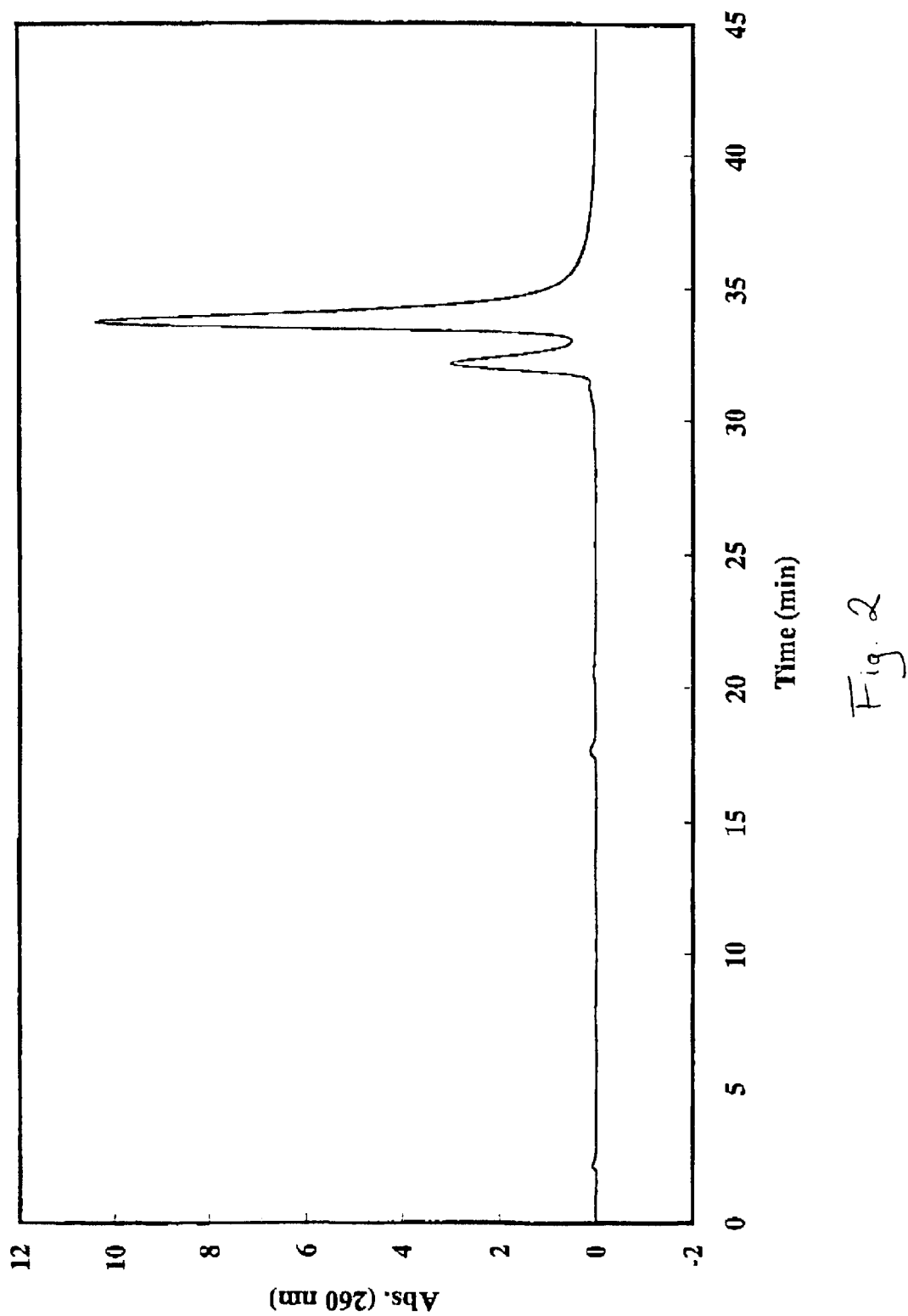
FIG. 2 is an RP HPLC profile of compound 120 in its crude form after removal of the DMT group.
Figure 3:
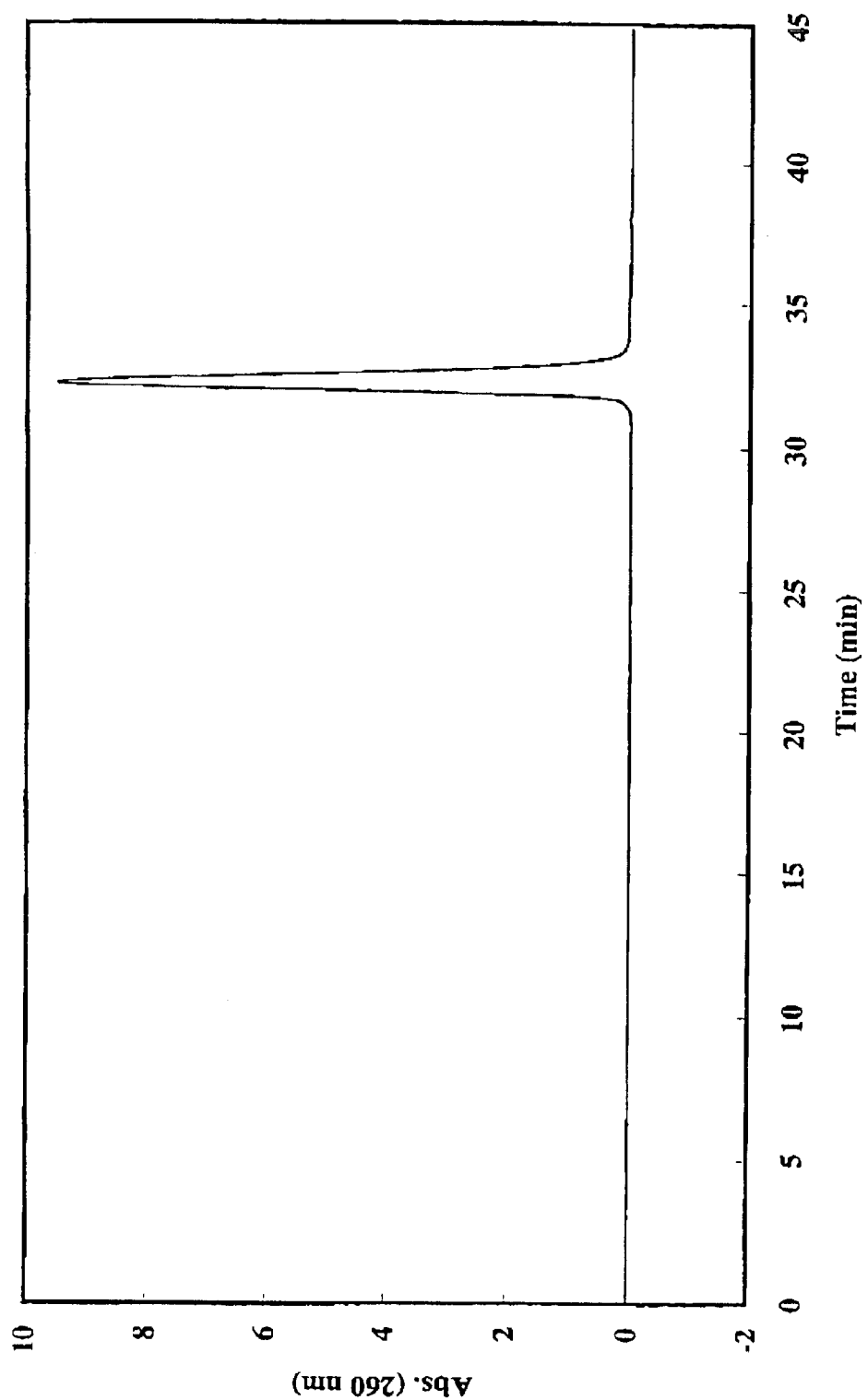
FIG. 3 is an RP HPLC profile of compound 120 in its final form.
Figure 4:
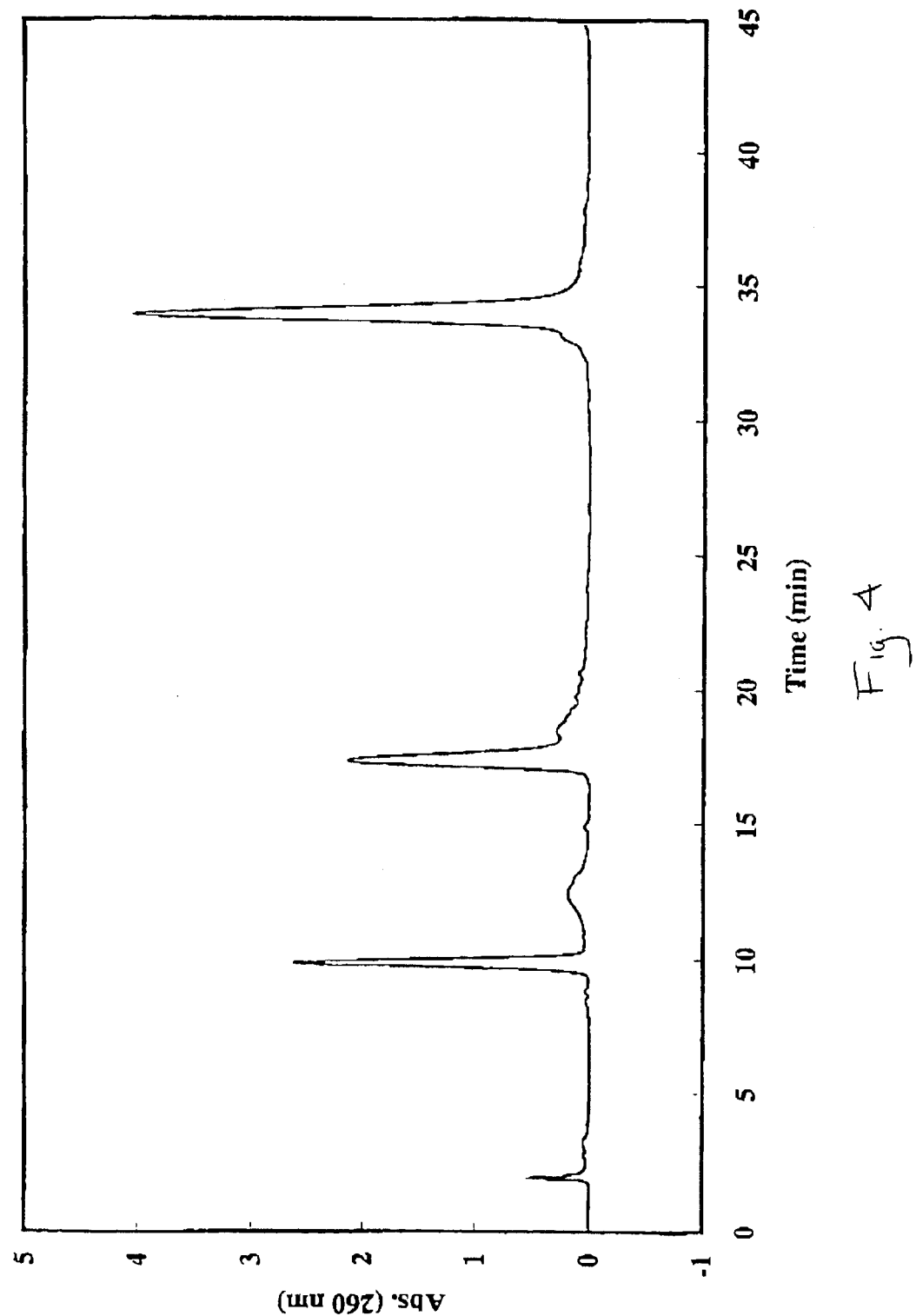
FIG. 4 is an RP HPLC profile of compound 129 in its crude form prior to removal of the DMT group.
Figure 5:
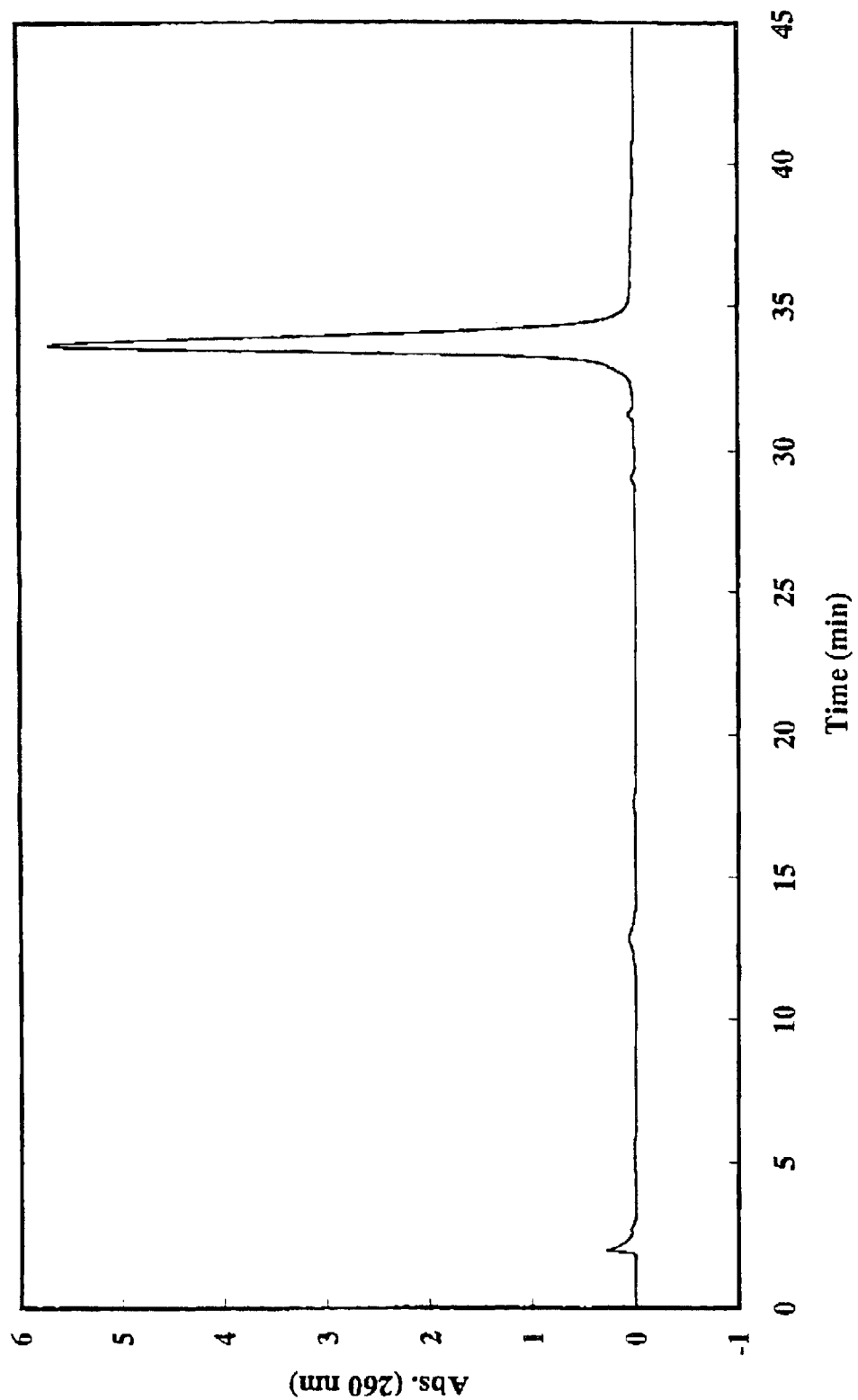
FIG. 5 is an RP HPLC profile of compound 129 in its crude form after removal of the DMT group.
Figure 6:
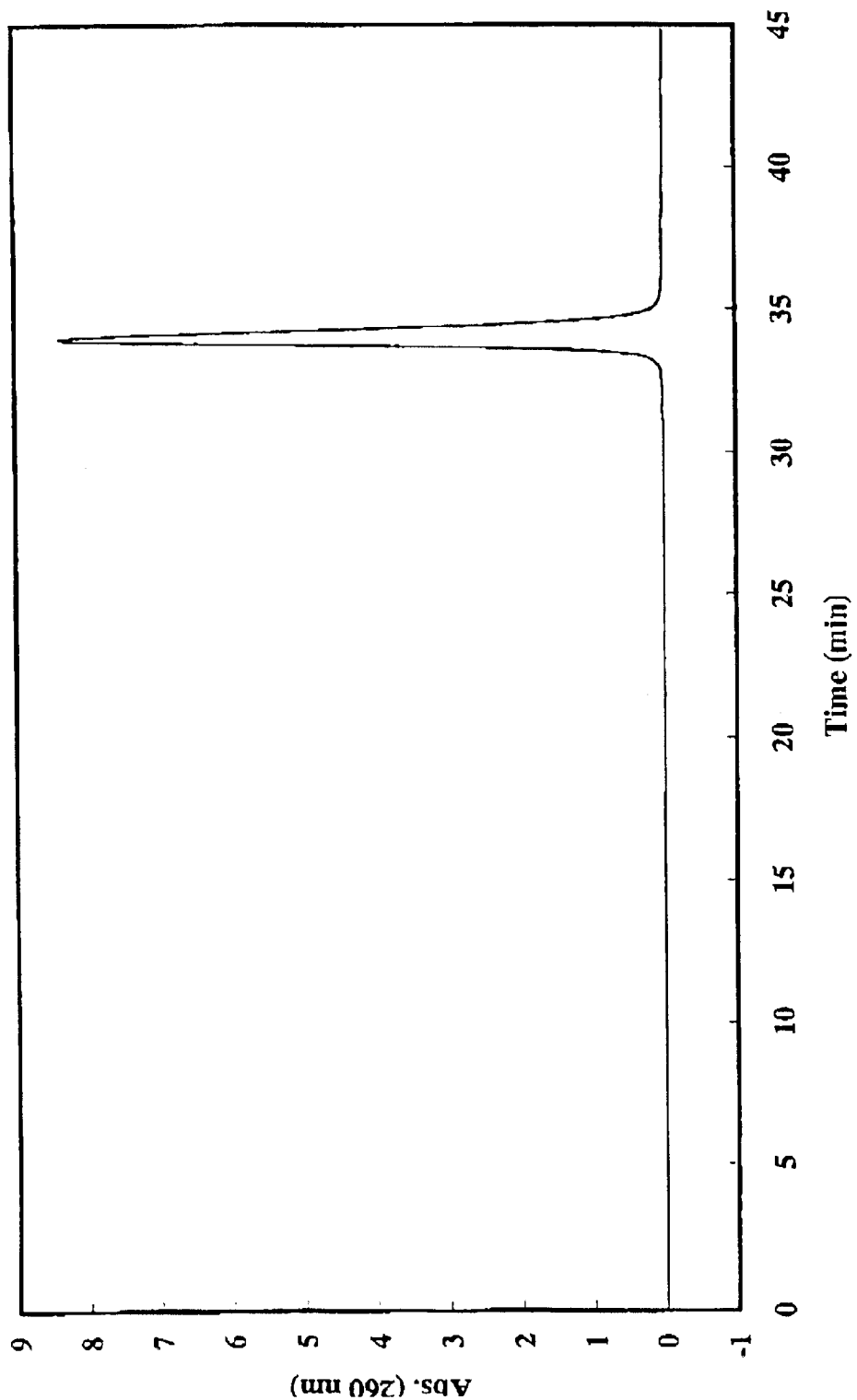
FIG. 6 is an RP HPLC profile of compound 129 in its final form.
Figure 7:
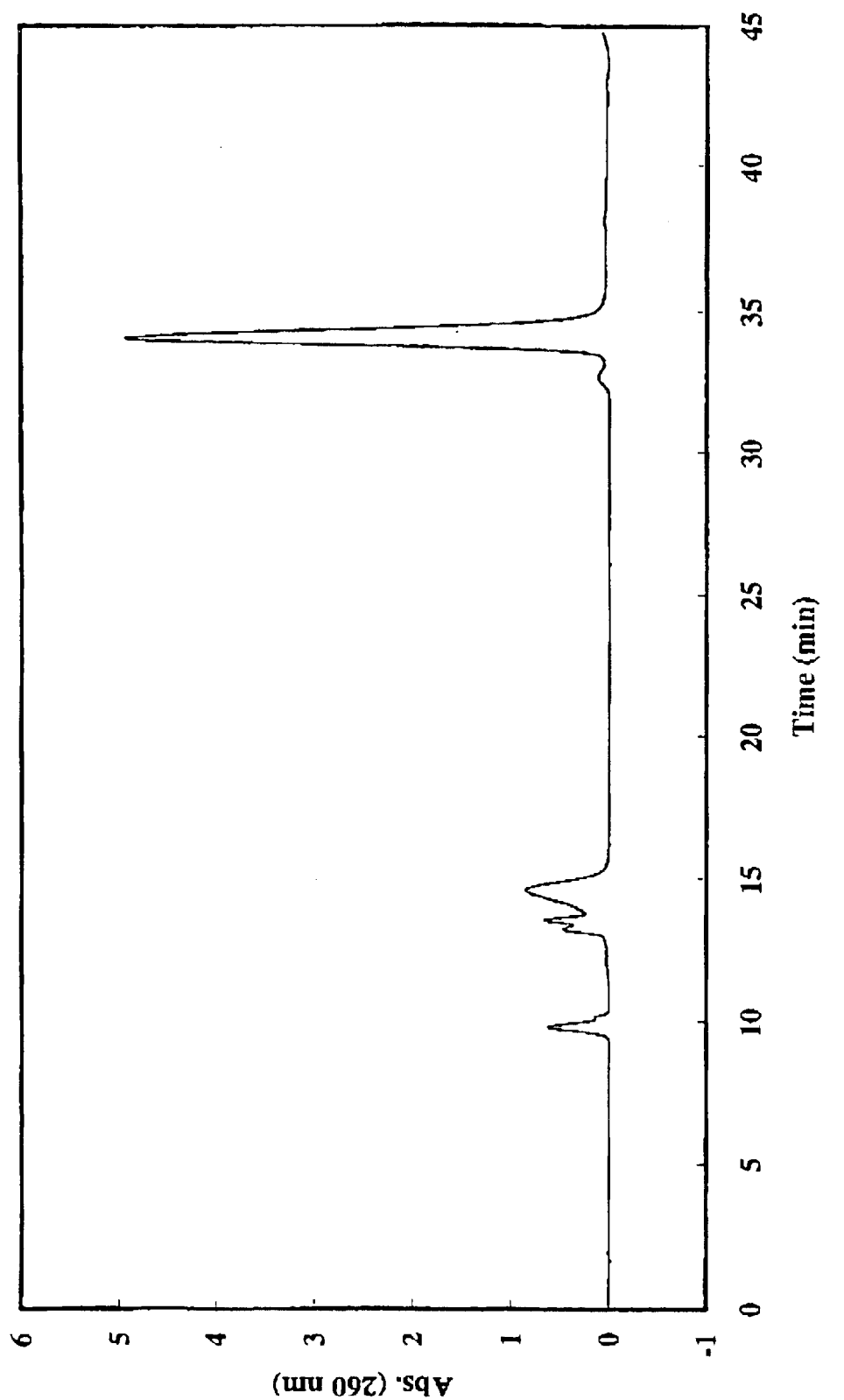
FIG. 7 is an RP HPLC profile of compound 126 in its crude form after removal of the DMT group.
Figure 8:
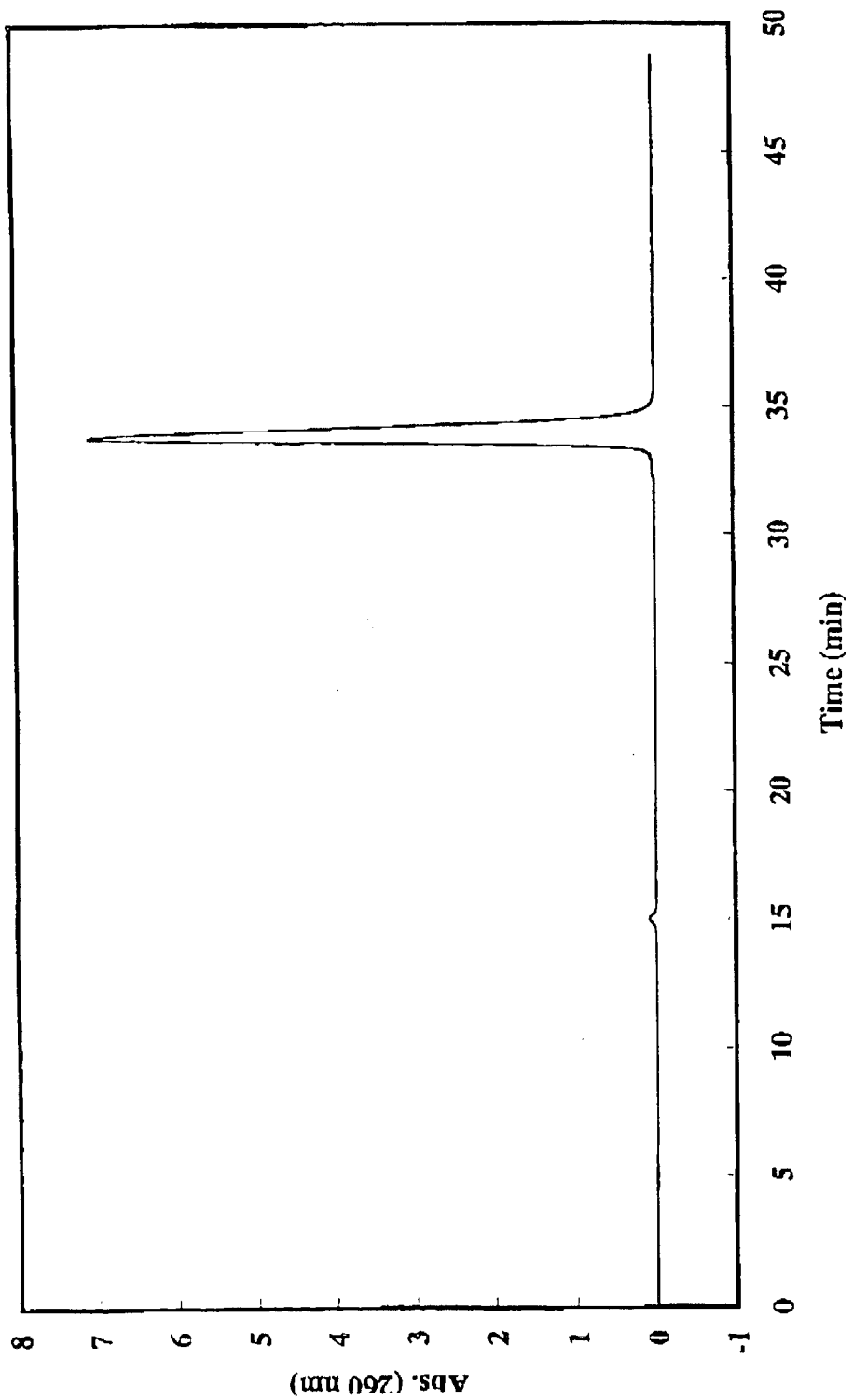
FIG. 8 is an RP HPLC profile of compound 126 in its final form.
Figure 9:
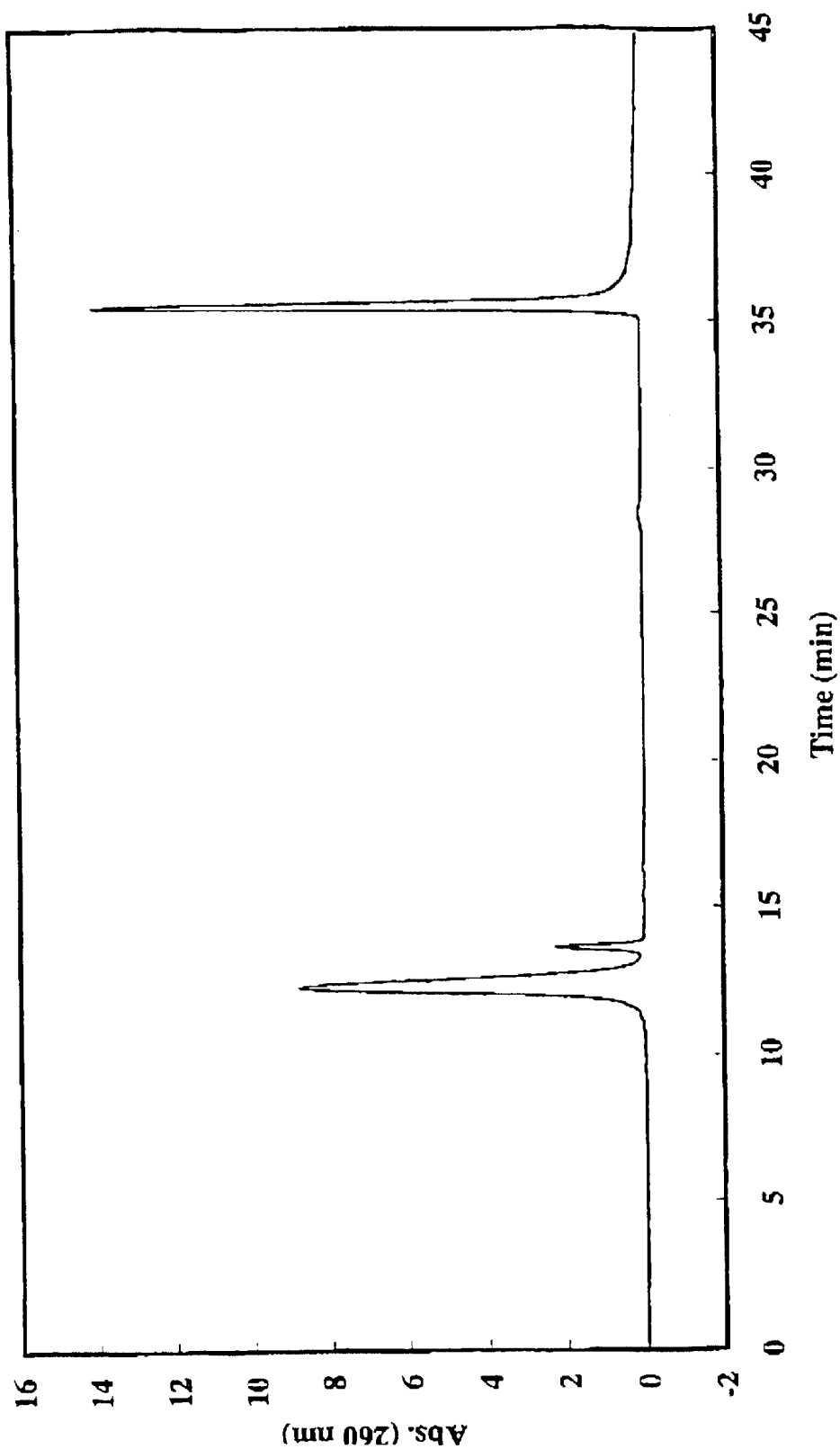
FIG. 9 is an RP HPLC profile of compound 121 in its crude form after removal of the DMT group.
Figure 10:
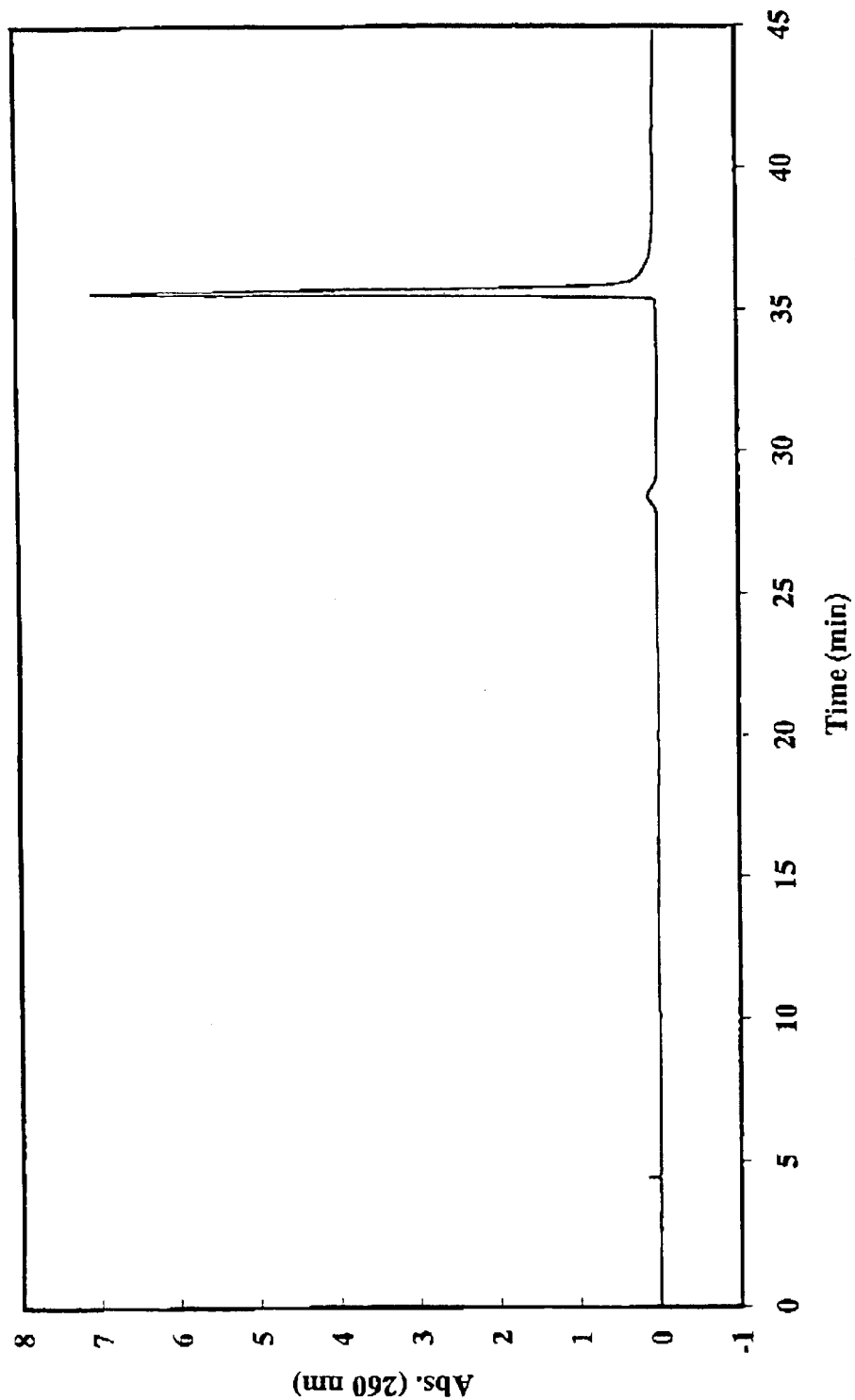
FIG. 10 is an RP HPLC profile of compound 121 in its final form.

The cholesterol- and dialkylglycerol-conjugated oligonucleotides, compounds 120–129, presented in the Tables 6–9 below were prepared using the phosphoramidites and solid support described above in connection with Examples 27 and 28. The RP HPLC profiles of compound 120 in its crude form prior to removal of the DMT group, in its crude form after removal of the DMT group, and in its final form are shown in FIGS. 1–3, respectively. The RP HPLC profiles of compound 129 in its crude form prior to removal of the DMT group, in its crude form after removal of the DMT group, and in its final form are shown in FIGS. 4–6, respectively. The RP HPLC profiles of compound 126 in its crude form after removal of the DMT group and in its final form are shown in FIGS. 7 and 8, respectively. The RP HPLC profiles of compound 121 in its crude form after removal of the DMT group and in its final form are shown in FIGS. 9 and 10, respectively.

Compound 120

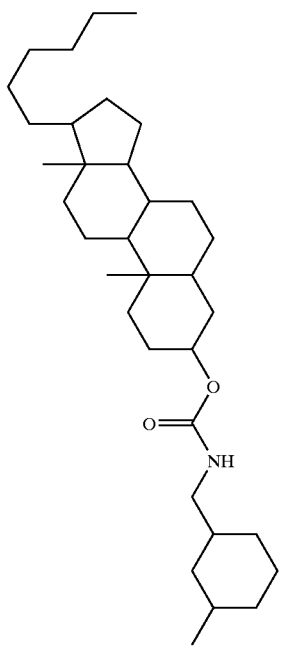

-continued
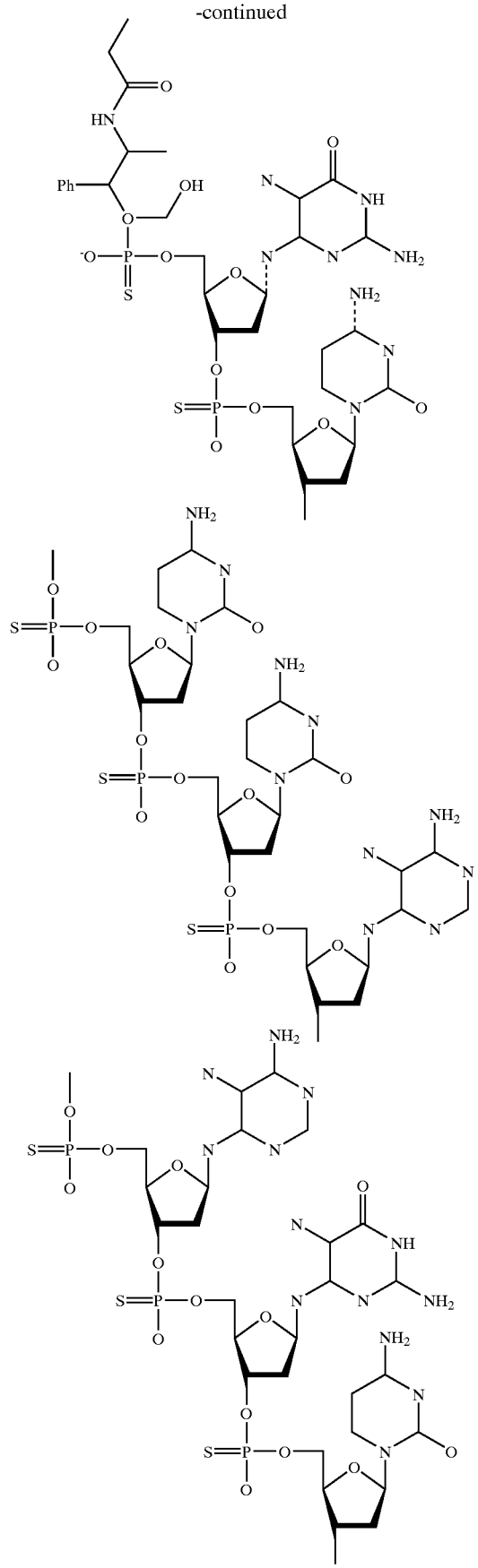

-continued
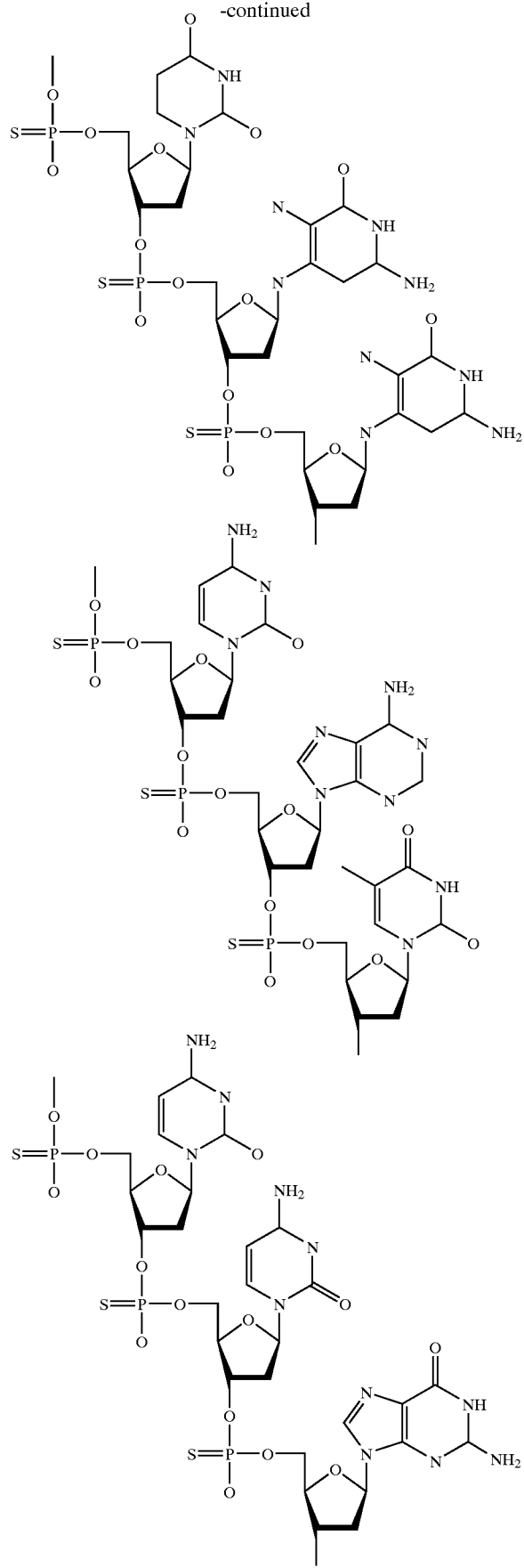

-continued
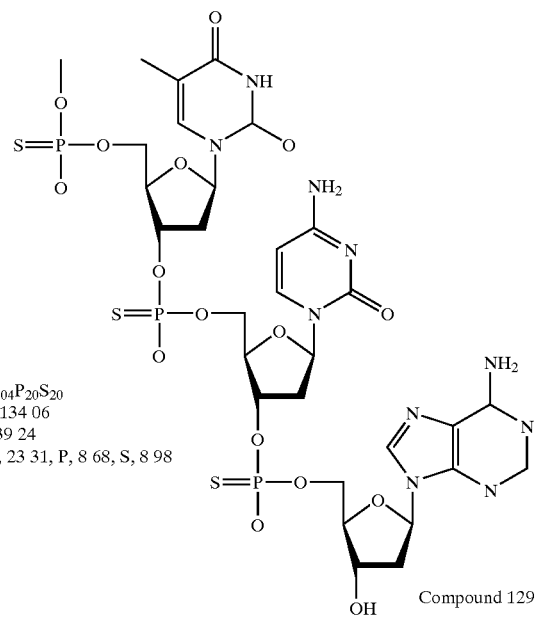
$C_{235}H_{311}N_{77}O_{104}P_{20}S_{20}$
Exact Mass 7134.06
Mol Wt 7139.24
C, 39.54, H, 4.39, N, 15.11 O, 23.31, P, 8.68, S, 8.98
Compound 129
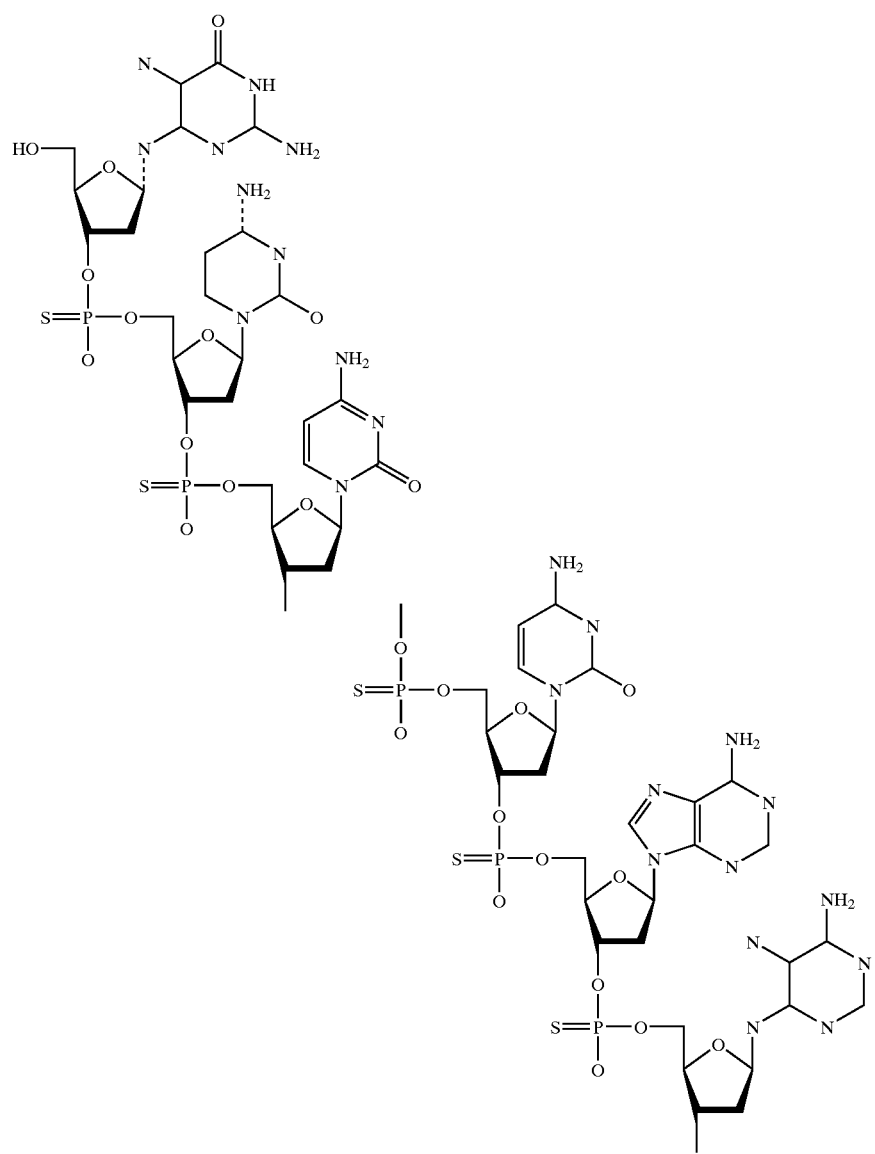

-continued
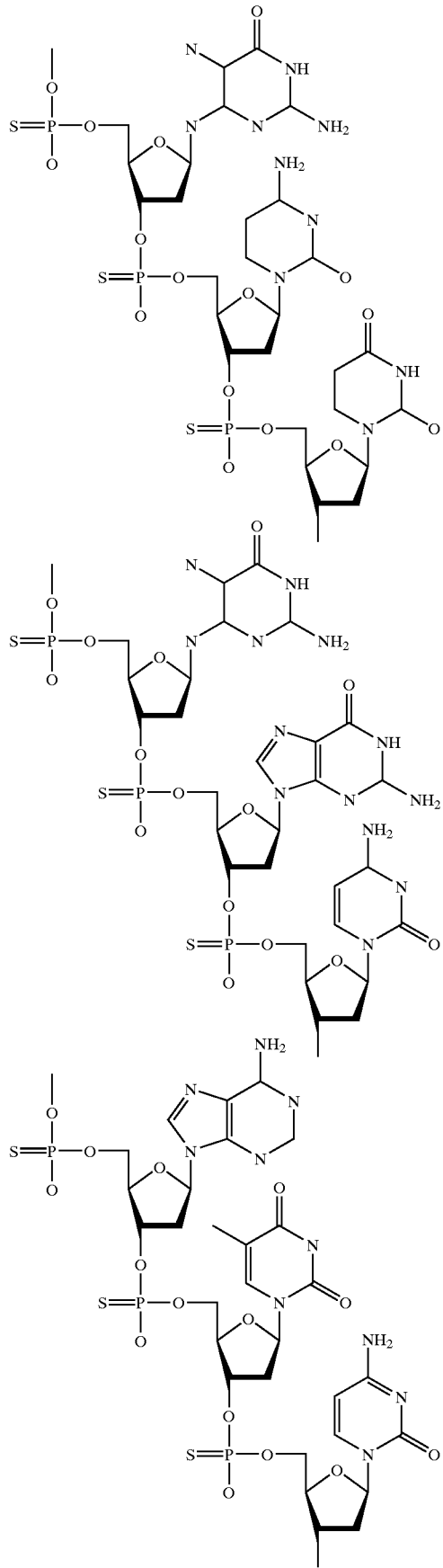

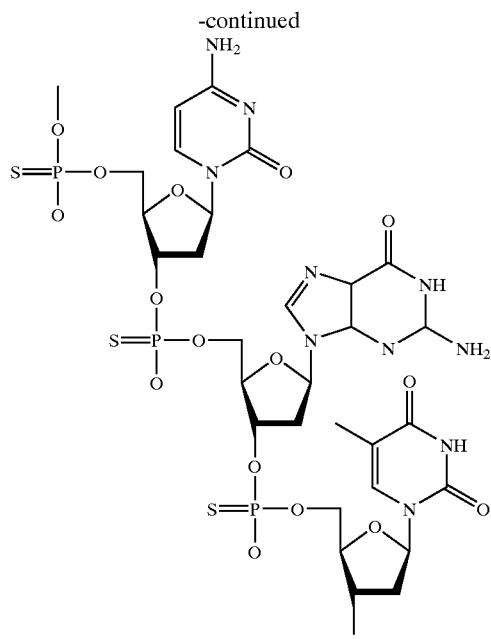
$C_{235}H_{311}N_{77}O_{104}P_{20}S_{20}$
Exact Mass: 7134.06
Mol. Wt.: 7139.24
C, 39.54; H, 4.39; N, 15.11; O, 23.31; P, 8.68; S, 8.98
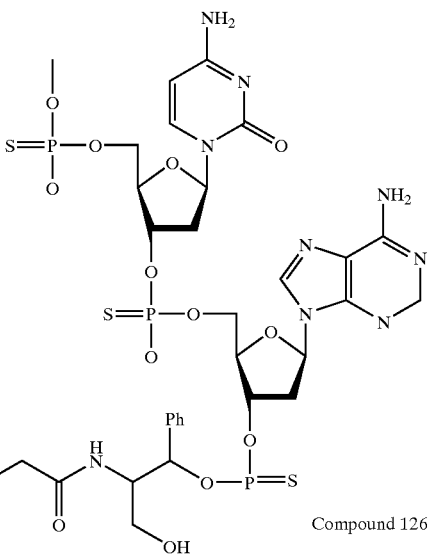
Compound 126
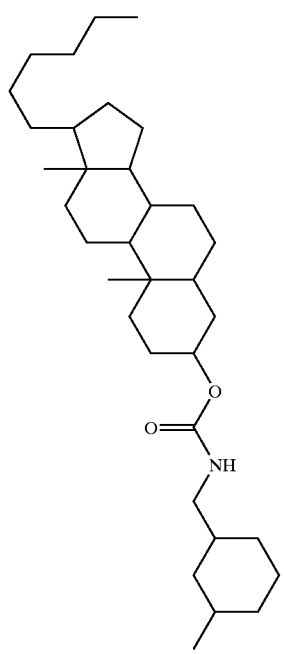

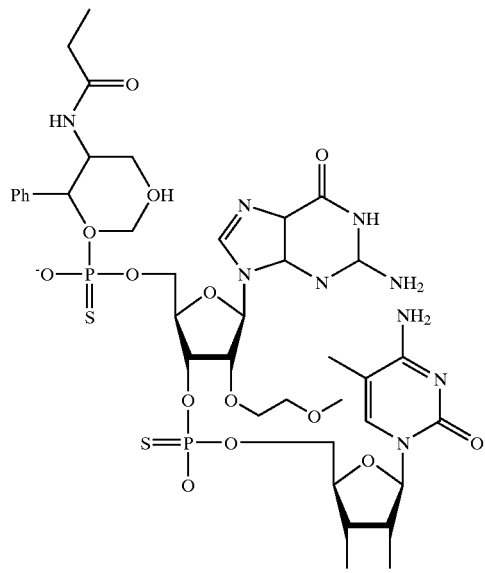
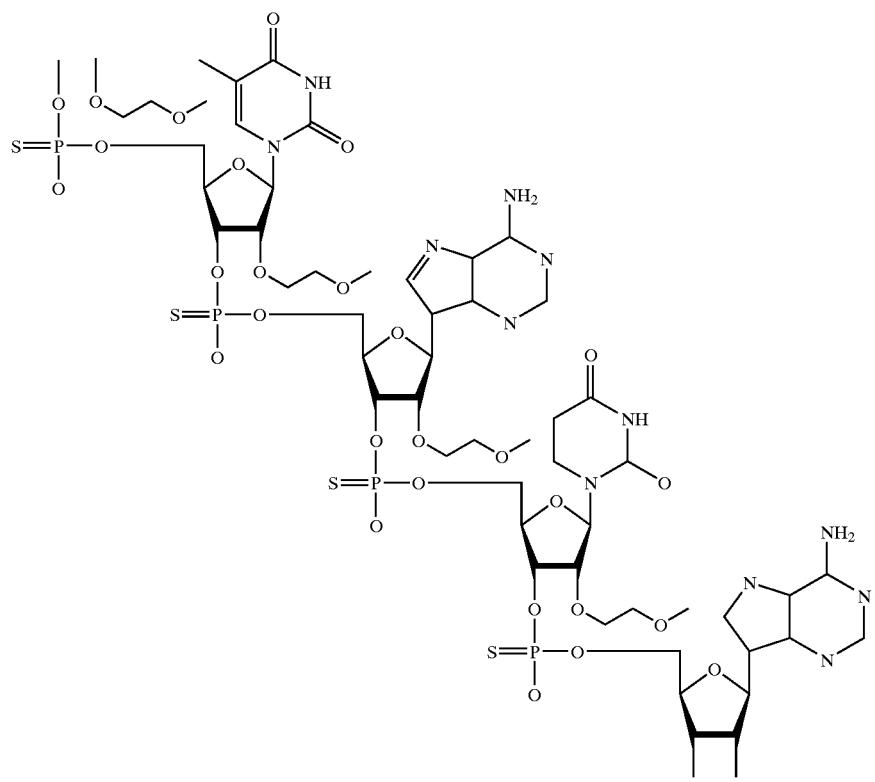

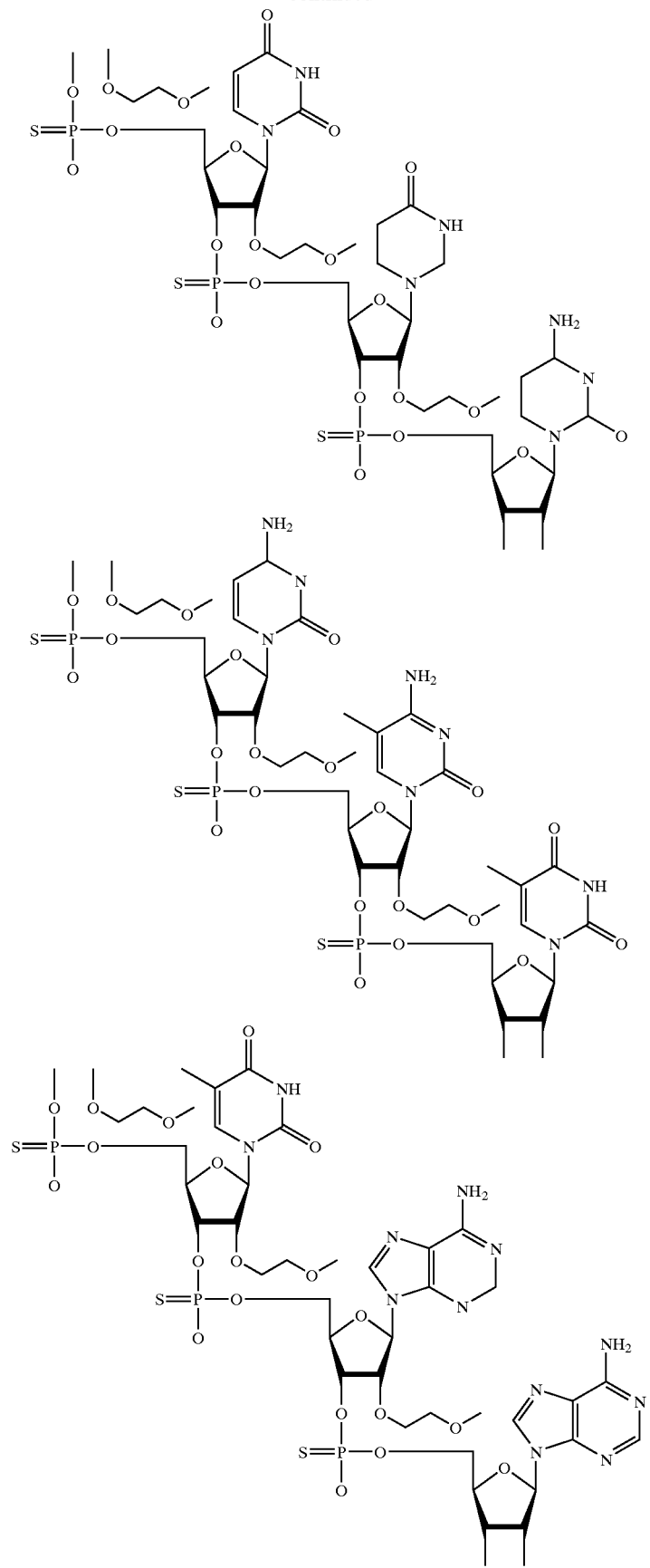

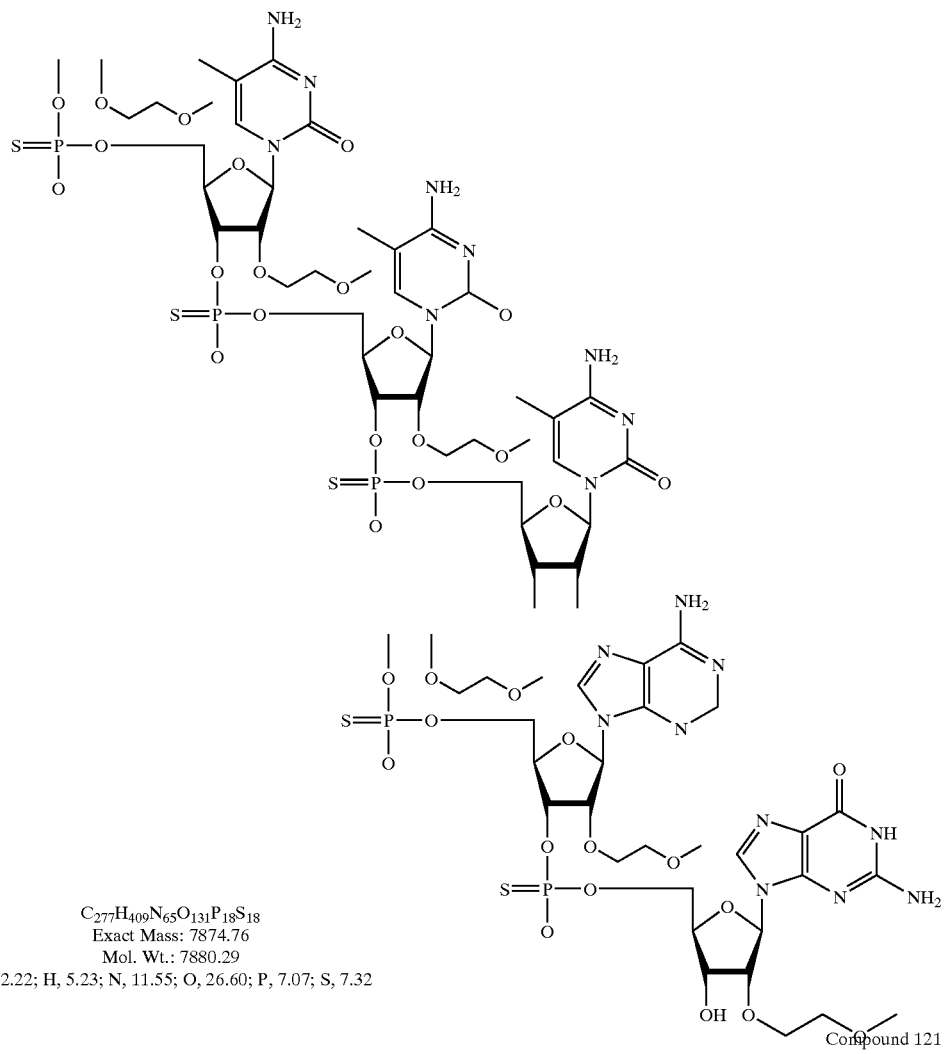
C₂₇₇H₄₀₉N₆₅O₁₃₁P₁₈S₁₈
Exact Mass: 7874.76
Mol. Wt.: 7880.29
C, 42.22; H, 5.23; N, 11.55; O, 26.60; P, 7.07; S, 7.32
Compound 121
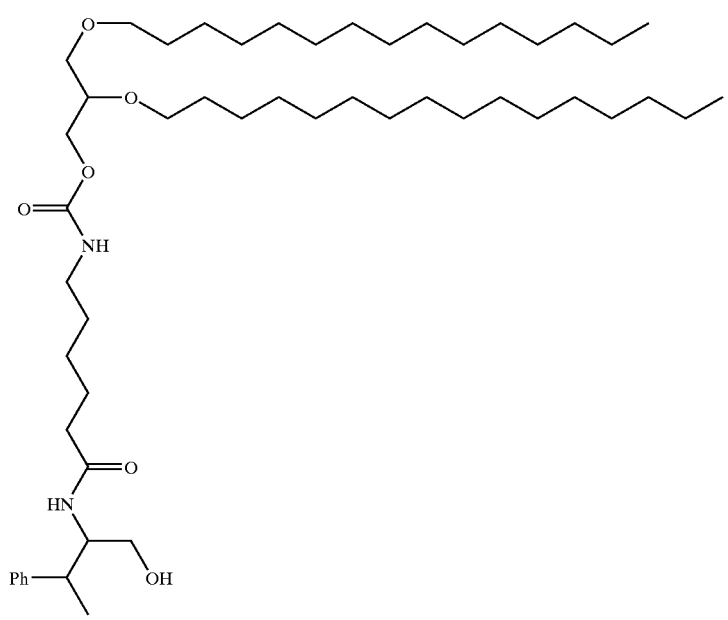

-continued
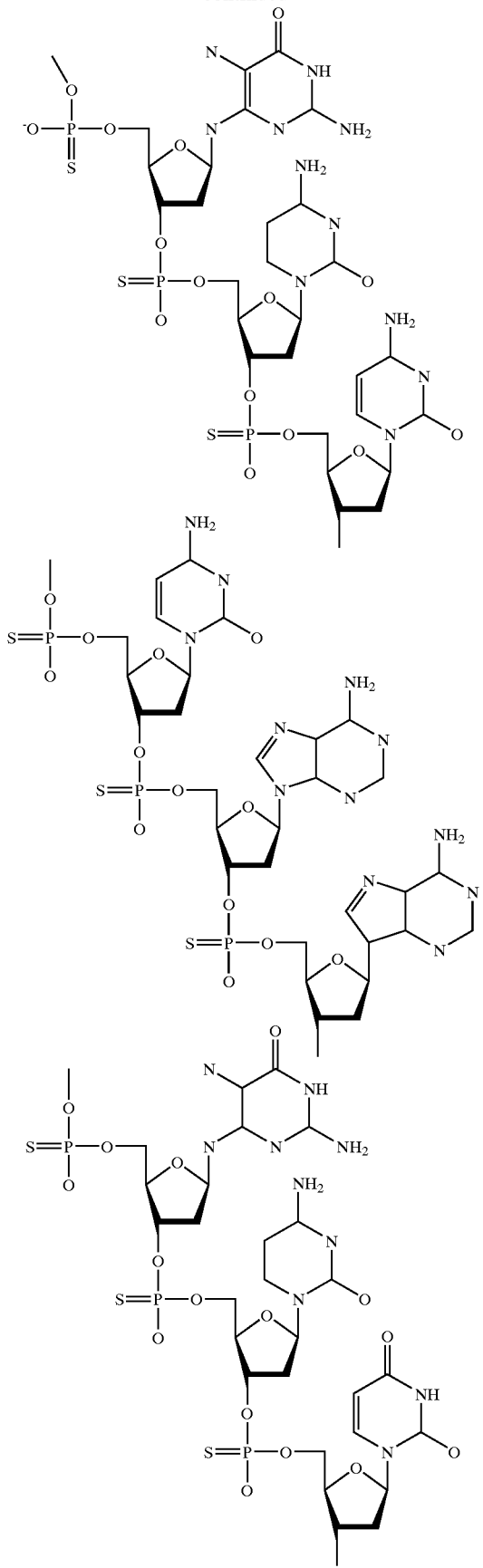

-continued
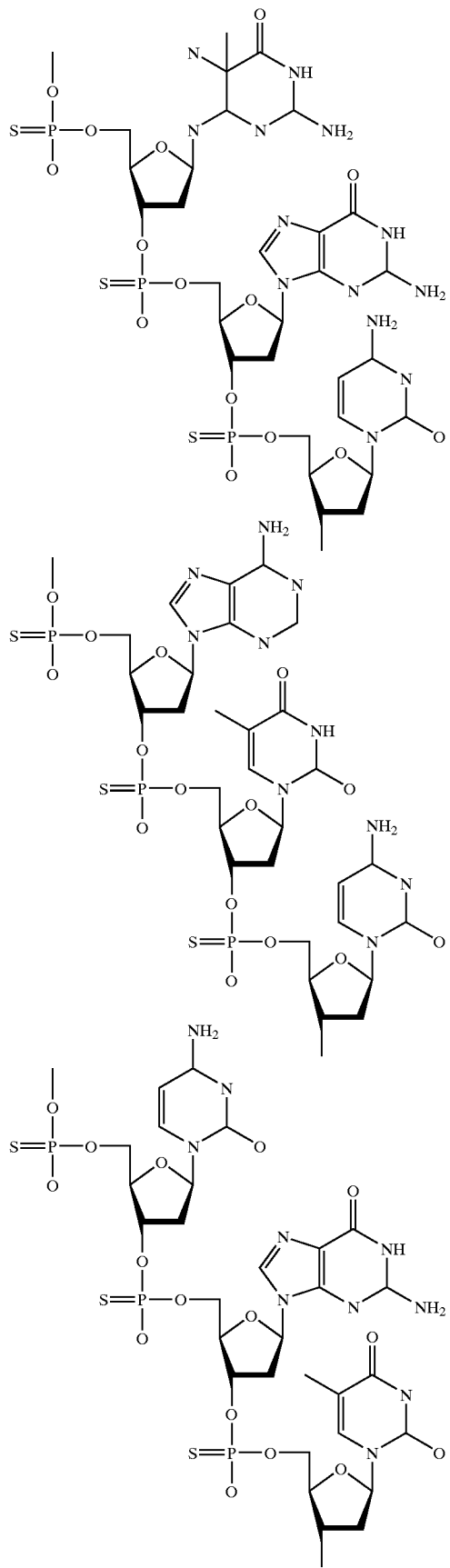

-continued

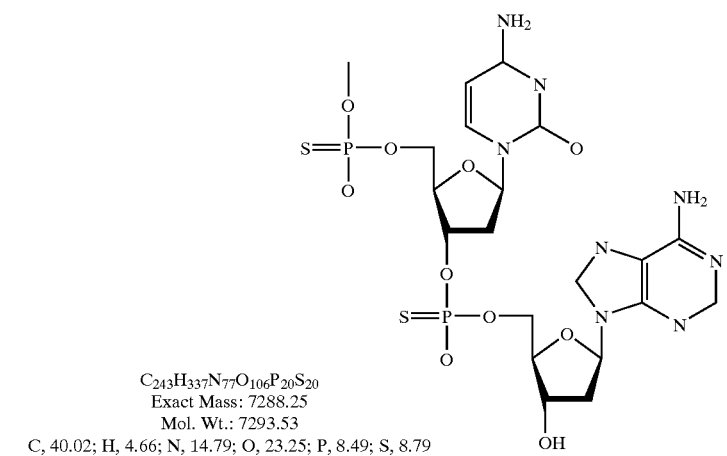

$C_{243}H_{337}N_{77}O_{106}P_{20}S_{20}$
Exact Mass: 7288.25
Mol. Wt.: 7293.53
C, 40.02; H, 4.66; N, 14.79; O, 23.25; P, 8.49; S, 8.79

TABLE 6

Cholesterol-/Dialkylglycerol-Conjugated Oligonucleotides (1)

| Cmpd. | Sequence (5'-3') | Backbone | Quantity (ODs at 260 nm) | Molecular Weight calc. | Molecular Weight found | More Information |
|---|---|---|---|---|---|---|
| 120 | Chol-5'-d(GCC CAA GCT GGC ATC CGT CA) <SEQ. ID. NO. 12> | P=S | 58 mg (880 OD) | 7139 | 7137 | ICAM-1 |
| 121 | Diag-5'-d(GCC CAA GCT GGC ATC CGT CA) <SEQ. ID. NO. 12> | P=S | 46 mg (816 OD) | 7293 | 7290 | ICAM-1 |

Note: (1) Chol: Cholesterol and Linker, see structure. (2) Diag: Dialkylglycerol and Linker, see structure.

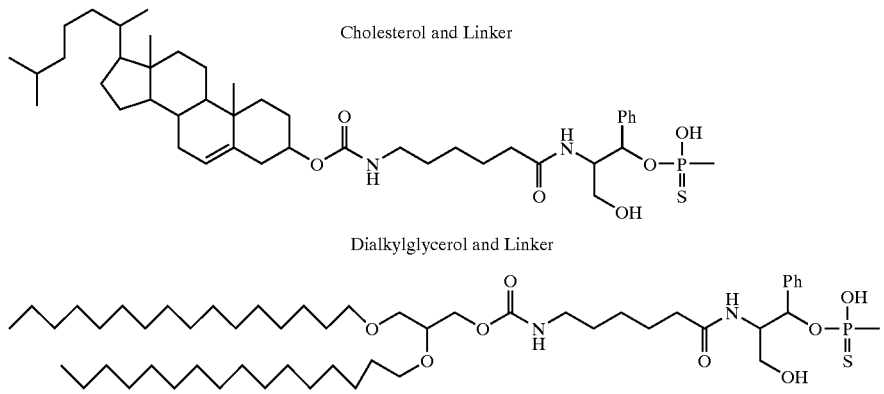

Cholesterol and Linker

Dialkylglycerol and Linker

TABLE 7

Cholesterol-Conjugated Oligonucleotides (2)

| Cmpd. | Sequence(5'-3') | Backbone | Quantity (ODs at 260 nm) | Molecular Weight calc. | Molecular Weight found | More Information |
|---|---|---|---|---|---|---|
| 122 | Chol-5'-d(tcc GTC ATC GCT cct cag gg) <SEQ. ID. NO. 13> | P=S | 25 mg (456 OD) | 8006 | 8006 | Ras-Ha |
| 123 | Chol-5'-d(gtc caC CAT TAG CAC gcg gg) <SEQ. ID. NO. 14> | P=S | 42 mg (727 OD) | 7962 | 7961 | TGF-β |
| 124 | Chol-5'-d(gtc caC* C*AT TAG C*AC* gcg gg) <SEQ. ID. NO. 15> | P=S | 42mg (789 OD) | 8018 | 8018 | TGF-β |

TABLE 7-continued

Cholesterol-Conjugated Oligonucleotides (2)

| Cmpd. | Sequence(5'-3') | Backbone | Quantity (ODs at 260 nm) | Molecular Weight calc. | Molecular Weight found | More Information |
|---|---|---|---|---|---|---|

Note:
(1) Chol: Cholesterol and Linker, see structure.

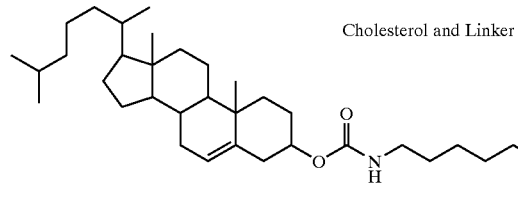

Cholesterol and Linker (2) t: 2'-O-MOE-rT; c: 2'-O-MOE-5-Me-rC;
a: 2'-O-MOE-rA; g: 2'-O-MOE-rG;
C*: 5-Me-dC

TABLE 8

Cholesterol-Conjugated Oligonucleotides (3)

| Cmpd. | Sequence(5'-3') | Backbone | Quantity (ODs at 260 nm) | Molecular Weight calc. | Molecular Weight found | More Information |
|---|---|---|---|---|---|---|
| 125 | Chol-5'-(cct ctt acc tca gtt aca) <SEQ. ID. NO. 16> | P=S | 67 OD | 7845 | 7846 | RNA-splicing |
| 126 | Chol-5'-(gct att acc tta acc cag) <SEQ. ID. NO. 17> | P=S | 70 OD | 7880 | 7881 | RNA-splicing |

Note:
(1) Chol: Cholesterol and Linker, see structure.

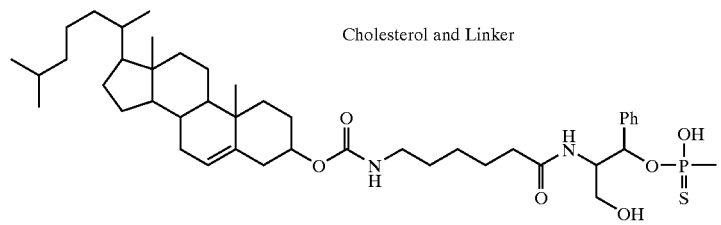

Cholesterol and Linker (2) t: 2'-O-MOE-rT; c: 2'-O-MOE-5-Me-rC;
a: 2'-O-MOE-rA; g: 2'-O-MOE-rG.
Kole705: 5'-(CCU CUU ACC UCA GUU ACA) <SEQ. ID. NO. 20>
Kole654: 5'-(GCU AUU ACC UUA ACC CAG) <SEQ. ID. NO. 21>

TABLE 9

Cholesterol-Conjugated Oligonucleotides (4)

| Compd. | Sequence (5'–3') | Backbone | Quantity | MW calc. | MW Found | More Info |
|---|---|---|---|---|---|---|
| 127 | Chol-5'-d(ctgctAGC*C*TC*TGGAtttga) <SEQ. ID. NO. 18> | P=S | 82 mg | 7986 | 7993 | PTEN |
| 128 | Chol-5'-d(cttctGGC*ATC*C*GGTttaga) <SEQ. ID. NO. 19> | P=S | 84 mg | 7986 | 7994 | PTEN |

TABLE 9-continued

Cholesterol-Conjugated Oligonucleotides (4)

| Compd. | Sequence (5'–3') | Backbone | Quantity | MW calc. | Found | More Info |
|---|---|---|---|---|---|---|

Note:
(1) Chol: Cholesterol and Linker, see structure.

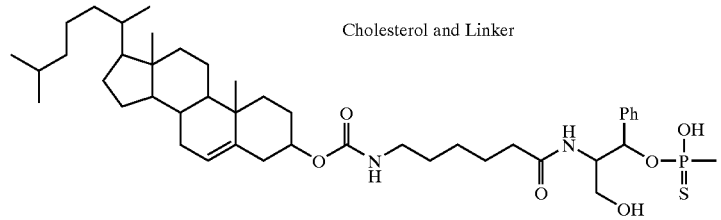

Cholesterol and Linker (2) t: 2'-O-MOE-rT; c: 2'-O-MOE-5-Me-rC;
a: 2'-O-MOE-rA; g: 2'-O-MOE-rG;
C*: 5-Me-dC Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true scope and spirit of the invention.

What is claimed is:

1. A process for preparing an oligonucleotide having the formula:

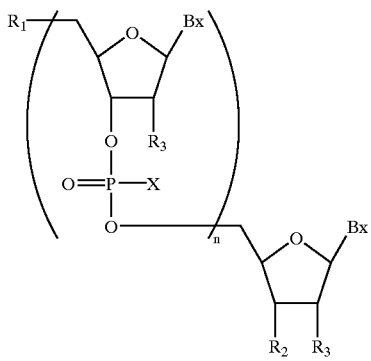

wherein:

$R_1$ is a group having the formula:

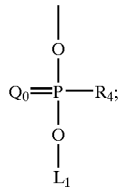

$Q_0$ is O or S;

$R_4$ is O, hydroxyl, or a protected hydroxyl;

$R_2$ is hydroxyl, a protected hydroxyl or a group having the formula:

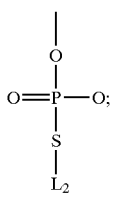

each $R_3$ is H, a 2'-substituent group or a protected 2'-substituent group;

each X is, independently, $O^-$, hydroxyl, protected hydroxyl, or $-S-L_3$;

each Bx is an optionally protected heterocyclic base moiety;

n is from 3 to about 50; and $L_1$, $L_2$ and each of said $L_3$ are, independently, a cholesterol, phospholipid, biotin, phenazine, phenanthridine, anthraquinone, acridine, fluorescein, rhodamine, or coumarin wherein said $R_1$ and at least one of said $R_2$ or said X comprise a cholesterol, phospholipid, biotin, phenazine, phenanthridine, anthraquinone, acridine, fluorescein, rhodamine, or coumarin;

comprising the steps of:

a) providing a derivatized solid support for oligonucleotide synthesis, said derivatized solid support being derivatized with a group having one of the structures;

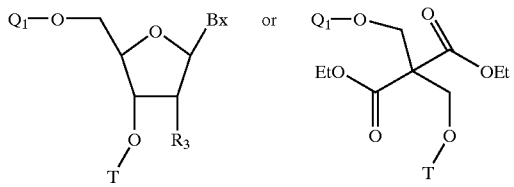

wherein

T is a bifunctional linking moiety linked to the solid support; and $Q_1$ is an acid labile hydroxyl protecting group;

b) treating said derivatized solid support with an acidic reagent to deblock said acid labile hydroxyl protecting group to give a free hydroxyl group;

c) reacting said free hydroxyl group with a phosphoramidite composition to form an extended compound, said phosphoramidite composition having the formula:

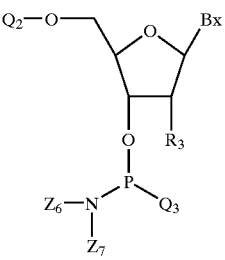

wherein $Q_2$ is a 5'-terminal acid labile hydroxyl protecting group;

$Q_3$ is a phosphorus protecting group; and $Z_6$ and $Z_7$ are, independently, $C_{1-6}$ alkyl;

or $Z_6$ and $Z_7$ are joined together to form a 4- to 7-membered heterocyclic ring system including the nitrogen atom to which $Z_6$ and $Z_7$ are attached, wherein said ring system optionally includes at least one additional heteroatom selected from O, N and S;

d) oxidizing said extended compound to form an oxidized compound, or treating said extended compound with an acidic reagent to deblock said 5'-terminal acid labile hydroxyl protecting group of said extended compound to give a free hydroxyl group and repeating step c) at least one time followed by oxidizing said extended compound to form an oxidized compound;

e) treating said oxidized compound with an acidic reagent to deblock said acid labile hydroxyl protecting group to give a free hydroxyl group and repeating steps c) and d) at least three times to form an extended oxidized compound;

f) treating said extended oxidized compound with a reagent effective to deblock said protected hydroxyl group to give a free hydroxyl group and reacting said free hydroxyl group with a compound of formula:

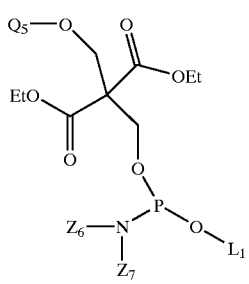

thereby forming a 5'-functionalized compound; wherein $Q_5$ is an acid labile hydroxyl protecting group;

g) treating said 5'-functionalized compound for a time and under conditiong effective to remove at least one phosphorus protecting group giving at least one deblocked phosphorothioate linkage; and h) reacting said deblocked phosphorothioate linkage with a cholesterol, phospholipid, biotin, phenazine, phenanthridine, anthraquinone, acridine, fluorescein, rhodamine, or coumarin, that is reactive with and forms a covalent bond with said deblocked phosphorothioate linkage to give said oligonucleotide.

2. The process of claim 1 further comprising the step of treating said 5'-functionalized compound with a capping agent to form a capped compound.

3. The process of claim 1 wherein said $R_2$ is a group having the formula:

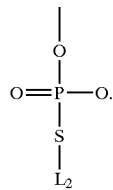

4. The process of claim 3 wherein $L_1$ is different from $L_2$.

5. The process of claim 1 wherein at least one of said X is —S—$L_3$.

6. The process of claim 5 wherein $L_1$ is different from $L_3$.

7. The process of claim 1 wherein each of said $Q_3$ is independently selected from the group consisting of cyanoethyl, diphenylsilylethyl, cyanobutenyl, cyano p-xylyl (CPX), methyl-N-trifluoroacetyl ethyl (META) and acetoxy phenoxy ethyl (APOE) groups.

8. The process of claim 1 wherein said 5'-functionalized compound is treated in step g) to remove all phosphorus protecting groups.

9. The process of claim 1 wherein n is from about 8 to about 30.

10. The process of claim 9 wherein n is from about 15 to about 25.

11. The process of claim 1 wherein each of said $Q_1$ and $Q_2$ is independently selected from the group consisting of trimethoxytrityl, dimethoxytrityl (DMT), monomethoxytrityl, 9-phenylxanthen-9-yl (Pixyl) and 9-(p-methoxyphenyl)xanthen-9-yl (Mox).

12. The process of claim 1 wherein each of said Bx is independently selected from the group consisting of adenine, guanine, thymine, cytosine, uracil, 5-methylcytosine (5-me-C), 5-hydroxymetliyl cytosine, xanthine, hypoxanthine, 2-aminoadenine, alkyl derivatives of adenine and guanine, 2-thiouracil, 2-thiothymine, 2-thiocytosine, 5-halouracil, 5-halocytosine, 5-propynyl uracil, 5-propynyl cytosine, 6-azo uracil, 6-azo cytosine, 6-azo thymine, 5-uracil (pseudouracil), 4-thiouracil, 8-substituted adenines and guanines, 5-substituted uracils and cytosines, 7-methylguanine, 7-methyladenine, 8-azaguanine, 8-azaadenine, 7-deazaguanine, 7-deazaadenine, 3-deazaguanine and 3-deazaadenine.

13. The process of claim 1 wherein at least one of said $L_1$, $L_2$, and $L_3$ is attached to the oligonucleotide through a linking group.

14. The process of claim 13 wherein the linking group comprises a dialkylglycerol linker.

15. The process of claim 1 wherein each of said $Z_6$ and $Z_7$ is isopropyl.

16. The process of claim 1 wherein each $R_3$ is, independently, $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkynyl, O-alkylamino, O-alkylalkoxy, O-alkylaminoalkyl, O-alkyl imidazole, thiol, S-alkyl, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, halogen keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, heterocycle, carbocycle, polyamine, polyamide, polyalkylene glycol, and polyether;

or each substituent group has one of formula I or II:

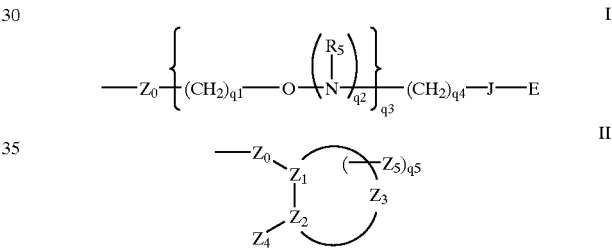

wherein:

$Z_0$ is O, S or NH;

J is a single bond, O or C(=O);

E is $C_1$–$C_{10}$ alkyl, $N(R_5)(R_6)$, $N(R_5)(R_7)$, $N$=$C(R_5)(R_6)$, $N$=$C(R_5)(R_7)$ or has one of formula III or IV;

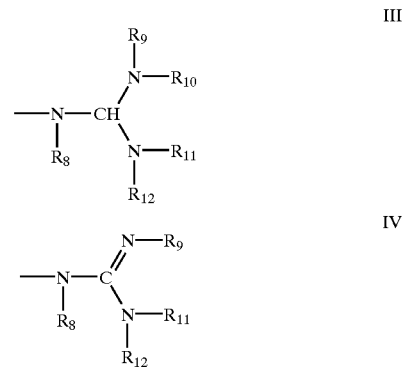

each $R_8$, $R_9$, $R_{10}$, $R_{11}$ and $R_{12}$ is, independently, hydrogen, $C(O)R_{13}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_9$ and $R_{10}$, together form a phthalimido moiety with the nitrogen atom to which they are attached;

or optionally, $R_{11}$ and $R_{12}$, together form a phihalimido moiety with the nitrogen atom to which they are attached;

each $R_{13}$ is, independently, substituted or unsubstituted $C_1$–$C_{10}$ alkyl, trifluoromethyl, cyanoethyloxy, methoxy, echoxy, t-butoxy, allyloxy, 9-fluorenylmethoxy, 2-(trimethylsilyl)-ethoxy, 2,2,2-trichioroethoxy, benzyloxy, butyryl, iso-butyryl, phenyl or aryl;

$R_5$ is T—L,

T is a bond or a linking moiety;

L is a chemical functional group, a conjugate group or a solid support material;

each $R_5$ and $R_6$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_{14})(R_{15})$, guanidino or acyl where said acyl is an acid amide or an ester;

or $R_5$ and $R_6$, together, are a nitrogen protecting group or are joined in a ring structure that optionally includes an additional heteroatom selected from N and O;

or $R_{21}$, T and L, together, are a chemical functional group;

each $R_{14}$ and $R_{15}$ is, independently, H, $C_1$–$C_{10}$ alkyl, a nitrogen protecting group, or $R_{14}$ and $R_{15}$, together, are a nitrogen protecting group;

or $R_{14}$ and $R_{15}$ are joined in a ring structure that optionally includes an additional heteroatom selected from N and O;

$Z_4$ is OX, SX, or $N(X)_2$;

each X is, independently, H, $C_1$–$C_8$ alkyl, $C_1$–$C_8$ haloalkyl, C(=NH)N(H)$R_{16}$, C(=O)N(H)$R_{16}$ or OC(=O)N(H)$R_{16}$;

$R_{16}$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_5)(R_6)$ $OR_5$, halo, $SR_5$ or CN;

each $q_1$ is, independently, an integer from 1 to 10;

each $q_2$ is, independently, 0 or 1;

$q_3$ is 0 or an integer from 1 to 10;

$q_4$ is an integer from 1 to 10;

$q_5$ is from 0, 1 or 2; and provided that when $q_3$ is 0, $q_4$ is greater than 1.

17. A process for preparing an oligonucleotide having the formula:

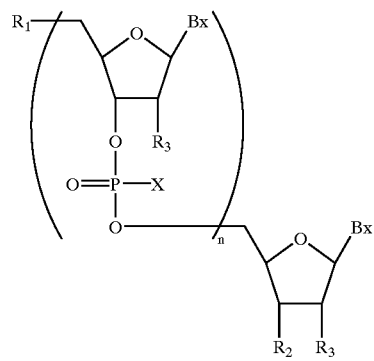

wherein:

$R_1$ is a group having the formula:

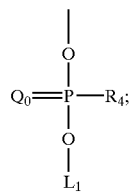

$Q_0$ is O or S;

$R_4$ is O⁻, hydroxyl, or a protected hydroxyl;

$R_2$ is hydroxyl, a protected hydroxyl or a group having the formula:

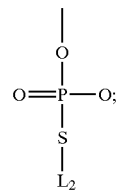

each $R_3$ is H, a 2'-substituen group or a protected 2'-substituent group;

each X is, independently, O⁻, hydroxyl, a protected hydroxyl, or —S—$L_3$;

each Bx is an optionally protected heterocyclic base moiety;

n is from 3 to about 50; and $L_1$, $L_2$ and each of said $L_3$ are, independently, a cholesterol, phospholipid, biotin, phenazine, phenanthridine, anthraquinone, acridine, fluorescein, rhodamine, or coumarin;

comprising the steps of:

a) providing a derivatized solid support for oligonucleotide synthesis, said derivatized solid support being derivatized with a group having one of the structures:

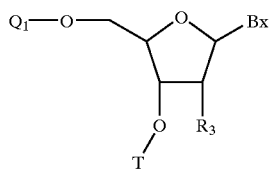

-continued

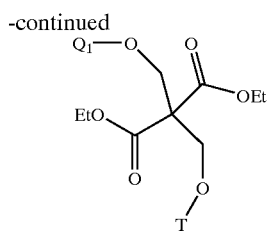

wherein
T is a bifunctional linking moiety linked to the solid support; and
$Q_1$ is an acid labile hydroxyl protecting group;
b) treating said derivatized solid support with an acidic reagent to deblock said acid labile hydroxyl protecting group to give a free hydroxyl group;
c) reacting said free hydroxyl group with a phosphoramidite composition to form an extended compound, said phosphoramidite composition having the formula:

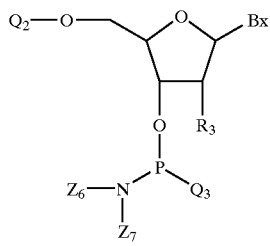

wherein
$Q_2$ is a 5'-terminal acid labile hydroxyl protecting group;
$Q_3$ is a phosphorus protecting group; and
$Z_6$ and $Z_7$ are, independently, $C_{1-6}$ alkyl;
or $Z_6$ and $Z_7$ are joined together to form a 4- to 7-membered heterocyclic ring system including the nitrogen atom to which $Z_6$ and $Z_7$ are attached, wherein said ring system optionally includes at least one additional heteroatom selected from O, N and S;
d) oxidizing said extended compound to form an oxidized compound, or treating said extended compound with an acidic reagent to deblock said 5'-terminal acid labile hydroxyl protecting group of said extended compound to give a free hydroxyl group and repeating step c) at least one time followed by oxidizing said extended compound to form an oxidized compound;
e) treating said oxidized compound with an acidic reagent to deblock said acid labile hydroxyl protecting group to give a free hydroxyl group and repeating steps c) and d) at least three times to form an extended oxidized compound;
f) treating said extended oxidized compound with an acidic reagent effective to deblock said 5'-terminal acid labile hydroxyl protecting group to give a free hydroxyl group and reacting said free hydroxyl group with a compound of the formula:

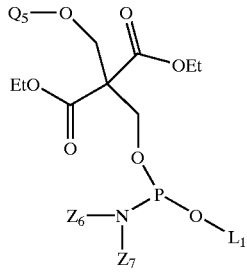

thereby forming a 5'-functionalized compound; wherein
$Q_5$ is an acid labile hydroxyl protecting group.

18. The process of claim 17 further comprising the step of treating said 5'-functionalized compound with a capping agent to form a capped compound.

19. The process of claim 17 wherein at least one of said $L_1$, $L_2$, and $L_3$ is attached to the oligonucleotide through a linking group.

20. The process of claim 19 wherein the linking group comprises a dialkylglycerol linker.

21. The process of claim 17 wherein each of said $Z_6$ and $Z_7$ is isopropyl.

22. The process of claim 17 wherein $L_1$ is different from $L_2$ and $L_3$.

23. The process of claim 17 wherein each of said $Q_3$ is independently selected from the group consisting of cyanoethyl, diphenylsilyletbyl, cyanobutenyl, cyano p-xylyl (CPX), methyl-N-trifluoroacetyl ethyl (META) and acetoxy phenoxy ethyl (APOE) groups.

24. The process of claim 17 wherein each of said $Q_1$ and $Q_2$ is independently selected from the group consisting of trimethoxytrityl, dimethoxytrityl (DMT), monomethoxytrityl, 9-phenylxanthen-9-yl (Pixyl) and 9-(p-methoxyphenyl)xanthen-9-yl (Mox).

25. The process of claim 17 wherein each of said Bx is independently selected from the group consisting of adenine, guanine, thymine, cytosine, uracil, 5-methylcytosine (5-me-C), 5-hydroxymethyl cytosine, xanthine, hypoxanthine, 2-aminoadenine, alkyl derivatives of adenine and guanine, 2-thiouracil, 2-thiothymine, 2-thiocytosine, 5-halouracil, 5-halocytosine, 5-propynyl uracil, 5-propynyl cytosine, 6-azo uracil, 6-azo cytosine, 6-azo thymine, 5-uracil (pseudouracil), 4-thiouracil, 8-substituted adenines and guanines, 5-substituted uracils and cytosines, 7-methylguanine, 7-methyladenine, 8-azaguanine, 8-azaadenine, 7-deazaguanine, 7-deazaadenine, 3-deazaguanine and 3-deazaadenine.

* * * * *

UNITED STATES PATENT AND TRADEMARK OFFICE
CERTIFICATE OF CORRECTION

PATENT NO.    : 6,825,338 B2                                              Page 1 of 1
DATED         : November 30, 2004
INVENTOR(S)   : Muthiah Manoharan et al.

It is certified that error appears in the above-identified patent and that said Letters Patent is hereby corrected as shown below:

<u>Title page,</u>
Item [56], References Cited, OTHER PUBLICATIONS, "Iyer" reference, delete "PhosphorothioAtes" and insert -- Phosphorothioates --;

<u>Column 87,</u>
Line 67, delete ";" and insert -- : --;

<u>Column 89,</u>
Line 18, delete "conditiong" and insert -- conditions --;
Line 66, delete "5-hydroxymetliyl" and insert -- 5-hydroxymethyl --;

<u>Column 91,</u>
Line 9, delete "philhalimido" and insert -- phthalimido --;
Line 14, delete "echoxy" and insert -- ethoxy --;

<u>Column 92,</u>
Line 16, delete "trichioroethoxy" and insert -- trichloroethoxy --;
Line 44, delete "2'-substituen" and insert -- 2'-substituent --;

<u>Column 94,</u>
Line 34, delete "diphenylsilyletbyl" and insert -- diphenylsilylethyl --.

Signed and Sealed this

Second Day of May, 2006

JON W. DUDAS
*Director of the United States Patent and Trademark Office*

SEQUENCE LISTING

```
<160> NUMBER OF SEQ ID NOS: 21

<210> SEQ ID NO 1
<211> LENGTH: 12
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 1
tttttttttt tt                                                            12

<210> SEQ ID NO 2
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 2
atgcattctg cccccaagga                                                    20

<210> SEQ ID NO 3
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 3
agcttctttg cacatgtaaa                                                    20

<210> SEQ ID NO 4
<211> LENGTH: 19
```

```
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 4
tgcatccccc aggccacca                                              19

<210> SEQ ID NO 5
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 5
tgcatccccc aggccacca                                              19

<210> SEQ ID NO 6
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 6
tgcatccccc aggccacca                                              19

<210> SEQ ID NO 7
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 7
tgcatccccc aggccacca                                              19

<210> SEQ ID NO 8
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 8
tgcatccccc aggccaccat                                             20

<210> SEQ ID NO 9
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 9
tgcatccccc aggccacca                                              19

<210> SEQ ID NO 10
<211> LENGTH: 22
<212> TYPE: DNA
```

```
<213> ORGANISM: Artificial Sequence
<220> FEATURE:
<221> NAME/KEY: misc_feature
<223> OTHER INFORMATION: Oligonucleotide

<400> SEQUENCE: 10
gcatcatccc ccaggccacc at                                              22

<210> SEQ ID NO 11
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 11
tgcatccccc aggccaccat                                                 20

<210> SEQ ID NO 12
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 12
gcccaagctg gcatccgtca                                                 20

<210> SEQ ID NO 13
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 13
tccgtcatcg ctcctcaggg                                                 20

<210> SEQ ID NO 14
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 14
gtccaccatt agcacgcggg                                                 20

<210> SEQ ID NO 15
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 15
gtccaccatt agcacgcggg                                                 20

<210> SEQ ID NO 16
<211> LENGTH: 18
<212> TYPE: DNA
<213> ORGANISM: Artificial Sequence
```

```
<220> FEATURE:
<221> NAME/KEY: misc_feature
<223> OTHER INFORMATION: Oligonucleotide

<400> SEQUENCE: 16
cctcttacct cagttaca                                                18

<210> SEQ ID NO 17
<211> LENGTH: 18
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 17
gctattacct taacccag                                                18

<210> SEQ ID NO 18
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 18
ctgctagcct ctggatttga                                              20

<210> SEQ ID NO 19
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 19
cttctggcat ccggtttaga                                              20

<210> SEQ ID NO 20
<211> LENGTH: 18
<212> TYPE: RNA
<213> ORGANISM: Artificial Sequence
<220> FEATURE:
<221> NAME/KEY: misc_feature
<223> OTHER INFORMATION: Oligonucleotide

<400> SEQUENCE: 20
ccucuuaccu caguuaca                                                18

<210> SEQ ID NO 21
<211> LENGTH: 18
<212> TYPE: RNA
<213> ORGANISM: Artificial Sequence
<220> FEATURE:
<221> NAME/KEY: misc_feature
<223> OTHER INFORMATION: Oligonucleotide

<400> SEQUENCE: 21
gcuauuaccu uaacccag                                                18
```